US009670269B2

(12) United States Patent
Igawa et al.

(10) Patent No.: US 9,670,269 B2
(45) Date of Patent: Jun. 6, 2017

(54) METHODS OF MODIFYING ANTIBODIES FOR PURIFICATION OF BISPECIFIC ANTIBODIES

(75) Inventors: Tomoyuki Igawa, Shizuoka (JP); Hiroyuki Tsunoda, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/295,075

(22) PCT Filed: Mar. 30, 2007

(86) PCT No.: PCT/JP2007/057058
§ 371 (c)(1),
(2), (4) Date: Apr. 20, 2009

(87) PCT Pub. No.: WO2007/114325
PCT Pub. Date: Oct. 11, 2007

(65) Prior Publication Data
US 2009/0263392 A1 Oct. 22, 2009

(30) Foreign Application Priority Data

Mar. 31, 2006 (JP) .................................. 2006-097795
Oct. 6, 2006 (JP) .................................. 2006-275804

(51) Int. Cl.
*C07K 16/00* (2006.01)
*C07K 16/24* (2006.01)

(52) U.S. Cl.
CPC .......... *C07K 16/00* (2013.01); *C07K 16/248* (2013.01); *C07K 2317/24* (2013.01); *C07K 2317/31* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,208,479 A | 6/1980 | Zuk et al. |
| 4,444,878 A | 4/1984 | Paulus |
| 4,474,893 A | 10/1984 | Reading |
| 5,126,250 A | 6/1992 | McDonough et al. |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,837,821 A | 11/1998 | Wu |
| 5,859,205 A * | 1/1999 | Adair et al. ............... 530/387.3 |
| 5,877,291 A | 3/1999 | Mezes et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,025,165 A | 2/2000 | Whitlow et al. |
| 6,126,980 A | 10/2000 | Smith et al. |
| 6,132,992 A | 10/2000 | Ledbetter et al. |
| 6,183,744 B1 | 2/2001 | Goldenberg |
| 6,323,000 B2 | 11/2001 | Briggs et al. |
| 6,329,511 B1 | 12/2001 | Vasquez et al. |
| 6,342,220 B1 | 1/2002 | Adams et al. |
| 6,368,596 B1 | 4/2002 | Ghetie et al. |
| 6,485,943 B2 | 11/2002 | Stevens et al. |
| 6,677,436 B1 | 1/2004 | Sato et al. |
| 6,683,157 B2 | 1/2004 | Briggs et al. |
| 6,699,686 B1 | 3/2004 | Brocard et al. |
| 6,723,319 B1 | 4/2004 | Ito et al. |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |

(Continued)

FOREIGN PATENT DOCUMENTS

| | | |
|---|---|---|
| AU | 755822 | 3/1999 |
| AU | 2009290162 | 4/2010 |

(Continued)

OTHER PUBLICATIONS

Smans et al. (Int. J. Cancer, 83:270:277, 1999).*
Onda et al. (Cancer Res., 61:5070:5077, 2001).*
Manz et al. (Bioanalytical Chemistry, World Scientific Publishing Co., 2003).*
Roguska et al. (PNAS, 91: 969-973, 1994).*
Hombach et al. (Int. J. Cancer, 55: 830-836, 1993).*
Staerz and Bevan (PNAS, 83: 1453-1457).*
Manzke et al. (Journal of Immunological Methods, 208: 65-73, 1997).*
Haagen et al. (Cancer Immunol Immunother, 39: 391-396, 1994).*
Exhibit A (IMGT Scientific charts depicting the correspondence between Eu and Kabat numberings for the human IgG constant region, created May 17, 2001 and last updated Aug. 13, 2014).*

(Continued)

*Primary Examiner* — Misook Yu
*Assistant Examiner* — Nelson B Moseley, II
(74) *Attorney, Agent, or Firm* — Fish & Richardson P.C.

(57) ABSTRACT

The present inventors devised methods for efficiently purifying bispecific antibodies using a chromatography column based on the difference in isoelectric points between the H chains of two types of antibodies, wherein the difference is introduced by modifying the amino acids present on the surface of the antibody variable regions of two types of antibodies that constitute a bispecific antibody. Furthermore, the inventors devised methods for efficiently purifying bispecific antibodies using a chromatography column by linking respective antigen binding sites (heavy chain variable regions) to the antibody constant regions having different isoelectric points, and then coexpressing these antibodies.

25 Claims, 22 Drawing Sheets

(56) References Cited

U.S. PATENT DOCUMENTS

| | | | |
|---|---|---|---|
| 7,538,196 B2 | 5/2009 | Jung | |
| 7,732,149 B2 | 6/2010 | Kojima et al. | |
| 8,062,635 B2 | 11/2011 | Hattori et al. | |
| 8,217,147 B2 | 7/2012 | Stavenhagen et al. | |
| 8,592,562 B2 | 11/2013 | Kannan et al. | |
| 8,597,911 B2 | 12/2013 | Miyazaki et al. | |
| 9,096,651 B2 | 8/2015 | Igawa et al. | |
| 9,228,017 B2 | 1/2016 | Igawa et al. | |
| 9,334,331 B2 | 5/2016 | Igawa et al. | |
| 2001/0001663 A1 | 5/2001 | Kishimoto et al. | |
| 2001/0006796 A1 | 7/2001 | Briggs et al. | |
| 2002/0028178 A1 | 3/2002 | Hanna et al. | |
| 2002/0062010 A1 | 5/2002 | Arathoon et al. | |
| 2002/0142374 A1 | 10/2002 | Gallo et al. | |
| 2002/0147326 A1 | 10/2002 | Chaiklin et al. | |
| 2002/0155537 A1 | 10/2002 | Carter et al. | |
| 2002/0164339 A1 | 11/2002 | Do et al. | |
| 2002/0164668 A1* | 11/2002 | Durham et al. | 435/7.92 |
| 2002/0187150 A1 | 12/2002 | Mihara et al. | |
| 2002/0193571 A1 | 12/2002 | Carter et al. | |
| 2002/0197706 A1 | 12/2002 | Nadkarni et al. | |
| 2003/0073161 A1 | 4/2003 | Briggs et al. | |
| 2003/0082612 A1 | 5/2003 | Snodgrass et al. | |
| 2003/0148409 A1 | 8/2003 | Rossi et al. | |
| 2003/0190311 A1* | 10/2003 | Dall'Acqua et al. | 424/130.1 |
| 2003/0207346 A1 | 11/2003 | Arathoon et al. | |
| 2003/0219441 A1 | 11/2003 | Thorpe et al. | |
| 2003/0224397 A1 | 12/2003 | Lowman et al. | |
| 2004/0071706 A1 | 4/2004 | Ito et al. | |
| 2004/0081651 A1 | 4/2004 | Karpusas et al. | |
| 2004/0091475 A1 | 5/2004 | Tsuchiya et al. | |
| 2004/0219643 A1 | 11/2004 | Winter et al. | |
| 2004/0236080 A1 | 11/2004 | Aburatani et al. | |
| 2004/0242847 A1 | 12/2004 | Fukushima et al. | |
| 2005/0095243 A1 | 5/2005 | Chan et al. | |
| 2005/0130224 A1 | 6/2005 | Saito et al. | |
| 2005/0142133 A1 | 6/2005 | Lazar et al. | |
| 2005/0142635 A1 | 6/2005 | Tsuchiya et al. | |
| 2005/0191293 A1 | 9/2005 | Deshpande et al. | |
| 2005/0244403 A1 | 11/2005 | Lazar et al. | |
| 2005/0261229 A1 | 11/2005 | Gillies | |
| 2005/0266425 A1 | 12/2005 | Zauderer et al. | |
| 2006/0019342 A1 | 1/2006 | Dall Acqua et al. | |
| 2006/0024298 A1 | 2/2006 | Lazar et al. | |
| 2006/0058511 A1 | 3/2006 | Tanikawa et al. | |
| 2006/0063228 A1 | 3/2006 | Kasaian et al. | |
| 2006/0134709 A1 | 6/2006 | Stavenhagen et al. | |
| 2006/0141456 A1 | 6/2006 | Edwards et al. | |
| 2006/0159673 A1 | 7/2006 | Kojima | |
| 2006/0160184 A1* | 7/2006 | Mattheus Hoogenboom et al. | 435/69.1 |
| 2006/0189794 A1 | 8/2006 | Tsuchiya et al. | |
| 2006/0194280 A1 | 8/2006 | Dillon et al. | |
| 2006/0204493 A1* | 9/2006 | Huang et al. | 424/133.1 |
| 2006/0222643 A1 | 10/2006 | Tsunoda et al. | |
| 2006/0269989 A1 | 11/2006 | Miyazaki et al. | |
| 2006/0275282 A1 | 12/2006 | Moore et al. | |
| 2006/0275301 A1 | 12/2006 | Ozaki et al. | |
| 2006/0292147 A1 | 12/2006 | Yoshizaki et al. | |
| 2007/0003556 A1 | 1/2007 | Tsuchiya et al. | |
| 2007/0036785 A1 | 2/2007 | Kishimoto et al. | |
| 2007/0041978 A1 | 2/2007 | Hattori et al. | |
| 2007/0054354 A1* | 3/2007 | Humphreys et al. | 435/69.1 |
| 2007/0059312 A1 | 3/2007 | Baca et al. | |
| 2007/0087381 A1 | 4/2007 | Kojima | |
| 2007/0110757 A1* | 5/2007 | Wei et al. | 424/159.1 |
| 2007/0134234 A1 | 6/2007 | Smith et al. | |
| 2007/0148164 A1 | 6/2007 | Farrington et al. | |
| 2007/0224188 A1 | 9/2007 | Allan et al. | |
| 2007/0281327 A1 | 12/2007 | Nakano et al. | |
| 2008/0009038 A1 | 1/2008 | Ohtomo et al. | |
| 2008/0063635 A1 | 3/2008 | Takahashi et al. | |
| 2008/0075712 A1 | 3/2008 | Hattori et al. | |
| 2008/0166756 A1 | 7/2008 | Tsuchiya et al. | |
| 2008/0206229 A1 | 8/2008 | Ono et al. | |
| 2009/0028854 A1 | 1/2009 | Igawa et al. | |
| 2009/0117097 A1 | 5/2009 | Igawa et al. | |
| 2009/0208416 A1 | 8/2009 | Moretta et al. | |
| 2009/0214535 A1 | 8/2009 | Igawa et al. | |
| 2009/0221803 A1 | 9/2009 | Dall'Acqua et al. | |
| 2009/0297501 A1 | 12/2009 | Igawa et al. | |
| 2009/0324589 A1 | 12/2009 | Igawa et al. | |
| 2010/0003254 A1 | 1/2010 | Hattori et al. | |
| 2010/0004429 A1 | 1/2010 | Kai et al. | |
| 2010/0008907 A1 | 1/2010 | Nishimoto et al. | |
| 2010/0015133 A1 | 1/2010 | Igawa et al. | |
| 2010/0055092 A1 | 3/2010 | Hasegawa et al. | |
| 2010/0239577 A1 | 9/2010 | Igawa et al. | |
| 2010/0291072 A1 | 11/2010 | Lowman et al. | |
| 2010/0298542 A1 | 11/2010 | Igawa et al. | |
| 2011/0076275 A1* | 3/2011 | Igawa et al. | 424/136.1 |
| 2011/0111406 A1 | 5/2011 | Igawa et al. | |
| 2011/0129459 A1 | 6/2011 | Kuramochi et al. | |
| 2011/0236374 A1 | 9/2011 | Shitara et al. | |
| 2011/0245473 A1 | 10/2011 | Igawa et al. | |
| 2012/0028304 A1 | 2/2012 | Dahiyat et al. | |
| 2012/0065379 A1 | 3/2012 | Igawa et al. | |
| 2012/0071634 A1 | 3/2012 | Igawa et al. | |
| 2012/0237517 A1 | 9/2012 | Hattori et al. | |
| 2012/0238729 A1 | 9/2012 | Kuramochi et al. | |
| 2013/0011866 A1 | 1/2013 | Igawa et al. | |
| 2013/0018174 A1 | 1/2013 | Igawa et al. | |
| 2013/0030156 A1 | 1/2013 | Apostolou et al. | |
| 2013/0052196 A1 | 2/2013 | Apostolou et al. | |
| 2013/0101581 A1 | 4/2013 | Kuramochi et al. | |
| 2013/0195849 A1 | 8/2013 | Spreter et al. | |
| 2013/0330345 A1 | 12/2013 | Igawa et al. | |
| 2014/0037632 A1 | 2/2014 | Igawa et al. | |
| 2014/0112883 A1 | 4/2014 | Ponath et al. | |
| 2014/0112914 A1 | 4/2014 | Nezu et al. | |
| 2014/0370018 A1 | 12/2014 | Igawa et al. | |
| 2014/0377253 A1 | 12/2014 | Harding et al. | |
| 2015/0118184 A1 | 4/2015 | Kawai | |
| 2015/0274809 A1 | 10/2015 | Igawa et al. | |
| 2015/0284465 A1 | 10/2015 | Igawa et al. | |
| 2015/0315278 A1 | 11/2015 | Igawa et al. | |
| 2016/0159915 A1 | 6/2016 | Igawa et al. | |
| 2016/0222129 A1 | 8/2016 | Igawa et al. | |
| 2016/0229908 A1 | 8/2016 | Igawa et al. | |
| 2016/0229915 A1 | 8/2016 | Igawa et al. | |

FOREIGN PATENT DOCUMENTS

| | | |
|---|---|---|
| CA | 2 203 182 | 5/1996 |
| CA | 2 331 641 | 11/1999 |
| CA | 2 019 559 | 1/2002 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CN | 1842540 | 10/2006 |
| CN | 101198698 | 6/2008 |
| CN | 102471378 | 5/2012 |
| DE | 198 19 846 | 11/1999 |
| EP | 0 369 566 | 5/1990 |
| EP | 437 622 | 7/1991 |
| EP | 0637593 | 2/1995 |
| EP | 0 404 097 | 9/1996 |
| EP | 0 774 511 | 5/1997 |
| EP | 0 783 893 | 7/1997 |
| EP | 811 691 | 12/1997 |
| EP | 1 069 185 | 1/2001 |
| EP | 1 220 923 | 7/2002 |
| EP | 1 327 681 | 7/2003 |
| EP | 1510943 A1 | 3/2005 |
| EP | 0 979 281 | 7/2005 |
| EP | 1 605 058 | 12/2005 |
| EP | 1 674 111 | 6/2006 |
| EP | 1 693 448 | 8/2006 |

(56) References Cited

FOREIGN PATENT DOCUMENTS

| | | |
|---|---|---|
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 381 | 12/2008 |
| EP | 2 031 064 | 3/2009 |
| EP | 1 505 148 | 4/2009 |
| EP | 2 107 115 | 10/2009 |
| EP | 2 194 066 | 6/2010 |
| EP | 2 196 541 | 6/2010 |
| EP | 2 206 775 | 7/2010 |
| EP | 2 275 443 | 1/2011 |
| EP | 1 688 488 | 8/2011 |
| EP | 2354161 | 8/2011 |
| EP | 2409991 | 1/2012 |
| EP | 2 522 724 | 11/2012 |
| EP | 2 543 727 | 1/2013 |
| EP | 2914634 | 9/2015 |
| JP | S63-52890 | 3/1988 |
| JP | 2-028200 | 1/1990 |
| JP | 2-145187 | 6/1990 |
| JP | 5-184383 | 7/1993 |
| JP | 5-199894 | 8/1993 |
| JP | 5-203652 | 8/1993 |
| JP | 5-213775 | 8/1993 |
| JP | 5-304992 | 11/1993 |
| JP | 07-67688 | 3/1995 |
| JP | 7-503622 | 4/1995 |
| JP | 8-500979 | 2/1996 |
| JP | 8-510555 | 11/1996 |
| JP | 09-506001 | 6/1997 |
| JP | 10-505231 | 5/1998 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-506310 | 6/1999 |
| JP | 3032287 | 4/2000 |
| JP | 2001/506135 | 5/2001 |
| JP | 2001-513999 | 9/2001 |
| JP | 2001-518930 | 10/2001 |
| JP | 2001-523971 | 11/2001 |
| JP | 2002-514406 | 5/2002 |
| JP | 2002-518041 | 6/2002 |
| JP | 2002-543822 | 12/2002 |
| JP | 2002-544173 | 12/2002 |
| JP | 2003-055398 | 2/2003 |
| JP | 2003-509049 | 3/2003 |
| JP | 2003-515323 | 5/2003 |
| JP | 2004-086862 | 3/2004 |
| JP | 2004-511426 | 4/2004 |
| JP | 2005-535341 | 11/2005 |
| JP | 2005/537009 | 12/2005 |
| JP | 2008-512995 | 5/2008 |
| JP | 2008-538920 | 11/2008 |
| JP | 2009-500458 | 1/2009 |
| JP | 2012-510281 | 6/2010 |
| JP | 2011-508604 | 3/2011 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 5717624 | 5/2015 |
| MX | 9905856 A | 7/2000 |
| RU | 94028282 | 7/1996 |
| RU | 2232773 | 7/2004 |
| RU | 2266298 | 12/2005 |
| RU | 2339696 | 11/2008 |
| TW | 2007/14313 | 4/2007 |
| TW | I452135 | 9/2014 |
| TW | I452136 | 9/2014 |
| WO | WO 91/01335 | 2/1991 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/14710 | 6/1995 |
| WO | WO 95/33844 | 12/1995 |
| WO | WO 96/01653 | 1/1996 |
| WO | WO 96/04925 | 2/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/34892 | 11/1996 |
| WO | WO 97/09351 | 3/1997 |
| WO | WO 97/10354 | 3/1997 |
| WO | WO 97/31108 | 8/1997 |
| WO | WO 98/03546 | 1/1998 |
| WO | WO 98/28331 | 7/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/18212 | 4/1999 |
| WO | WO 99/51743 | 10/1999 |
| WO | WO 99/58572 | 11/1999 |
| WO | WO 99/67359 | 12/1999 |
| WO | WO 00/18806 | 4/2000 |
| WO | WO 00/44788 | 8/2000 |
| WO | WO 00/67795 | 11/2000 |
| WO | WO 00/69462 | 11/2000 |
| WO | WO 01/19992 | 3/2001 |
| WO | WO 01/30854 | 5/2001 |
| WO | WO 01/36486 | 5/2001 |
| WO | WO 01/44282 | 6/2001 |
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/79494 | 10/2001 |
| WO | WO 01/82899 | 11/2001 |
| WO | WO 01/90192 | 11/2001 |
| WO | WO 01/97858 | 12/2001 |
| WO | WO 02/04021 | 1/2002 |
| WO | WO 02/06838 | 1/2002 |
| WO | WO 02/22212 | 3/2002 |
| WO | WO 02/33072 | 4/2002 |
| WO | WO 02/33073 | 4/2002 |
| WO | WO 02/072605 | 9/2002 |
| WO | WO 02/078612 | 10/2002 |
| WO | WO 03/000883 | 1/2003 |
| WO | WO 03/020949 | 3/2003 |
| WO | WO 03/033654 | 4/2003 |
| WO | WO 03/035835 | 5/2003 |
| WO | WO 03/042231 | 5/2003 |
| WO | WO 03/087163 | 10/2003 |
| WO | WO 03/091424 | 11/2003 |
| WO | WO 03/104425 | 12/2003 |
| WO | WO 03/105757 | 12/2003 |
| WO | WO 2004/003019 | 1/2004 |
| WO | WO 2004/009618 | 1/2004 |
| WO | WO 2004/016740 | 2/2004 |
| WO | WO 2004/019966 | 3/2004 |
| WO | WO 2004/020579 | 3/2004 |
| WO | WO 2004/033499 | 4/2004 |
| WO | WO 2004/060919 | 7/2004 |
| WO | WO 2004/065611 | 8/2004 |
| WO | WO 2004/068931 | 8/2004 |
| WO | WO 2004/081048 | 9/2004 |
| WO | WO 2004/087763 | 10/2004 |
| WO | WO 2004/096273 | 11/2004 |

(56) References Cited

FOREIGN PATENT DOCUMENTS

| WO | WO 2004/097041 | 11/2004 |
|---|---|---|
| WO | WO 2004/111233 | 12/2004 |
| WO | WO 2004/113387 | 12/2004 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056604 | 6/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/107784 | 11/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047350 | 5/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/060411 | 5/2007 |
| WO | WO 2007/108559 | 9/2007 |
| WO | WO 2007/114319 | 10/2007 |
| WO | WO 2007/114325 | 10/2007 |
| WO | WO2007114325 A1 | 10/2007 |
| WO | WO 2007/142325 | 12/2007 |
| WO | WO 2007/145941 | 12/2007 |
| WO | WO 2008/043822 | 4/2008 |
| WO | WO 2008/090960 | 7/2008 |
| WO | WO 2008/092117 | 7/2008 |
| WO | WO 2008/119353 | 10/2008 |
| WO | WO 2008/145141 | 12/2008 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/089004 | 7/2009 |
| WO | WO 2009/100309 | 8/2009 |
| WO | WO 2009/120922 | 10/2009 |
| WO | WO 2009/125825 | 10/2009 |
| WO | WO 2009/134776 | 11/2009 |
| WO | WO 2009/139822 | 11/2009 |
| WO | WO 2010/034441 | 4/2010 |
| WO | WO 2010/035769 | 4/2010 |
| WO | WO 2010/063746 | 6/2010 |
| WO | WO 2010/064090 | 6/2010 |
| WO | WO 2010/102251 | 9/2010 |
| WO | WO 2010/107109 | 9/2010 |
| WO | WO 2010/107110 | 9/2010 |
| WO | WO 2010/151792 | 12/2010 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/131746 | 10/2011 |
| WO | WO 2011/133886 | 10/2011 |
| WO | WO 2011/143545 | 11/2011 |
| WO | WO 2012/067176 | 5/2012 |
| WO | WO 2012/073985 | 6/2012 |
| WO | WO 2012/145238 | 10/2012 |
| WO | WO 2013/060867 | 5/2013 |
| WO | WO 2015/046467 | 4/2015 |
| WO | WO 2016/125495 | 8/2016 |

OTHER PUBLICATIONS

Exhibit B (IMGT Scientific charts depicting the correspondence between Eu and Kabat numberings for the human IgG constant region, created May 17, 2001 and last updated Aug. 13, 2014).*
Suresh et al. (Methods in Enzymology, 121: 210-228, 1986).*
Branden and Tooze, "Recognition of Foreign Molecules by the Immune System," *Introduction to Protein Structure, 2d Ed.*, Garland Publishing, pp. 299-323 (1999).
Carter, "Bispecific human IgG by design," J. Immunol Methods, 248:7-15 (2001).
Gupta and Suresh, "Affinity chromatography and co-chromatography of bispecific monoclonal antibody immunoconjugates," J. Biochem. Biophys. Methods, 51:203-216 (2002).
Kreutz et al., "Efficient bispecific monoclonal antibody purification using gradient thiophilic affinity chromatography," J. Chromatogr. B, 714:161-170 (1998).
Lindhofer et al., "Preferential Species-Restricted Heavy/Light Chain Pairing in Rat/Mouse Quadromas," J. Immunol , 155:219-225 (1995).
Manzke et al., "Single-step purification of bispecific monoclonal antibodies for immunotherapeutic use by hydrophobic interaction chromatography," J. Immunol Methods, 208:65-73 (1997).
Marvin and Zhu, "Recombinant approaches to IgG-like bispecific antibodies," Acta. Pharmacol. Sin., 26(6):649-658 (2005).
Merchant et al., "An efficient route to human bispecific IgG," Nat. Biotechnol., 16:677-681 (1998).
Segal et al., "Bispecific antibodies in cancer therapy," Curr. Opin. Immunol., 11:558-562 (1999).
Tarditi et al., "Selective high-performance liquid chromatographic purification of bispecific monoclonal antibodies," J. Chromatogr., 599:13-20 (1992).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Chamow et al., "A humanized, bispecific immunoadhesin-antibody that retargets CD3+ effectors to kill HIV-1-infected cells," *J. Immunol.*, 153(9):4268-80 (1994).
Panka et al., "Variable region framework differences result in decreased or increased affinity of variant anti-digoxin antibodies," *Proc. Natl. Acad. Sci. U.S.A.*, 85(9):3080-4 (1988).
Fish & Richardson P.C., Response to Restriction Requirement dated Oct. 12, 2010 in U.S. Appl. No. 12/295,039, filed Apr. 11, 2011, 9 pages.
Adams et al., "Humanization of a recombinant monoclonal antibody to produce a therapeutic HER dimerization inhibitor, pertuzumab," *Cancer Immunol. Immunother.*, 55:717-727 (2006).
Binz et al., "Engineering novel binding proteins from nonimmunoglobulin domains," *Nature Biotechnol.*, 23:1257-68 (2005).
Comper and Glasgow, "Charge selectivity in kidney ultrafiltration," *Kidney Int.*, 47:1242-51 (1995).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Deen et al., "Structural determinants of glomerular permeability," *Am. J. Physiol. Renal. Physiol.*, 281:F579-F596 (2001).
Del Rio et al., "An Engineered Penicillin Acylase with Altered Surface Charge is More Stable in Alkaline pH," *Ann. NY Acad. Sci.*, 799:61-64 (1996).

(56) References Cited

OTHER PUBLICATIONS

Ewert et al., "Stability improvement of antibodies for extracellular and intracellular applications: CDR grafting to stable frameworks and structure-based framework engineering," *Methods*, 34:184-199 (2004).
Ghetie and Ward, "FcRn: the MHC class I-related receptor that is more than an IgG transporter," *Immunol. Today*, 18(12):592-598 (1997).
Ghetie et al., "Increasing the serum persistence of an IgG fragment by random mutagenesis," *Nat. Biotechnol.*, 15:637-640 (1997).
Ghetie et al., "Multiple roles for the major histocompatibility complex class I-related receptor FcRn," *Annu. Rev. Immunol.*, 18:739-766 (2000).
Gobburu et al., "Pharmacokinetics/Dynamics of 5c8, a Monoclonal Antibody to CD154 (CD40 Ligand) Suppression of an Immune Response in Monkeys," *J. Pharmacol. Exp. Ther.*, 286:925-930 (1998).
Goode et al., "The glomerular basement membrane charge-selectivity barrier: an oversimplified concept?" *Nephrol. Dial. Transplant.*, 11:1714-16 (1996).
Graves et al., "Molecular Modeling and Preclinical Evaluation of the Humanized NR-LU-13 Antibody," *Clin. Cancer Res.*, 5:899-908 (1999).
U.S. Appl. No. 12/295,039, filed Sep. 29, 2008, Igawa et al.
He et al., "Humanization and Pharmacokinetics of a Monoclonal Antibody with Specificity for Both E- and P-Selectin," *J. Immunol.*, 1029-35 (1998).
Hinton et al., "An Engineered Human IgG1 Antibody with Longer Serum Half-Life," *J. Immunol.*, 346-356 (2006).
Kashmiri et al., "Generation, Characterization, and in Vivo Studies of Humanized Anticarcinoma Antibody CC49," *Hybridoma*, 14:461-473 (1995).
Khawli et al., "Improved tumor localization and radioimaging with chemically modified monoclonal antibodies," *Cancer. Biother. Radiopharm.*, 11:203-215 (1996).
Kim et al., "Antibody Engineering for the Development of Therapeutic Antibodies," *Mol. Cells*, 20:17-29 (2005).
Kim et al., "Chemical Modification to Reduce Renal Uptake of Disulfide-Bonded Variable Region Fragment of Anti-Tac Monoclonal Antibody Labeled with $^{99m}$Tc," *Bioconjugate Chem.*, 10:447-453 (1999).
Kim et al., "Lowering of pI by acylation improves the renal uptake of $^{99m}$Tc-labeled anti-Tac dsFv: effect of different acylating reagents," *Nucl. Med. Biol.*, 29:795-801 (2002).
Kobayashi et al., "The Pharmacokinetic Characteristics of Glycolated Humanized Anti-Tac Fabs Are Determined by Their Isoelectric Points," *Cancer Res.*, 59:422-430 (1999).
Lobo et al., "Antibody Pharmacokinetics and Pharmacodynamics," *J. Pharm. Sci.*, 93:2645-68 (2004).
Martin et al., "Crystal structure at 2.8 Å of an FcRn/heterodimeric Fc complex: mechanism of pH-dependent binding," *Mol. Cell*, 7:867-877 (2001).
Onda et al., "Lowering the Isoelectric Point of the Fv Portion of Recombinant Immunotoxins Leads to Decreased Nonspecific Animal Toxicity without Affecting Antitumor Activity," *Cancer Res.*, 61:5070-77 (2001).
Pavlinkova et al., "Charge-Modified Single Chain Antibody Constructs of Monoclonal Antibody CC49: Generation, Characterization, Pharmacokinetics, and Biodistribution Analysis," *Nucl. Med. Biol.*, 26:27-34 (1999).
Pavlou and Belsey, "The therapeutic antibodies market to 2008," *Eur. J. Pharm. Biopharm.*, 59:389-396 (2005).
Poduslo and Curran, "Polyamine Modification Increases the Permeability of Proteins at the Blood-Nerve and Blood-Brain Barriers," *J. Neurochem.*, 1599-1609 (1996).
Rajpal et al., "A general method for greatly improving the affinity of antibodies by using combinational libraries," *Proc. Natl. Acad. Sci. USA*, 102:8466-71 (2005).
Reichert et al., "Monoclonal antibody successes in the clinic," *Nat. Biotechnol.*, 23:1073-78 (2005).

Schaeffer et al., "The Rat Glomerular Filtration Barrier Does Not Show Negative Charge Selectivity," *Microcirculation*, 9:329-342 (2002).
Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.*, 276:6591-6604 (2000).
Ten Kate et al., "Effect of isoelectric point on biodistribution and inflammation: imaging with indium-111-labelled IgG," *Eur. J. Nucl. Med.*, 17:305-309 (1990).
Tsurushita et al., "Design of humanized antibodies: From anti-Tac to Zenapax," *Methods*, 36:69-83 (2005).
Yamasaki et al., "Pharmacokinetic Analysis of in Vivo Disposition of Succinylated Proteins Targeted to Liver Nonparenchymal Cells via Scavenger Receptors: Importance of Molecular Size and Negative Charge Density for in Vivo Recognition by Receptors," *J. Pharmacol. Exp. Ther.*, 301:467-477 (2002).
Yang et al., "Tailoring structure-function and pharmacokinetic properties of single-chain Fv proteins by site-specific PEGylation," *Protein Engineering*, 16:761-770 (2003).
Zuckier et al., "Chimeric Human-Mouse IgG Antibodies with Shuffled Constant Region Exons Demonstrate that Multiple Domains Contribute to in Vivo Half-Life," *Cancer Res.* 58:3905-08 (1998).
International Preliminary Report on Patentability for App. Ser. No. PCT/JP2007/057036, dated Oct. 21, 2008, 6 pages.
Japanese Patent Office, International Search Report for App. Ser. No. PCT/JP2007/057036, dated May 1, 2007, 2 pages.
European Search Report for Application No. EP 07 74 0474, dated Mar. 16, 2009, 5 pages.
International Preliminary Report on Patentability for App. Ser. No. PCT/JP2007/057058, dated Oct. 21, 2008, 11 pages.
Japanese Patent Office, International Search Report App. Ser. No. PCT/JP2007/057058, mailed May 7, 2001, 2 pages.
Fish & Richardson P.C., Amendment in U.S. Appl. No. 10/575,193, filed Jun. 17, 2011, 15 pages.
USPTO Notice of Allowance in U.S. Appl. No. 10/575,193, mailed Jul. 13, 2011, 8 pages.
USPTO Non-Final Office Action in U.S. Appl. No. 12/295,039, dated Jun. 28, 2011, 9 pages.
Fish & Richardson P.C., Amendment in Reply to Final Office Action dated Jun. 3, 2010 in U.S. Appl. No. 10/560,098, filed Jul. 5, 2011, 17 pages.
USPTO Restriction Requirement in U.S. Appl. No. 11/910,128, dated Jun. 9, 2011, 10 pages.
Fish & Richardson P.C., Response to Restriction Requirement dated Mar. 18, 2011 in U.S. Appl. No. 11/910,836, filed Sep. 6, 2011, 1 page.
European Search Report for App. Ser. No. 07 74 0494, dated Sep. 3, 2009, 3 pages.
Marvin et al., "Redesigning an antibody fragment for faster association with its antigen," Biochemistry, 42:7077-83 (2003).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Shaul, "Exploring the charge space of protein-protein association: a proteomic study," Proteins, 60:341-352 (2005).
USPTO Final Office Action in U.S. Appl. No. 10/575,905, mailed Feb. 24, 2011, 7 pages.
Abe et al., "Surrogate thrombopoietin," *Immunology Letters*, 61:73-78 (1998).
Andris-Widhopf et al., "Methods for the generation of chicken monoclonal antibody fragments by phage display," *Journal of Immunological Methods*, 242:159-181 (2000).
Arndt et al., "Factors influencing the dimer to monomer transition of an antibody single-chain Fv fragment," *Biochemistry*, 37(37):12918-26 (1998).
Arndt et al., "Generation of a highly stable, internalizing anti-DC22 single-chain Fv fragment for targeting non-Hodgkin's lymphoma," *Int. J. Cancer*, 107(5):822-829 (2003).
Ballmaier et al., "c-mpl mutations are the cause of congenital amegakaryocytic thrombocytopenia," *Blood*, 97:139-146 (2001).

(56) References Cited

OTHER PUBLICATIONS

Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Bowie et al., "Deciphering the Message in Protein Sequences: Tolerance to Amino Acid Substitutions," Science, 247:1306-1310 (1990).
Brinkmann et al., "FTY720: targeting G-protein-coupled receptors for sphingosine 1-phosphate in transplantation and autoimmunity," Curr. Opin. Immunol., 14:569-575 (2002).
Bruenke et al., "A recombinant bispecific single-chain Fv antibody against HLA class II and FcγRIII (CD16) triggers effective lysis of lymphoma cells," Br. J. Haematol., 125:167-179 (2004).
Casset et al., "A peptide mimetic of an anti-CD4 monoclonal antibody by rational design," Biochemical and Biophysical Research Communications, 307:198-205 (2003).
Cekaite et al., "Protein Arrays: A versatile toolbox for target identification and monitoring of immune mmune responses," Methods Mol. Biol., 360:335-348 (2007).
Chatellier et al., "Functional mapping of conserved residues located at the VL and VH domain interface of a Fab," J. Mol. Biol., 264(1):1-6 (1996).
Chen et al., "Selection and analysis of an optimized anti-VEGF antibody: crystal structure of an affinity-matured Fab in complex with antigen," Journal of Molecular Biology, 293:865-881 (1999).
Chowdhury et al., "Engineering scFvs for improved stability," Methods Mol. Biol., 207:237-54 (2003).
Clackson et al., "Making antibody fragments using phage display libraries," Nature, 352:624- 628 (1991).
Clark, "CD22, a B Cell-Specific Receptor, Mediates Adhesion and Signal Transduction," J. Immunol., 150:4715-4718 (1993).
Co et al., "A Humanized Antibody Specific for the Platelet Integrin gpIIb/IIIa," J. Immunol., 152:2968-2976 (1994).
Cochlovius et al., "Treatment of human B cell lymphoma xenografts with a CD3 x CD19 diabody and T cells," The Journal of Immunology, 165:888-895 (2000).
Creighton, T., "Protein folding," Biochem. J., 270(1):1-16 (1990).
Daniel et al., "Induction of Apoptosis in Human Lymphocytes by Human Anti-HLA Class I Antibodies," Transplantation, 75:1380-1386 (2003).
Davies et al., "Antibody VH domains as small recognition units," Biotechnology (N.Y.), 13(5):475-9 (1995).
De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).
De Jonge et al., "Production and Characterization of Bispecific Single-Chain Antibody Fragments," Mol. Immunol., 32:1405-1412 (1995).
Dejonge et al., "In vivo retargeting of T cell effector function by recombinant bispecific single chain Fv (anti-DC3 x anti-idiottype) induces long term survival of the murine BCL1 lymphoma model," J. Immunol., 161(3):1454-1461 (1998).
Denardo et al., "Anti-HLA-DR/anti-DOTA Diabody Construction in a Modular Gene Design Platform: Bispecific Antibodies for Pretargeted Radioimmunotherapy," Cancer Biother. Radiopharm., 16:525-535 (2001).
Deng et al., "An Agonist Murine Monoclonal Antibody to the Human c-Mpl Receptor Stimulates Megakaryocytopoiesis," Blood, 92:1981-1988 (1998).
Desplancq et al., "Multimerization behaviour of single chain Fv variants for the tumour-binding antibody B72.3," Protein Engineering, 7(8):1027-1033 (1994).
Dillon et al., "Structural and functional characterization of disulfide isoforms of the human IgG2 subclass," J. Biol. Chem., 283(23):16206-15 (2008).
Ebert et al., "Expression of Metallothionein II in Intestinal Metaplasia, Dysplasia, and Gastric Cancer," Cancer Res., 60:1995-2001 (2000).

Eijsink et al., "Rational engineering of enzyme stability," Journal of Biotechnology, 113:105-120 (2004).
Elliott et al., "Activation of the Erythropoietin (EPO) Receptor by Bivalent Anti-EPO Receptor Antibodies," J. Biol. Chem., 271:24691-24697 (1996).
Ewert et al., "Biophysical properties of human antibody variable domains," J. Mol. Biol., 325:531-553 (2003).
Ewert et al., "Structure-based improvement of the biophysical properties of immunoglobulin $V_H$ domains with a generalizable approach," Biochemistry, 42:1517-1528 (2003).
Fayen et al., "Negative signaling by anti-HLA class I antibodies is dependent upon two triggering events," Int. Immunol., 10:1347-1358 (1998).
Funaro et al., "Monoclonal antibodies and therapy of human cancers," Biotechnol. Adv., 18:385-401 (2000).
Genestier et al., "Caspase-dependent Ceramide Production in Fas- and HLA Class I-mediated Peripheral T Cell Apoptosis," J. Biol. Chem., 273:5060-5066 (1998).
Genestier et al., "Antibodies to HLA Class 1 α1 Domain Trigger Apoptosis of CD40-Activated Human B Lymphocytes," Blood, 90:726-735 (1997).
Genestier et al., "Fas-Independent Apoptosis of Activated T Cells Induced by Antibodies to the HLA Class I α1 Domain," Blood, 90:3629-3639 (1997).
Genestier et al., "T cell sensitivity to HLA class I-mediated apoptosis is dependent on interleukin-2 and interleukin-4," Eur. J. Immunol., 27:495-499 (1997).
Ghetie et al., "Homodimerization of tumor-reactive monoclonal antibodies markedly increases their ability to induce growth arrest or apoptosis of tumor cells," Proc. Natl. Acad. Sci. USA, 94:7509-7514 (1997).
Goding, "Monoclonal Antibodies: Principles and Practice," Academic Press, second Ed., 125:129 (1986).
Goel et al., "$^{99m}$Tc-Labeled Divalent and Tetravalent CC49 Single-Chain Fv's: Novel Imaging Agents for Rapid In Vivo Localization of Human Colon Carcinoma," J. Nucl. Med., 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," Cancer Res., 60:6964-6971 (2000).
Goldstein et al., "Cytolytic and Cytostatic Properties of an Anti-Human FcγRI (CD64) x Epidermal Growth Factor Bispecific Fusion Protein," J. Immunol., 158:872-879 (1997).
Goto et al., "A Novel Membrane Antigen Selectively Expressed on Terminally Differentiated Human B Cells," Blood, 84:1922-1930 (1994).
Gruber et al., "Efficient tumor cell lysis mediated by a bispecific single chain antibody expressed in Escherichia coli," Journal of Immunology, 152:5368-5374 (1994).
Hanson et al., "Catalytic antibodies and their applications," Curr. Opin. Biotechnol., 16:631-636 (2005).
Holliger et al., "'Diabodies': Small bivalent and bispecific antibody fragments," Proc. Natl. Acad. Sci. USA, 90:6444-6448 (1993).
Hoogenboom et al., "Multi-subunit proteins on the surface of filamentous phage: methodologies for displaying antibody (Fab) heavy and light chains," Nucleic Acids Res., 19:4133-4137 (1991).
Hozumi and Tonegawa, "Evidence for somatic rearrangement of immunoglobulin genes coding for variable and constant regions," Proc. Natl. Acad. Sci. USA, 73(10):3628-3632 (1976).
Hu et al., "Minibody: A Novel Engineered Anti-Carcinoembryonic Antigen Antibody Fragment (Single-Chain Fv-$C_H$3) Which Exhibits Rapid, High-Level Targeting of Xenografts," Cancer Res., 56:3055-3061 (1996).
Hudson et al., "High avidity scFv multimers; diabodies and triabodies," J. Immunol. Methods, 231:177-189 (1999).
Ito et al., "The His-probe method: effects of histidine residues introduced into the complementarity-determining regions of antibodies on antigen-antibody interactions at different pH values," FEBS Lett., 309:85-88 (1992).
Jäger et al., "Folding and assembly of an antibody Fv fragment, a heterodimer stabilized by antigen," Journal of Molecular Biology, 285:2005-2019 (1999).

(56) References Cited

OTHER PUBLICATIONS

Jung et al., "The importance of framework residues H6, H7 and H10 in antibody heavy chains: experimental evidence for a new structural subclassification of antibody V(H) domains," *J. Mol. Biol.*, 309(3):701-16 (2001).
Khalifa et al., "Effects on interaction kinetics of mutations at the VH-VL interface of Fabs depend on the structural context," *J. Mol. Recognit.*, 13(3):127-39 (2000).
Kikuchi et al., "A bivalent single-chain Fv fragment against CD47 induces apoptosis for leukemic cells," *Biochem. Biophys. Res. Commun.*, 315:912-918 (2004).
Kimura et al., "2D7 diabody bound to the α2 domain of HLA class I efficiently induces caspase-independent cell death against malignant and activated lymphoid cells," *Biochem. Biophys. Res. Commun.*, 325:1201-1209 (2004).
Kipriyanov and Little, "Generation of Recombinant Antibodies," *Molecular Biotechnology*, 12:173-201 (1999).
Kipriyanov et al., "Bispecific CD3 x CD19 diabody for T cell-mediated lysis of malignant human B cells," *In. J. Cancer*, 77:763-772 (1998).
Kipriyanov et al., "Bispecific tandem diabody for tumor therapy with imprived antigen binding and pharmacokinetics," *Journal of Molecular Biology*, 293:41-56 (1999).
Kipriyanov et al., "Effect of Domain Order on the Activity of Bacterially Produced Bispecific Single-chain Fv Antibodies," *J. Mol. Biol.*, 330:99-111 (2003).
Kong et al., "A Single Residue, Aspartic Acid 95, in the δ Opioid Receptor Specifies Selective High Affinity Agonist Binding," *The Journal of Biological Chemistry*, 268(31):23056-23058 (1993).
Kontermann, R., "Recombinant bispecific antibodies for cancer therapy," *Acta Pharmacol. Sin.*, 26(1):1-9 (2005).
Korn et al., "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).
Kortt et al., "Dimeric and trimeric antibodies: high avidity scFvs for cancer targeting," *Biomol. Eng.*, 18:95-108 (2001).
Krebber et al., "Reliable cloning of functional antibody variable domains from hybridomas and spleen cell repertoires employing a reengineered phage display system," *J. Immunol. Methods*, 201:35-55 (1997).
Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," *Clin. Cancer Res.*, 6:1476-1487 (2000).
Kriangkum et al., "Bispecific and bifunctional single chain recombinant antibodies," *Biomol. Eng.*, 18(2):31-40 (2001).
Kulkarni et al., "Construction of a Single-Chain Antibody Derived From 5H7, A Monoclonal Antibody Specific for a Death Signaling Domain of Human Class I Major Histocompatibility Complex," *Transplant. Proc.*, 30:1081 (1998).
Kulkarni et al., "Programmed Cell Death Signaling Via Cell-Surface Expression of a Single-Chain Antibody Transgene," *Transplantation*, 69:1209-1217 (2000).
Kumar et al., "Molecular cloning and expression of the fabs of human autoantibodies in *Escherichia coli*," *The Journal of Biological Chemistry*, 275(41):35129-35136 (2000).
Kumar et al., "The second PDZ domain of INAD is a type I domain involved in binding to eye protein kinase C. Mutational analysis and naturally occuring variants," *J. Biol. Chem.*, 276(27):24971-24977 (2001).
Kurucz et al., "Retargeting of CTL by an efficiently refolded bispecific single-chain Fv dimer produced in bacteria," *The Journal of Immunology*, 154:4576-4582 (1995).
Le Gall et al., "Effect of linker sequences between the antibody variable domains on the formation, stability and biological activity of a bispecific tandem diabody," *Protein Engineering Design & Selection*, 17(4):357-366 (2004).

Lebrun et al., "Antibodies to the Extracellular Receptor Domain Restore the Hormone-insensitive Kinase and Conformation of the Mutant Insulin Receptor Valine 382," *J. Biol. Chem.*, 268:11272-11277 (1993).
Ledbetter et al., "Agonistic Activity of a CD40-Specific Single-Chain Fv Constructed from the Variable Regions of mAb G28-5," *Critical Reviews in Immunology*, 17:427-435 (1997).
Li et al., "The Epitope Specificity and Tissue Reactivity of Four Murine Monoclonal Anti-CD22 Antibodies," *Cell. Immunol.*, 118:85-99 (1989).
Little et al., "Of mice and men: hybridoma and recombinant antibodies," *Immunol. Today*, 21:364-370 (2000).
Liu et al., "Functional interactions between arginine-133 and aspartate-88 in the human reduced folate carrier: evidence for a charge-pair association," *Biochem. J.*, 358:511-516 (2001).
Lund et al., "Expression and characterization of truncated forms of humanized L243 IgG1. Architectural features can influence synthesis of its oligosaccharide chains and affect superoxide production triggered through human Fcgamma receptor I," *Eur. J. Biochem.*, 267(24):7246-57 (2000).
Mack et al., "A small bispecific antibody construct expressed as a functional single-chain molecule with high tumor cell cytotoxicity," *Proc. Natl. Acad. Sci. USA*, 92(15):7021-7025 (1995).
Maity et al., "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).
Mallender et al., "Construction, expression and activity of a bivalent bispecific single-chain antibody," *J. Biol. Chem.*, 269(1):199-206 (1994).
Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," *J. Exp. Med.*, 198:497-503 (2003).
Matsuoka et al., "A Novel Type of Cell Death of Lymphocytes Induced by a Monoclonal Antibody without Participation of Complement," *J. Exp. Med.*, 181:2007-2015 (1995).
McGuinness et al., "Phage diabody repertoires for selection of large number of bispecific antibody fragments," *Nature Biotechnology*, 14(9):1149-1154 (1996).
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Meng et al., "The evaluation of recombinant, chimeric, tetravalent antihuman CD22 antibodies," *Clinical Cancer Research*, 10:1274-1281 (2004).
Moore et al., "Kinetics and thermodynamics of dimer formation and dissociation for a recombinant humanized monoclonal antibody to vascular endothelial growth factor," *Biochemistry*, 38:13960-13967 (1999).
Ngo et al., "Computational Complexity, Protein Structure Prediction, and the Levinthal Paradox ," *The Protein Folding Problem and Tertiary Structure Prediction*, Merz, Jr. et al. Editors, Birkhauser Boston, 433-506 (1994).
Nieba et al., "Disrupting the hydrophobic patches at the antibody variable/constant domain interface: improved in vivo folding and physical characterization of an engineered scFv fragment," *Protein Engineering*, 10(4):435-444 (1997).
Nishii, "CD22 antibody therapy," *Current Therapy*, 20:47-50 (2001) (English translation included).
Nohaile et al., "Altering dimerization specificity by changes in surface electrostatics," *PNAS* 98(6):3109-3114 (2001).
Ohtomo et al., "Molecular Cloning and Characterization of a Surface Antigen Preferentially Overexpressed on Multiple Myeloma Cells," *Biochem. Biophys. Res. Commun.*, 258:583-591 (1999).
Oka, "Development of Novel Immunotoxin Using Recombinant Alpha-Sarcin and Its Application Treatment of Hematopoietic Tumor," *Sankyo Seimei Kagaku Kenkyu Shinko Zaidan Kenkyu Hokokushu*, 12:46-56 (1998) (English translation included).

(56) References Cited

OTHER PUBLICATIONS

Ono et al., "The humanized anti-HM1.24 antibody effectively kills multiple myeloma cells by human effector cell-mediated cytotoxicity," *Mol. Immunol.*, 36:387-395 (1999).

Orita et al., "A novel therapeutic approach for thrombocytopenia by minibody agonist of the thrombopoietin receptor," *Blood*, 105:562-566 (2005).

Ozaki et al., "A Recombinant HLA Class I-Specific Single Chain Fv Diabody Induces Cell Death in Human Lymphoid Malignancies," *Blood*, 102:933a, Abstract No. 3474 (2003).

Ozaki et al., "Humanized Anti-HM1.24 Antibody Mediates Myeloma Cell Cytotoxicity That Is Enhanced by Cytokine Stimulation of Effector Cells," *Blood*, 93:3922-3930 (1999).

Ozaki et al., "Immunotherapy of Multiple Myeloma With a Monoclonal Antibody Directed Against a Plasma Cell-Specific Antigen, HM1.24," *Blood*, 90:3179-3186 (1997).

Palacios et al., "IL-3-dependent mouse clones that express B-220 surface antigen, contain Ig genes in germ-line configuration, and generate B lymphocutes in vivo," *Cell*, 41:727-734 (1985).

Peipp et al., "Bispecific antibodies targeting cancer cells," *Biochem. Soc. Trans.*, 30:507-511 (2002).

Pettersen et al., "The TCR-Binding Region of the HLA Class I $\alpha_2$ Domain Signals Rapid Fas-Independent Cell Death: A Direct Pathway for T Cell-Mediated Killing of Target Cells?" *J. Immunol.*, 160:4343-4352 (1998).

Piétri-Rouxel et al., "The biochemical effect of the naturally occurring Trp64→Arg mutation on human β3-adrenoceptor activity," *Eur. J. Biochem.*, 247:1174-1179 (1997).

Plückthun et al., "New protein engineering approaches to multivalent and bispecific antibody fragments," *Immunotechnology*, 3:83-105 (1997).

Rajagopal et al., "A form of anti-Tac (Fv) which is both single-chain and disulfide stabilized: comparison with its single-chain and disulfide-stabilized homologs," *Protein Engineering*, 10(12):1453-1459 (1997).

Rathanaswami et al., "Demonstration of an in vivo generated sub-picomolar affinity fully human monoclonal antibody to interleukin-8," Biochem. Biophys. Res. Commun., 334:1004-13 (2005).

Ridgway et al., "'Knobs-into-holes' engineering of antibody $C_H3$ domains for heavy chain heterodimerization," *Protein Eng.*, 9:617-621 (1996).

Rossi et al., "Development of New Multivalent-bispecific Agents for Pretargeting Tumor Localization and Therapy," *Clin. Cancer Res.*, 9:3886s-3896s (2003).

Rousch et al., "Somatostatin displayed on filamentous phage as a receptor-specific agonist," *Br. J. Pharmacol.*, 125:5-16 (1998).

Sal-Man et al., "Arginine mutations within a transmembrane domain of Tar, an *Escherichia coli* aspartate receptor, can drive monodimer dissociation and heterodimer association n vivo," *Biochem. J.*, 385(1):29-36 (2005).

Sato et al., "CD22 Is Both a Positive and Negative Regulator of B Lymphocyte Antigen Receptor Signal Transduction: Altered Signaling in CD22-Deficient Mice," *Immunity*, 5:551-562 (1996).

Scheurle et al., "Cancer Gene Discovery Using Digital Differential Display," *Cancer Res.*, 60:4037-4043 (2000).

Schmidt et al., *Human Physiology*, Moscow, 2:431-436 (1996), and English translation: Schmidt et al., "Hemostatis and Coagulation," *Human Physiology*, R.F. Schmidt, G. Thews (Eds.), Second, Completely Revised Edition, 418-423 [translated by Marguerite A. Biederman-Thorson], Springer-Verlag, 1989.

Schmidt et al., *Human Physiology*, Moscow, 3:764 (1996), and English translation: Schmidt et al., "Enzymes of the pancreatic juice," *Human Physiology*, R.F. Schmidt, G. Thews (Eds.), Second, Completely Revised Edition, 716 [translated by Marguerite A. Biederman-Thorson], Springer-Verlag, 1989.

Shalaby et al., "Development of Humanized Bispecific Antibodies Reactive with Cytotoxic Lymphocytes and Tumor Cells Overexpressing the HER2 Protooncogene," *J. Exp. Med.*, 175:217-225 (1992).

Shimba et al., "Comparative thermodynamic analyses of the Fv, Fab* and Fab fragments of anti-dansyl mouse monoclonal antibody," *FEBS Letters*, 360:247-250 (1995).

Shire et al., "Challenges in the development of high protein concentration formulations," *Journal of Pharmaceutical Sciences*, 93(6):1390-1402 (2004).

Skerra, "Use of the tetracycline promoter for the tightly regulated production of a murine antibody fragment in *Escherichia coli*," *Gene*, 151:131-135 (1994).

Smith et al, "Inhibition of T Cell Activation by a Monoclonal Antibody Reactive Against the α3 Domain of Human MHC Class I Molecules," *J. Immunol.*, 153:1054-1067 (1994).

Smith-Gill et al., "Contributions of immunoglobulin heavy and light chains to antibody specificity for lysozyme and two haptens," *The Journal of Immunology*, 139:4135-4144 (1987).

Song et al., "Light chain of natural antibody plays a dominant role in protein antigen binding," *Biochemical and Biophysical Research Communications*, 268:390-394 (2000).

Souyri, M., "Mpl: from an acute myeloproliferative virus to the isolation of the long sought thrombopoietin," *Seminars in Hematology*, 35(3):222-231 (1998).

Tahtis et al., "Biodistribution Properties of [111]Indium-labeled C-Functionalized trans-Cyclohexyl Diethylenetriaminepentaacetic Acid Humanized 3S193 Diabody and F(ab')$_2$ Constructs in a Breast Carcinoma Xenograft Model," *Clin. Cancer Res.*, 7:1061-1072 (2001).

Tan et al., "Contributions of a highly conserved $V_H/V_L$ hydrogen bonding interaction to scFv folding stability and refolding efficiency," *Biophysical Journal*, 75:1473-1482 (1998).

Tang et al., "Selection of linkers for a catalytic single-chain antibody using phage display technology", *The Journal of Biological Chemistry*, 271(26):15682-15686 (1996).

Tedder et al., "CD22, a B Lymphocyte-Specific Adhesion Molecule That Regulates Antigen Receptor Signaling," *Annu. Rev. Immunol.*, 15:481-504 (1997).

Thilenius et al., "Agonist antibody and Fas ligand mediate different sensitivity to death in the signaling pathways of Fas and cytoplasmic mutants," *Eur. J. Immunol.*, 27:1108-1114 (1997).

Turner et al., "Importance of the linker in expression of single-chain Fv antibody fragments: optimization of peptide sequence using phage display technology," *Journal of Immunological Methods*, 205:43-54 (1997).

Van Den Burg et al., "Selection of mutations for increased protein stability," *Curr. Opin. Biotechnol.*, 13(4):333-337 (2002).

Vargas-Madrazo et al., "An improved model of association for VH-VL immunoglobulin domains: asymmetries between VH and VL in the packing of some interface residues," *J. Mol. Recognit.*, 16(3):113-20 (2003).

Vieille et al., "Hyperthermophilic enzymes: sources, uses, and molecular mechanisms for thermostability," *Microbiology and Molecular Biology Reviews*, 65(1):1-43 (2001).

Volkel et al., "Optimized linker sequences for the expression of monomeric and dimeric bispecific single-chain diabodies," *Protein Engineering*, 14(10):815-823 (2001).

Wells, "Perspectives in Biochemistry," *Biochemistry*, 29(37):8509-8517 (1990).

Whitlow et al., "An improved linker for single-chain Fv with reduced aggregation and enhanced proteolytic stability," *Protein Engineering*, 6(8):989-995 (1993).

Woodle et al., "Anti-Human Class I MHC Antibodies Induce Apoptosis by a Pathway That Is Distinct from the Fas Antigen-Mediated Pathway," *J. Immunol.*, 158:2156-2164 (1997).

Woodle et al., "Anti-Human Class I α3 Domain-Specific Monoclonal Antibody Induces Programmed Cell Death in Murine Cells Expressing Human Class I MHC Transgenes," *Transplant. Proc.*, 30:1059-1060 (1998).

Woodle et al., "Class I MHC Mediates Programmed Cell Death in Human Lymphoid Cells," *Transplantation*, 64:140-146 (1997).

Worn et al., "Stability engineering of antibody single-chain Fv fragments," *J. Mol. Biol.*, 305:989-1010 (2001).

(56) References Cited

OTHER PUBLICATIONS

Wu et al., "Development of motavizumab, an ultra-potent antibody for the prevention of respiratory syncytial virus infection in the upper and lower respiratory tract," *J. Mol. Biol.*, 368(3):652-65 (2007).
Wu et al., "Multimerization of a chimeric anti-CD20 single-chain Fv-Fc fusion protein is mediated through variable domain exchange," *Protein Eng.*, 14(12):1025-33 (2001).
Wu et al., "Tumor localization of anti-CEA single-chain Fvs: improved targeting by non-covalent dimers," *Immunotechnology*, 2:21-36 (1996).
Xiong et al., "Efficient inhibition of human B-cell lymphoma xenografts with an anti-CD20 X anti-CD3 bispecific diabody," *Cancer Lett.*, 177:29-39 (2002).
Xu et al., "Insight into hepatocellular carcinogenesis at transcriptome level by comparing gene expression profiles of hepatocellular carcinoma with those of corresponding noncancerous liver," *Proc. Natl. Acad. Sci. USA*, 98:15089-15094 (2001).
Zhu et al., "An efficient route to the production of an IgG-like bispecific antibody", Protein Eng., 13:361-367 (2000).
Zhu et al., "Remodeling domain interfaces to enhance heterodimer formation," *Protein Science*, 6:781-788 (1997).
International Search Report for App. Ser. No. PCT/US2006/306803, mailed Jul. 11, 2006, 4 pages.
International Preliminary Report on Patentability for App. Ser. No. PCT/US2006/306803, dated Oct. 3, 2007, 6 pages.
International Search Report for App. Ser. No. PCT/JP2008/067534, mailed Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, mailed Jul. 7, 2009, 8 pages.
International Preliminary Report on Patentability for App. Ser. No. PCT/JP2009/057309, mailed Nov. 30, 2010, 7 pages.
USPTO Restriction Requirement in U.S. Appl. No. 12/295,039, dated Oct. 12, 2010, 9 pages.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
Fish & Richardson P.C., Amendment in Reply to Action dated Jun. 23, 2010 in U.S. Appl. No. 10/575,193, filed Dec. 22, 2010, 13 pages.
USPTO Notice of Allowance in U.S. Appl. No. 10/575,193, mailed Mar. 18, 2011, 11 pages.
USPTO Restriction Requirement in U.S. Appl. No. 11/910,836, dated Mar. 18, 2011, 7 pages.
USPTO Non-Final Office Action in U.S. Appl. No. 11/910,836, dated Sep. 30, 2011, 21 pages.
Igawa et al., "Engineering the variable region of therapeutic IgG antibodies," *MAbs*, 3(3):243-52 (2011).
Igawa et al., "Reduced elimination of IgG antibodies by engineering the variable region," *Protein Eng. Des. Sel.*, 23(5):385-92 (2010).
Maeda et al., "pH-dependent receptor/ligand dissociation as a determining factor for intracellular sorting of ligands for epidermal growth factor receptors in rat hepatocytes," *J. Control Release*, 82(1):71-82 (2002).
Maxfield et al., "Endocytic recycling," *Nat. Rev. Mol. Cell Biol.*, 5(2):121-32 (2004).
Murtaugh et al., "A combinatorial histidine scanning library approach to engineer highly pH-dependent protein switches," *Protein Sci.*, 20(9):1619-31 doi:10.1002/pro 696 (2011).
European Search Report for App. Ser. No. EP 09 72 9337, dated Nov. 3, 2011, 3 pages.
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Almagro et al., "Humanization of antibodies," *Front Biosci.*, 13:1619-33 (2008).
Arndt et al., "Helix-stabilized Fv (hsFv) antibody fragments: substituting the constant domains of a Fab fragment for a heterodimeric coiled-coil domain," *J. Mol. Biol.*, 312:221-228 (2001).
Armour et al., "Recombinant human IgG molecules lacking Fcgamma receptor I binding and monocyte triggering activities," *Eur. J. Immunol.*, 29(8):2613-24 (1999).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al., "Immunogenicity, efficacy and adverse events of adalimumab in RA patients," *Rheumatol. Int.*, 27:269-274 (2007).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chen et al., "Generation and analysis of random point mutations in an antibody CDR2 sequence: many mutated antibodies lose their ability to bind antigen," *J. Exp. Med.*, 176(3):855-66 (1992).
Chen et al., "Defective secretion of an immunoglobulin caused by mutations in the heavy chain complementarity determining region 2," *J. Exp. Med.*, 180(2):577-86 (1994).
Chirino et al., "Minimizing the immunogenicity of protein therapeutics," *Drug Discov. Today.*, 9:82-90 (2004).
Chu et al., "Accumulation of succinimide in a recombinant monoclonal antibody in mildly acidic buffers under elevated temperatures," *Pharm. Res.*, 24(6):1145-56 (2007).
Cole et al., "Human IgG2 variants of chimeric anti-CD3 are nonmitogenic to T cells," *J. Immunol.*, 159(7):3613-21 (1997).
Cordoba et al., "Non-enzymatic hinge region fragmentation of antibodies in solution," *J. Chromatogr. B. Analyt. Technol. Biomed. Life Sci.*, 818(2):115-21 (2005).
Dall'Acqua et al., "Antibody humanization by framework shuffling," *Methods*, 36(1):43-60 (2005).
Damschroder et al., "Framework shuffling of antibodies to reduce immunogenicity and manipulate functional and biophysical properties," *Mol. Immunol.*, 44(11):3049-60 (2007).
De Groot et al., "De-immunization of therapeutic proteins by T-cell epitope modification," *Dev. Biol. (Basel)*, 122:171-94 (2005).
Fujii, "Antibody affinity maturation by random mutagenesis," *Methods Mol. Biol.*, 248:345-59 (2004).
Gelderman et al., "The inhibitory effect of CD46, CD55, and CD59 on complement activation after immunotherapeutic treatment of cervical carcinoma cells with monoclonal antibodies or bispecific monoclonal antibodies," *Lab Invest.*, 82(4):483-93 (2002).
Gerstner et al., "Sequence plasticity in the antigen-binding site of a therapeutic anti-HER2 antibody," *J. Mol. Biol.*, 321(5):851-62 (2002).
Gessner et al., "The IgG Fc receptor family," *Ann. Hematol.*, 76:231-248 (1998).
Guyre et al., "Increased potency of Fc-receptor-targeted antigens," *Cancer Immunol. Immunother.*, 45(3-4):146-8 (1997).
Hinton et al., "Engineered human IgG antibodies with longer serum half-lives in primates," *J. Biol. Chem.*, 279(8):6213-6 (2004).
Hwang et al., "Use of human germline genes in a CDR homology-based approach to antibody humanization," Methods, 36:35-42 (2005).
Johnson et al., "Cation exchange-HPLC and mass spectrometry reveal C-terminal amidation of an IgG1 heavy chain," *Anal. Biochem.*, 360:75-83 (2007).
Jones et al., "Identification and removal of a promiscuous CD4+ T cell epitope from the C1 domain of factor VIII," *Thromb. Haemost.*, 3:991-1000 (2005).
Katayose et al., "MUC1-specific targeting immunotherapy with bispecific antibodies: inhibition of xenografted human bile duct carcinoma growth," *Cancer Res.*, 56(18):4205-12 (1996).
Komissarov et al., "Site-specific mutagenesis of a recombinant anti-single-stranded DNA Fab. Role of heavy chain complementar-

(56) References Cited

OTHER PUBLICATIONS ity-determining region 3 residues in antigen interaction," *J. Biol. Chem.*, 272(43):26864-70 (1997).
Kurfis et al., "Role of Arg182 in the second extracellular loop of angiotensin II receptor AT2 in ligand binding," *Biochem. Biophys. Res. Commun.*, 263:816-819 (1999).
Leong et al., "Adapting pharmacokinetic properties of a humanized anti-interleukin-8 antibody for therapeutic applications using site-specific pegylation," *Cytokine*, 16(3):106-19 (2001).
Liu et al., "Heterogeneity of monoclonal antibodies," *J. Pharm. Sci.*, 97(7):2426-47 (2008).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Martinez et al., "Disulfide connectivity of human immunoglobulin G2 structural isoforms," *Biochemistry*, 47(28):7496-7508 (2008).
Nesterova et al., "Glypican-3 as a novel target for an antibody-drug conjugate," AACR Abstract No. 656, Los Angeles, CA (Apr. 4-18, 2007).
Nishimoto et al., "Humanized anti-interleukin-6 receptor antibody treatment of multicentric Castleman disease," *Blood*, 106:2627-32 (2005).
Nishimoto et al., "Interleukin 6: from bench to bedside," *Nat. Clin. Pract. Rheumatol.*, 2:619-626 (2006).
Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).
Pons et al., "Energetic analysis of an antigen/antibody interface: alanine scanning mutagenesis and double mutant cycles on the HyHEL-10/lysozyme interaction," *Protein Sci.*, 8(5):958-68 (1999).
Presta, "Engineering of therapeutic antibodies to minimize immunogenicity and optimize function," *Adv. Drug Deliv. Rev.*, 58(5-6):640-56 (2006).
Raffen et al., "Reengineering immunoglobulin domain interactions by introduction of charged residues," *Protein Eng.* ,11:303-309 (1998).
Reddy et al., "Elimination of Fc receptor-dependent effector functions of a modified IgG4 monoclonal antibody to human CD4," *J. Immunol.*, 164(4):1925-33 (2000).
Reichert et al., "Development trends for monoclonal antibody cancer therapeutics," *Nat. Rev. Drug Discov.*, 6(5):349-56 (2007).
Rothe et al., "Ribosome display for improved biotherapeutic molecules," *Expert Opin. Biol. Ther.*, 6:177-187 (2006).
Salfeld et al., "Isotype selection in antibody engineering," *Nat. Biotechnol.*, 25:1369-72 (2007).
Sato et al., "Reshaping a human antibody to inhibit the interleukin 6-dependent tumor cell growth," *Cancer Res.*, 53:851-856 (1993).
Schmitz et al., "Phage display: a molecular tool for the generation of antibodies—a review," *Placenta.*, 21 Suppl A:S106-12 (2000).
Sinha et al., "Electrostatics in protein binding and function," *Curr. Protein Pept. Sci.*, 3(6):601-14 (2002).
Sinha et al., "Molecular dynamics simulation of a high-affinity antibody-protein complex: the binding site is a mosaic of locally flexible and preorganized rigid regions," *Cell Biochem Biophys.*, 43:253-273 (2005).
Strand et al., "Biologic therapies in rheumatology: lessons learned, future directions," *Nat. Rev. Drug Discov.*, 6:75-92 (2007).
Tan et al., "Engineering the isoelectric point of a renal cell carcinoma targeting antibody greatly enhances scFv solubility," *Immunotechnology*, 4(2):107-114 (1998).
Teeling et al., "The biological activity of human CD20 monoclonal antibodies is linked to unique epitopes on CD20," *J. Immunol.*, 177(1):362-71 (2006).
Tsuchiya, Credit Suisse Seminar, "Therapeutic Antibody," at Fuji-Gotemba Laboratories, p. 21 (2006) [English translation].
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Van Walle et al., "Immunogenicity screening in protein drug development," *Expert Opin. Biol. Ther.*, 7(3):405-18 (2007).
Wiens et al., "Somatic mutation in VH complementarity-determining region 2 and framework region 2: differential effects on antigen binding and Ig secretion," *J. Immunol.*, 159(3):1293-302 (1997).
Wiens et al., "Mutation of a single conserved residue in VH complementarity-determining region 2 results in a severe Ig secretion defect," *J. Immunol.*, 167(4):2179-86 (2001).
Wypych et al., "Human IgG2 antibodies display disulfide-mediated structural isoforms," *J. Biol. Chem.*, 283(23):16194-16205 (2008).
Xiang et al., "Study of B72.3 combining sites by molecular modeling and site-directed mutagenesis," *Protein Eng.*, 13(5):339-44 (2000).
Zwick et al., "The long third complementarity-determining region of the heavy chain is important in the activity of the broadly neutralizing anti-human immunodeficiency virus type 1 antibody 2F5," *J. Virol.*, 78(6):3155-61 (2004).
Fish & Richardson P.C., Response to Restriction Requirement dated Jun. 9, 2011 in U.S. Appl. No. 11/910,128, filed Dec. 2, 2011, 1 page.
USPTO Restriction Requirement in U.S. Appl. No. 10/560,098, mailed Jul. 13, 2007, 9 pages.
Fish & Richardson P.C., Response to Restriction Requirement dated Jul. 13, 2007 in U.S. Appl. No. 10/560,098, filed Aug. 10, 2007, 6 pages.
USPTO Non-Final Office Action in U.S. Appl. No. 10/560,098, mailed Oct. 23, 2007, 17 pages.
USPTO Final Office Action in U.S. Appl. No. 10/560,098, mailed Sep. 11, 2008, 20 pages.
USPTO Interview Summary for U.S. Appl. No. 10/560,098, mailed Jun. 5, 2009, 8 pages.
Fish & Richardson P.C., Amendment in Reply to Office Action dated Sep. 11, 2008 in U.S. Appl. No. 10/560,098, filed Jun. 10, 2009, 12 pages.
USPTO Office Action in U.S. Appl. No. 10/560,098, mailed Aug. 13, 2009, 21 pages.
Fish & Richardson P.C., Amendment in Reply to Office Action dated Aug. 13, 2009 in U.S. Appl. No. 10/560,098, filed Feb. 16, 2010, 14 pages.
USPTO Final Office Action in U.S. Appl. No. 10/560,098, mailed Jun. 3, 2010, 16 pages.
USPTO Non-Final Office Action in U.S. Appl. No. 10/560,098, mailed Dec. 8, 2011, 11 pages.
International Search Report for App. Ser. No. PCT/JP2004/008585, mailed Sep. 7, 2004, 4 pages.
International Preliminary Report on Patentability for App. Ser. No. PCT/JP2004/008585, dated Apr. 15, 2005, 16 pages.
Fish & Richardson P.C., Amendment in Reply to Office Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
USPTO Restriction Requirement in U.S. Appl. No. 12/936,587, dated Dec. 6, 2011, 7 pages.
USPTO Non-Final Office Action in U.S. Appl. No. 11/910,128, dated Apr. 25, 2012, 21 pages.
Wang et al., "Polyethylene Glycol-modified Chimeric Toxin Composed of Transforming Growth Factor alpha and *Pseudomonas* Exotoxin," *Cancer. Res.*, 53:4588-4594 (1993).
Fish & Richardson P.C., Amendment in Reply to Non-Final Office Action dated Dec. 8, 2011 in U.S. Appl. No. 10/560,098, filed Jun. 5, 2012, 11 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
USPTO Restriction Requirement in U.S. Appl. No. 12/680,082, dated Jun. 6, 2012, 12 pages.

(56) References Cited

OTHER PUBLICATIONS

Fish & Richardson P.C., Fourth Preliminary Amendment and Response to Restriction Requirement dated Jun. 6, 2012 in U.S. Appl. No. 12/680,082, filed Jun. 29, 2012, 13 pages.
International Search Report for App. Ser. No. PCT/JP2010/066490, mailed Nov. 9, 2010, 5 pages.
International Preliminary Report on Patentability for App. Ser. No. PCT/JP2010/066490, dated Apr. 11, 2012, 6 pages.
Amersham Biosciences, "Affinity Chromatography: Principles and Methods," Edition AD, pp. 16-18, 137 (2002).
Presta et al., "Molecular engineering and design of therapeutic antibodies," *Curr. Opin. Immunol.*, 20(4):460-70. doi: 10.1016/j.coi.2008.06.012 (2008).
Zhu et al., "MHC class I-related neonatal Fc receptor for IgG is functionally expressed in monocytes, intestinal macrophages, and dendritic cells," *J. Immunol.*, 166(5):3266-76 (2001).
USPTO Non-Final Office Action U.S. Appl. No. 12/680,082, dated Feb. 14, 2013, 12 pages.
Fish & Richardson P.C., Response to Restriction Requirement dated Jul. 27, 2012 and Preliminary Amendment in U.S. Appl. No. 13/434,643, filed Jan. 24, 2013, 12 pages.
USPTO Non-Final Office Action in U.S. Appl. No. 13/434,643, dated Feb. 12, 2013, 17 pages.
USPTO Restriction Requirement in U.S. Appl. No. 13/257,145, dated Mar. 20, 2013, 11 pages.
Allen et al., "Interchain disulfide bonding in human IgG2 antibodies probed by site-directed mutagenesis," *Biochemistry*, 48(17):3755-66 (2009).
USPTO Notice of Allowance in U.S. Appl. No. 10/560,098, dated Apr. 25, 2013, 12 pages.
Fish & Richardson P.C., Response to Restriction Requirement dated Dec. 6, 2012 in U.S. Appl. No. 13/497,269, filed May 1, 2013, 2 pages.
Fish & Richardson P.C., Preliminary Amendment and Response to Restriction Requirement dated Mar. 20, 2013 in U.S. Appl. No. 13/257,145, filed Apr. 22, 2013, 7 pages.
Fish & Richardson P.C., Amendment in Reply to Office Action dated Feb. 12, 2013 in U.S. Appl. No. 13/434,643, filed May 13, 2013, 18 pages.
U.S. Appl. No. 13/518,861, Igawa et al.
U.S. Appl. No. 13/582,073, Kuramochi et al.
Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).
Amersham Biosciences, "Protein Purification Handbook," Edition AC, 98 pages (2001).
Angal et al., "A single amino acid substitution abolishes the heterogeneity of chimeric mouse/human (IgG4) antibody," *Mol. Immunol.*, 30:105-108 (1993).
Atwell et al., "Stable heterodimers from remodeling the domain interface of a homodimer using a phage display library," *J. Mol. Biol.*, 270:26-35 (1997).
Bayry et al., "Immuno affinity purification of foot and mouth disease virus type specific antibodies using recombinant protein adsorbed to polystyrene wells," *J. Virol. Methods*, 81:21-30 (1999).
Brown et al., "Tolerance of single, but not multiple, amino acid replacements in antibody $V_H$ CDR2: a means of minimizing B cell wastage from somatic hypermutation?," *J. Immunol.*, 156(9):3285-91 (1996).
Burges et al., "Effective relief of malignant ascites in patients with advanced ovarian cancer by a trifunctional anti-EpCAM x anti-CD3 antibody: a phase I/II study," *Clin. Cancer Res.*, 13(13):3899-905 (2007).
Dall'Acqua et al., "Modulation of the effector functions of a human IgG1 through engineering of its hinge region," *J. Immunol.*, 177(2):1129-38 (2006).

Igawa et al., "Antibody recycling by engineered pH-dependent antigen binding improves the duration of antigen neutralization," *Nat. Biotechnol.*, 28(11):1203-7 (2010).
Jefferis et al., "Recognition sites on human IgG for Fc gamma receptors: the role of glycosylation," *Immunol. Lett.*, 44(2-3):111-7 (1995).
Kai et al., "Switching constant domains enhances agonist activities of antibodies to a thrombopoietin receptor," *Nat. Biotechnol.*, 26(2):209-11 (2008).
Kim et al., "Mapping the site on human IgG for binding of the MHC class I-related receptor, FcRn," *Eur. J. Immunol.*, 29(9):2819-25 (1999).
Kobayashi et al., "A monoclonal antibody specific for a distinct region of hen egg-white lysozyme," *Mol. Immunol.*, 19:619-30 (1982).
Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).
Lansdorp et al., "Purification and analysis of bispecific tetrameric antibody complexes," *Mol. Immunol.*, 27:659-666 (1990).
Life Technologies (Invitrogen: "ecdysone analogue" and pIND plasmid), Aug. 10, 2012, 2 pages.
MacCallum et al., "Antibody-antigen interactions: contact analysis and binding site topography," *J. Mol. Biol.*, 262:732-45 (1996).
Morell et al., "Metabolic properties of IgG subclasses in man," *J. Clin. Invest.*, 49(4):673-80 (1970).
Morimoto et al., "Single-step purification of F(ab')2 fragments of mouse monoclonal antibodies (immunoglobulins Gl) by hydrophobic interaction high performance liquid chromatography using TSKgel Phenyl-5PW," *J. Biochem. Biophys. Methods*, 24:107-117 (1992).
Ozhegov et al., Tolkovyi Slovar Russkogo iazyka: 2004, p. 292 (with an English translation of the relevant passage defining "control").
Queen et al., "A humanized antibody that binds to the interleukin 2 receptor," *Proc. Natl. Acad. Sci. U.S.A.*, 86(24):10029-10033 (1989).
Rudikoff et al., "Single amino acid substitution altering antigen-binding specificity," *Proc. Natl. Acad. Sci. U.S.A.*, 79(6):1979-83 (1982).
Ruf et al., "Pharmacokinetics and in vivo stability of intraperitoneally administered therapeutic antibody catumaxomab," *J. Clin. Oncol.*, 26 (May 20 suppl) (2008), abstr 14006.
Sarmay et al., "Mapping and comparison of the interaction sites on the Fc region of IgG responsible for triggering antibody dependent cellular cytotoxicity (ADCC) through different types of human Fc gamma receptor," *Mol. Immunol.*, 29(5):633-9 (1992).
Smith, "Creative Expression: Mammalian Expression Vectors and Systems," *The Scientist Magazine*, Feb. 2, 1998, 3 pages.
Sun et al., "Coexpression of Gas6/Ax1 in human ovarian cancers," *Oncology*, 66(6):450-7 (2004).
Suresh et al., "Bispecific monoclonal antibodies from hybrid hybridomas," *Methods Enzymol.*, 121:210-228 (1986).
Warnaar et al., "Purification of bispecific F(ab')2 from murine trinoma OC/TR with specificity for CD3 and ovarian cancer," *Hybridoma*, 13:519-526 (1994).
USPTO Final Office Action in U.S. Appl. No. 10/560,098, mailed Aug. 15, 2012, 10 pages.
Fish & Richardson P.C., Amendment in Reply to Final Office Action dated Aug. 15, 2012 in U.S. Appl. No. 10/560,098, filed Sep. 5, 2012, 8 pages.
USPTO Interview Summary in U.S. Appl. No. 10/560,098, mailed Sep. 7, 2012, 3 pages.
Fish & Richardson P.C., Response to Species Election Requirement dated Jun. 25, 2012 in U.S. Appl. No. 12/936,587, filed Jul. 25, 2012, 1 page.
USPTO Restriction Requirement in U.S. Appl. No. 13/434,643, dated Jul. 27, 2012, 6 pages.
Fish & Richardson P.C., Amendment in Reply to Action dated Apr. 12, 2012 in U.S. Appl. No. 12/295,039, filed Sep. 11, 2012, 12 pages.

(56) References Cited

OTHER PUBLICATIONS

USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
International Preliminary Report on Patentability for App. Ser. No. PCT/JP2010/073361, dated Aug. 14, 2012, 7 pages.
USPTO Non-Final Office Action in U.S. Appl. No. 12/936,587, dated Nov. 7, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
USPTO Non-Final Office Action in U.S. Appl. No. 13/595,139, dated Nov. 14, 2012, 10 pages.
International Search Report for App. Ser. No. PCT/JP2011/055101, mailed May 10, 2011, 4 pages.
USPTO Non-Final Office Action in U.S. Appl. No. 12/679,922, dated Jan. 3, 2013, 25 pages.
USPTO Restriction Requirement in U.S. Appl. No. 13/497,269, dated Dec. 6, 2012, 9 pages.
International Preliminary Report on Patentability for App. Ser. No. PCT/JP2011/055101, dated Oct. 2, 2012, 6 pages.
U.S. Appl. No. 13/885,421, filed Aug. 30, 2013, Igawa et al.
U.S. Appl. No. 13/990,088, filed May 29, 2013, Nezu et al.
U.S. Appl. No. 14/019,117, filed Sep. 5, 2013, Igawa et al.
U.S. Appl. No. 14/019,712, filed Sep. 6, 2013, Igawa et al.
Aslan et al., "Engineering a novel, stable dimeric streptavidin with lower isoelectric point," *J. Biotechnol.*, 128(2):213-25 (2007).
Baerga-Ortiz et al., "Two different proteins that compete for binding to thrombin have opposite kinetic and thermodynamic profiles," *Protein Sci.*, 13(1):166-76 (2004).
Baker et al., "Conversion of a T cell antagonist into an agonist by repairing a defect in the TCR/peptide/MHC interface: implications for TCR signaling," *Immunity*, 13:475-484 (2000).
Burgess, "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).
Dumont et al., "Monomeric Fc fusions: impact on pharmacokinetic and biological activity of protein therapeutics," *BioDrugs.*, 20(3):151-60 (2006).
Gunasekaran et al., "Enhancing antibody Fc heterodimer formation through electrostatic steering effects: applications to bispecific molecules and monovalent IgG," *J. Biol. Chem.*, 285(25):19637-46 (2010).
Jendeberg et al., "Engineering of Fc(1) and Fc(3) from human immunoglobulin G to analyse subclass specificity for staphylococcal protein A," *J. Immunol. Methods.*, 201(1):25-34 (1997).
Ju et al., "Conversion of the interleukin 1 receptor antagonist into an agonist by site-specific mutagenesis," *Proc. Natl. Acad. Sci. U.S.A.*, 88:2658-2662 (1991).
Lazar et al., "Transforming growth factor alpha: mutation of aspartic acid 47 and leucine 48 results in different biological activities," *Mol. Cell Biol.*, 8:1247-1252 (1988).
Marti et al., "Inverse electrostatic effect: electrostatic repulsion in the unfolded state stabilizes a leucine zipper," *Biochemistry*, 43(39):12436-47 (2004).
Pakula et al., "Genetic Analysis of Protein Stability and Function," *Annu. Rev. Genet.*, 23:289-310 (1989).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Van Loghem et al., "Staphylococcal protein A and human IgG subclasses and allotypes," *Scand. J. Immunol.*, 15(3):275-8 (1982).
USPTO Final Office Action in U.S. Appl. No. 11/910,128, dated Sep. 10, 2013, 12 pages.
USPTO Notice of Allowance in U.S. Appl. No. 10/560,098, dated Jul. 9, 2013, 6 pages.
Fish & Richardson P.C., Amendment in Reply to Non-Final Office Action dated Feb. 14, 2013 in U.S. Appl. No. 12/680,082, filed Aug. 12, 2013, 17 pages.
USPTO Final Office Action U.S. Appl. No. 12/680,082, dated Oct. 22, 2013, 12 pages.
USPTO Final Office Action in U.S. Appl. No. 13/434,643, dated Jul. 11, 2013, 19 pages.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 12/679,922, dated Aug. 2, 2013, 12 pages.
USPTO Non-Final Office Action in U.S. Appl. No. 13/497,269, dated Aug. 15, 2013, 13 pages.
USPTO Non-Final Office Action in U.S. Appl. No. 13/257,145, dated Jul. 2, 2013, 20 pages.
International Preliminary Report on Patentability for App. Ser. No. PCT/JP2011/077603, dated Jun. 4, 2013, 10 pages.
International Preliminary Report on Patentability for App. Ser. No. PCT/JP2011/076486, dated Jun. 12, 2013, 9 pages.
USPTO Restriction Requirement in U.S. Appl. No. 13/257,112, dated Oct. 15, 2013, 10 pages.
Kabat et al., Sequence of Proteins of Immunological Interest, 5$^{th}$ Edition 1991, p. 690 and p. 693.
Figini et al., "In vitro assembly of repertoires of antibody chains on the surface of phage by renaturation," *J Mol Biol.*, May 27, 1994;239(1):68-78.
Vaughan et al., "Human antibodies with sub-nanomolar affinities isolated from a large non-immunized phage display library," *Nat Biotechnol.*, Mar. 1996;14(3):309-14.
Wally et al., "Identification of a novel substitution in the constant region of a gene coding for an amyloidogenic kappa1 light chain," *Biochim Biophys Acta.*, May 31, 1999;1454(1):49-56.
Fish & Richardson P.C., Amendment in Reply to Action dated Jul. 28, 2014 in U.S. Appl. No. 12/679,922, filed Nov. 29, 2014, 23 pages.
Amann et al., "Therapeutic window of an EpCAM/CD3-specific BiTE antibody in mice is determined by a subpopulation of EpCAM-expressing lymphocytes that is absent in humans," *Cancer Immunol Immunother.*, Jan. 2009; 58(1):95-109. Epub Jul. 2, 2008.
Bargou et al., "Tumor regression in cancer patients by very low doses of a T cell-engaging antibody," *Science*, 321(5891):974-7 (2008).
Bokemeyer, "Catumaxomab—trifunctional anti-EpCAM antibody used to treat malignant ascites," *Expert Opin Biol Ther.*, 10(8):1259-69 (2010).
Campoli et al., "Immunotherapy of malignant disease with tumor antigen-specific monoclonal antibodies," *Clin Cancer Res.*, Jan. 1, 2010;16(1):11-20. Epub Dec. 22, 2009.
Dahlback, "Blood coagulation," *Lancet*, 355(9215):1627-32 (2000).
Datta-Mannan et al., "Monoclonal antibody clearance. Impact of modulating the interaction of IgG with the neonatal Fc receptor," *J Biol Chem.*, 282(3):1709-17 (2007).
Fay et al., "Chapter 2B Nonenzymatic cofactors: factor VIII," *Comprehensive Biochemistry*, 13:35-37 (1986).
Fay et al., "The size of human factor VIII heterodimers and the effects produced by thrombin," *Biochim Biophys Acta.*, 871(3):268-78 (1986).
Helfrich et al., "A rapid and versatile method for harnessing scFv antibody fragments with various biological effector functions," *J. Immunol. Methods*, 237(1-2):131-45 (2000).
Hoyer, L.W., "The factor VIII complex: structure and function," *Blood*, 58(1):1-13 (1981).
Hu et al., "Development and characterization of a novel fusion protein composed of a human 1gG1 heavy chain constant region and

(56) References Cited

OTHER PUBLICATIONS a single-chain fragment variable antibody against Venezuelan equine encephalitis virus," *J Biochem.*, 133(1):59-66 (2003).
Jackman et al., "Development of a two-part strategy to identify a therapeutic human bispecific antibody that inhibits IgE receptor signaling," *J Biol Chem.*, 285(27): 20850-9. doi: 10.1074/jbc.M110.113910. Epub May 5, 2010.
Jain et al., "Engineering antibodies for clinical applications," *Trends Biotechnol.*, 25(7):307-16 (2007).
Janeway et al., "Structure of the Antibody Molecule and Immunoglobulin Genes," *Immunobiology, 3rd Edition*, Garland Press, 3:1-3:11 (1997).
Kerschbaumer et al., "An antibody specific for coagulation factor IX enhances the activity of the intrinsic factor X-activating complex," *J. Biol. Chem.*, 279(39):40445-50 (2004).
Klein et al., "Progress in overcoming the chain association issue in bispecific heterodimeric IgG antibodies," *MAbs.*, Nov.-Dec. 2012;4(6):653-63. doi: 10.4161/mabs.21379. Epub Aug. 27, 2012.
Kufer et al., "A revival of bispecific antibodies," *Trends Biotechnol.*, 22(5):238-44 (2004).
Kumagai et al., "Humanized bispecific antibodies that recognize lymphocytes and cancer cells," *Drug Delivery System*, 23(5):518-25 (2008) (English translation).
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Lindsay, "Chapter 4: Determination of the Kinetics and Mechanism of tg-FIX Activation by Factor XIa," 49-75 (2004).
McEarchern et al., "Engineered anti-CD70 antibody with multiple effector functions exhibits in vitro and in vivo antitumor activities," *Blood*, Feb. 1, 2007;109(3):1185-92. Epub Oct. 12, 2006.
Mezzanzanica et al., "Human ovarian carcinoma lysis by cytotoxic T cells targeted by bispecific monoclonal antibodies: analysis of the antibody components," *Int J Cancer*, 41(4):609-15 (1988).
Miyazaki et al., "Generation of bispecific IgG, which mimics the cofactor function of blood coagulation factor VIII," *Seikagaku*, Poster sessions (2P-B-161) (2006).
Molhoj et al., "CD19-/CD3-bispecific antibody of the BiTE class is far superior to tandem diabody with respect to redirected tumor cell lysis," *Mol Immunol.*, 44(8):1935-43 (2007).
Nakano et al., "Anti-glypican 3 antibodies cause ADCC against human hepatocellular carcinoma cells," *Biochem Biophys Res Commun.*, Jan. 9, 2009;378(2):279-84. doi: 10.1016/j.bbrc.2008.11.033. Epub Nov. 18, 2008.
Natsume et al., "Improving effector functions of antibodies for cancer treatment: Enhancing ADCC and CDC," *Drug Des Devel Ther.*, 3:7-16 (2009).
Paul, William ed., *Fundamental Immunology, 3rd edition*, p. 242 (1993).
Paul, "Structure and function of immunoglobulins," Fundamental Immunology, Third Edition, 292-295 (1993).
Portolano et al., "Lack of Promiscuity in Autoantigen-Specific H and L Chain Combinations as Revealed by Human H and L Chain "Roulette"," *J. Immunol.*, 150(3):880-887 (1993).
Saito et al., "Factor VIII Mimetic Antibody: (1) Establishment and Characterization of Anti-factor IX/anti-factor X Bispecific Antibodies," *2005 International Society of Thrombosis and Haemostasis*, vol. 3, Issue Supplement s1, p. #OR160.
Saito et al., "Establishment of Factor VIII Mimetic Antibodies and Their In Vitro Activities in Hemophilia A," *2006 National Hemophilia Foundation Symposia*.
Sampei et al., "Identification and multidimensional optimization of an asymmetric bispecific IgG antibody mimicking the function of factor VIII cofactor activity," *PLoS One*, 2013;8(2):e57479. doi: 10.1371/journal.pone.0057479. Epub Feb. 28, 2013.
Schlereth et al., "T-cell activation and B-cell depletion in chimpanzees treated with a bispecific anti-CD19/anti-CD3 single-chain antibody construct," *Cancer Immunol Immunother.*, May 2006;55(5):503-14. Epub Jul. 20, 2005.

Sebastian et al., "Treatment of non-small cell lung cancer patients with the trifunctional monoclonal antibody catumaxomab (anti-EpCAM x anti-CD3): a phase I study," *Cancer Immunol Immunother.*, 56(10):1637-44 (2007).
Seimetz et al., "Development and approval of the trifunctional antibody catumaxomab (anti-EpCAM x anti-CD3) as a targeted cancer immunotherapy," *Cancer Treat Rev.*, 36(6):458-67 (2010).
Shima et al., "Factor VIII Mimetic Antibody: (2) In Vitro Assessment of Cofactor Activity in Hemophilia A," *2005 International Society of Thrombosis and Haemostasis*, vol. 3, Issue Supplement s1, p. #P0038.
Shima, M., "Bispecific antibodies to coagulation factors IXa and X mimic the function of factor VIII," *2006 World Federation of Haemophilia* (Haemophilia, 12(Suppl. 2):98 (2006)).
Shirahata, Minna ni yakudatsu ketsuyubyo no kiso to rinsho. Iyaku (Medicine and Drug) Journal Co., Ltd., 280-9 (2009) (including English translation).
Soeda et al., "Factor VIII Taitei Kotai (1) Ko FIXa/FX bispecific Kotai no Sakusei oyobi characterization," *Rinsho Ketsueki*, 46(8):728 (2005) (including English translation).
Soeda et al., "Phage library-ho ni yori Sakusei shita Ko-FIXa/Ko-FX bispecific Kotai no FVIII Taitei Sayo," *Jpn J Thromb Hemost.*, 16(5):526 (2005) (including English translation).
Spiess et al., "Bispecific antibodies with natural architecture produced by co-culture of bacteria expressing two distinct half-antibodies," *Nat Biotechnol.*, Aug. 2013; 31(8):753-8. doi: 10.1038/nbt.2621. Epub Jul. 7, 2013.
Staerz et al., "Hybrid antibodies can target sites for attack by T cells," *Nature*, 314(6012):628-31 (1985).
Stroehlein et al., "Induction of anti-tumor immunity by trifunctional antibodies in patients with peritoneal carcinomatosis," *J Exp Clin Cancer Res.*, Feb. 14, 2009;28:18. doi: 10.1186/1756-9966-28-18.
Suzuki, "Research and Development of Antibody Pharmaceuticals," *NIBS Letter*, 56(4):45-51 (2010) (English translation).
Teerinen et al., "Structure-based stability engineering of the mouse IgG1 Fab fragment by modifying constant domains," *J Mol Biol.*, 361(4):687-97 (2006).
Thakur et al., "Cancer therapy with bispecific antibodies: Clinical experience," *Curr Opin Mol Ther.*, 12(3):340-9 (2010).
Tsubaki et al., "C-terminal modification of monoclonal antibody drugs: amidated species as a general product-related substance," *Int J Biol Macromol.*, 52:139-47. doi: 10.1016/j.ijbiomac.2012.09.016. Epub Sep. 25, 2012.
Vehar et al., "Structure of human factor VIII," *Nature*, 312(5992):337-42 (1984).
Wolf et al., "BiTEs: bispecific antibody constructs with unique anti-tumor activity," *Drug Discov Today*, 10(18):1237-44 (2005).
Wood et al., "Expression of active human factor VIII from recombinant DNA clones," *Nature*, 312(5992):330-7 (1984).
Zuo et al., "An efficient route to the production of an IgG-like bispecific antibody," *Protein Eng.*, 13(5):361-7 (2000).
International Search Report for App. Ser. No. PCT/JP2011/076486, mailed Dec. 27, 2011, 4 pages.
Fish & Richardson P.C., Amendment in Reply to Action dated Aug. 2, 2013 in U.S. Appl. No. 12/679,922, filed Jan. 29, 2014, 24 pages.
USPTO Non-Final Office Action in U.S. Appl. No. 12/679,922, dated Mar. 18, 2014, 11 pages.
Fish & Richardson P.C., Amendment in Reply to Action dated Mar. 18, 2014 in U.S. Appl. No. 12/679,922, filed Jun. 18, 2014, 13 pages.
USPTO Final Office Action in U.S. Appl. No. 12/679,922, dated Jul. 28, 2014, 12 pages.
International Search Report for App. Ser. No. PCT/JP2011/077603, mailed Mar. 13, 2012, 8 pages.
Chappel et al., "Identification of a secondary Fc gamma RI binding site within a genetically engineered human IgG antibody," *J Biol Chem.*, Nov. 25, 1993;268(33):25124-31.
Chappel et al., "Identification of the Fc gamma receptor class I binding site in human IgG through the use of recombinant IgG1/IgG2 hybrid and point-mutated antibodies," *Proc Natl Acad Sci U S A.*, Oct. 15, 1991;88(20):9036-40.

(56) References Cited

OTHER PUBLICATIONS

Reist et al., "Human IgG2 constant region enhances in vivo stability of anti-tenascin antibody 81C6 compared with its murine parent," *Clin Cancer Res.*, Oct. 1998;4(10):2495-502.
USPTO Notice of Allowance in U.S. Appl. No. 12/679,922, dated Mar. 30, 2015, 12 pages.
Bowen, Haemophilia A and haemophilia B: molecular insights, *Mol Pathol.*, Feb. 2002;55(1):1-18.
Brandstetter et al., "X-ray structure of clotting factor IXa: active site and module structure related to Xase activity and hemophilia B," *Proc Natl Acad Sci U S A*, Oct. 10, 1995;92(21):9796-800.
De Pascalis et al., "Grafting of 'abbreviated' complementary-determining regions containing specificity-determining residues essential for ligand contact to engineer a less immunogenic humanized monoclonal antibody," *Journal of Immunology*, Sep. 15, 2002;169(6):3076-3084.
Fay, "Activation of factor VIII and mechanisms of cofactor action," *Blood Rev.*, Mar. 2004;18(1):1-15.
Gonzales et al., "Minimizing the immunogenicity of antibodies for clinical application," *Tumour Biol.*, Jan.-Feb. 2005;26(1):31-43.
Iwahashi et al., "CDR substitutions of a humanized monoclonal antibody (CC49): contributions of individual CDRs to antigen binding and immunogenicity," *Mol Immunol.*, Oct.-Nov. 1999;36(15-16):1079-91.
Jirholt et al., "Exploiting sequence space: shuffling in vivo formed complementarity determining regions into a master framework," *Gene.*, Jul. 30, 1998;215(2):471-6.
Schmidt et al., "Structure-function relationships in factor IX and factor IXa," *Trends Cardiovasc Med.*, Jan. 2003;13(1):39-45.
Tamura et al., "Structural correlates of an anticarcinoma antibody: identification of specificity-determining residues (SDRs) and development of a minimally immunogenic antibody variant by retention of SDRs only," *J Immunol.*, Feb. 1, 2000;164(3):1432-41.
Notice of Opposition against EP 1 876 236, dated May 20, 2015, in the name of Chugai Seiyaku Kabushiki Kaisha brought by Novo Nordisk A/S, 23 pages.
Notice of Opposition against EP 1 876 236, dated May 22, 2015, in the name of Chugai Seiyaku Kabushiki Kaisha brought by Baxalta Innovations GmbH, 37 pages.
Medesan et al., "Delineation of the amino acid residues involved in transcytosis and catabolism of mouse IgG1," *J Immunol.*, Mar. 1, 1997;158(5):2211-7.
Pan et al., "Blocking neuropilin-1 function has an additive effect with anti-VEGF to inhibit tumor growth," *Cancer Cell*, Jan. 2007;11(1):53-67.
Singer et al., Genes & Genomes, 1991;67-69.
Singer et al., Genes & Genomes, 1998;1:63-64.
Ruf et al., "Induction of a long-lasting antitumor immunity by a trifunctional bispecific antibody," *Blood*, Oct. 15, 2001;98(8):2526-34.
Allard et al., "Antigen binding properties of highly purified bispecific antibodies," *Mol Immunol.*, Oct. 1992;29(10):1219-27.
Batra et al., "Pharmacokinetics and biodistribution of genetically engineered antibodies," *Curr Opin Biotechnol.*, Dec. 2002;13(6):603-8.
Borrebaeck et al., "Antibody evolution beyond Nature," *Nat Biotechnol.*, Dec. 2002;20(12):1189-90.
Greenwood et al., "Structural motifs involved in human IgG antibody effector functions," *Eur J Immunol.*, May 1993;23(5):1098-104.
Griffin et al., "Analysis of heavy and light chain sequences of conventional camelid antibodies from *Camelus dromedarius* and *Camelus bactrianus* species," *J Immunol Methods*, Mar. 2014;405:35-46. doi: 10.1016/j.jim.2014.01.003. Epub Jan. 18, 2014.
Hamers-Casterman et al., "Naturally occurring antibodies devoid of light chains," *Nature*, Jun. 3, 1993;363(6428):446-8.
Igawa et al., "VH/VL interface engineering to promote selective expression and inhibit conformational isomerization of thrombopoietin receptor agonist single-chain diabody," *Protein Eng Des Sel.*, Aug. 2010;23(8):667-77. doi: 10.1093/protein/gzq034. Epub Jun. 24, 2010.
Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.
Lebégue et al., "Production and characterization of hybrid monoclonal antibodies with IgG1/IgG3 double isotype," *C R Acad Sci III.*, 1990;310(9):377-82.
Lloyd et al., "The production of a bispecific anti-CEA, anti-hapten (4-amino-phthalate) hybrid-hybridoma," *J Natl Med Assoc.*, Oct. 1991;83(10):901-4.
Male et al., "Antibodies" *Immunology*, 7th Edition (2006), published by Elsevier Ltd., pp. 59-86.
Michaelsen et al., "A mutant human IgG molecule with only one C1q binding site can activate complement and induce lysis of target cells," *Eur J Immunol.*, Jan. 2006;36(1):129-38.
O'Shea et al., "Peptide 'Velcro': design of a heterodimeric coiled coil," *Curr Biol.*, Oct. 1, 1993;3(10):658-67.
Roitt et al., *Immunology*, M., Mir, 5th Edition (2000), pp. 97-113.
Smolen et al., "Interleukin-6: a new therapeutic target," *Arthritis Res Ther.*, 2006;8 Suppl 2:S5. Epub Jul. 28, 2006.
Wang et al., "Conserved amino acid networks involved in antibody variable domain interactions," *Proteins*, Jul. 2009;76(1):99-114. doi: 10.1002/prot.22319.
U.S. Appl. No. 10/575,905, Hattori et al., filed Apr. 30, 2007.
U.S. Appl. No. 11/910,128, Igawa et al., filed Oct. 7, 2008.
U.S. Appl. No. 11/910,836, Hattori et al., filed Jan. 12, 2009.
U.S. Appl. No. 13/434,643, Hattori et al., filed Mar. 29, 2012.
U.S. Appl. No. 14/921,590, Hattori et al., filed Oct. 23, 2015.
U.S. Appl. No. 15/172,727, Hattori et al., filed Jun. 3, 2016.
U.S. Appl. No. 12/295,039, Igawa et al., filed Jan. 20, 2009.
U.S. Appl. No. 14/741,786, Igawa et al., filed Jun. 17, 2015.
U.S. Appl. No. 12/680,082, Igawa et al., filed Jun. 25, 2010.
U.S. Appl. No. 14/962,293, Igawa et al., filed Dec. 8, 2015.
U.S. Appl. No. 13/257,145, Igawa et al., filed Nov. 22, 2011.
U.S. Appl. No. 14/680,250, Igawa et al., filed Apr. 7, 2015.
U.S. Appl. No. 13/497,269, Kuramochi et al., filed Jun. 1, 2012.
U.S. Appl. No. 13/518,861, Igawa et al., filed Oct. 4, 2012.
U.S. Appl. No. 13/582,073, Kuramochi et al., filed Dec. 20, 2012.
U.S. Appl. No. 14/019,117, Igawa et al., filed Sep. 5, 2013.
U.S. Appl. No. 14/019,712, Igawa et al., filed Sep. 6, 2013.
U.S. Appl. No. 15/132,996, Igawa et al., filed Apr. 19, 2016.
U.S. Appl. No. 15/288,965, Igawa et al., filed Oct. 7, 2016.
U.S. Appl. No. 13/990,088, Nezu et al., filed Dec. 19, 2013.
U.S. Appl. No. 15/024,063, Igawa et al., filed Mar. 23, 2016.
U.S. Pat. No. 8,597,911, Miyazaki et al., issued Dec. 3, 2013.
U.S. Pat. No. 8,062,635, Hattori et al., issued Nov. 22, 2001.
U.S. Pat. No. 9,096,651, Igawa et al., issued Aug. 4, 2015.
U.S. Pat. No. 9,228,017, Igawa et al., issued Jan. 5, 2016.
U.S. Pat. No. 9,334,331, Igawa et al., issued May 10, 2016.
U.S. Appl. No. 15/024,063, filed Mar. 23, 2016, Igawa et al.
U.S. Appl. No. 15/132,996, filed Apr. 19, 2016, Igawa et al.
Asano et al., "Highly effective recombinant format of a humanized IgG-like bispecific antibody for cancer immunotherapy with retargeting of lymphocytes to tumor cells," *JBiol Chem.*, Sep. 21, 2007;282(38):27659-65. Epub Jul. 19, 2007.
Chugai Seiyaku Kabushiki Kaisha's letter dated Jun. 12, 2013, regarding oral proceedings scheduled on Jun. 26, 2013, in App. Ser. No. EP 06 73 0769.4-1412.
Gramer et al., "Production of stable bispecific IgG1 by controlled Fab-arm exchange: scalability from bench to large-scale manufacturing by application of standard approaches," *MAbs.*, Nov.-Dec. 2013;5(6):962-73. doi: 10.4161/mabs 26233. Epub Aug. 22, 2013.
Johnson et al., "Kabat database and its applications: 30 years after the first variability plot," *Nucleic Acids Res.*, Jan. 1, 2000;28(1):214-8.
Labrijn et al., "Efficient generation of stable bispecific IgG1 by controlled Fab-arm exchange," *Pro Natl Acad Sci U S A.*, Mar. 26, 2013;110(13):5145-50. doi: 10.1073/pnas.1220145110. Epub Mar. 11, 2013.

(56) References Cited

OTHER PUBLICATIONS

Labrijn et al., "Species-specific determinants in the IgG CH3 domain enable Fab-arm exchange by affecting the noncovalent CH3-CH3 interaction strength," *J Immunol.*, Sep. 15, 2011;187(6):323846. doi: 10.4049/jimmunol.1003336. Epub Aug. 12, 2011.
Rispens et al., "Dynamics of inter-heavy chain interactions in human immunoglobulin G (IgG) subclasses studied by kinetic Fab arm exchange," *J Biol Chem.*, Feb. 28, 2014;289(9):6098-109. doi: 10.1074/jbc.M113.541813. Epub Jan. 14, 2014.
Schaefer et al., "Immunoglobulin domain crossover as a generic approach for the production of bispecific IgG antibodies," *Proc Natl Acad Sci U S A.*, Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intra-chain disulfide bonds," *Mol Immunol.*, Jan. 2001;38(1):1-8.
Van Der Neut Kolfschoten et al., "Anti-inflammatory activity of human IgG4 antibodies by dynamic Fab arm exchange," *Science*, Sep. 14, 2007;317(5844):1554-7.
Ward et al., "Binding activities of a repertoire of single immunoglobulin variable domains secreted from *Escherichia coli*," Nature, Oct. 12, 1989;341(6242):544-6.
Mcphee et al., "Engineering human immunodeficiency virus 1 protease heterodimers as macromolecular inhibitors of viral maturation," *Proc Natl Acad Sci U S A.*, Oct. 15, 1996; 93(21):11477-81.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
U.S. Appl. No. 15/172,727, filed Jun. 3, 2016, Hattori et al.
U.S. Appl. No. 15/288,965, filed Oct. 7, 2016, Igawa et al.
Dall'Acqua et al., "Increasing the affinity of a human IgG1 for the neonatal Fc receptor: biological consequences," *J. Immunol.*, Nov. 1, 2002;169(9):5171-80.
U.S. Appl. No. 13/990,088, filed Dec. 19, 2013.
U.S. Pat. No. 8,597,911, issued Dec. 3, 2013.
U.S. Appl. No. 14/921,590, filed Oct. 23, 2015, Hattori et al.
U.S. Appl. No. 14/962,293, filed Dec. 8, 2015, Igawa et al.
Asselta et al., "Factor V Deficiency," Semin Thromb. Hemost., 35:382-389 (2009).
Association of Hemophilia Clinic Directors of Canada, "Hemophilia and Von Willebrand's disease: 2. Management. Association of Hemophilia Clinic Directors of Canada," Canadian Medical Association Journal, 153(2):147-157 (1995).
Bajaj et al., "A Monoclonal Antibody to Factor IX That Inhibits the Factor VIII:Ca Potentiation of Factor X Activation," J. Biol. Chem., 260(21):11574-11580 (1985).
Bebbington et al., "High-Level Expression of a Recombinant Antibody from Myeloma Cells Using a Glutamine Synthetase Gene as an Amplifiable Selectable Marker," Biotechnology (NY), 10:169-175 (1992).
Bessos et al., "The characterization of a panel of monoclonal antibodies to human coagulation factor IX," Thrombosis Research, 40:863-867 (1985).
Bian et al., "Discovery of promiscuous HLA-II-restricted T cell epitopes with TEPITOPE," Methods, Dec. 2004;34(4):468-75.
Bolton-Maggs et al., "Haemophilias A and B," The Lancet, May 24, 2003;361:1801-9.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992;11:41-51.
Brennan et al., "Preparation of Bispecific Antibodies by Chemical Recombination of Monoclonal Immunoglobulin G1 Fragments," Science, Jul. 5, 1985;229:81-3.

Brinkman et al. "Phospholipid-binding domain of factor Viii is involved in endothelial cell-mediated activation of factor X by factor IXa," Arterioscler. Thromb. Vasc. Biol., Mar. 1, 2002;22(3):511-6.
Davie et al., "The coagulation cascade: Initiation, maintenance, and regulation," Biochemistry, Oct. 29, 1991;30(43):10363-70.
Dhiman et al., "Gene expression microarrays: a 21st century tool for directed vaccine design," Vaccine, Oct. 12, 2001;20(1-2):22-30.
Francois et al., "Construction of a Bispecific Antibody Reacting with the α- and β-Chains of the Human IL-2 Receptor," J. Immunol., May 15, 1993;150:4610-9.
GenPept Accession No. AAC26541, "anti BoNT/A Hc scFv antibody [synthetic construct]," 1 page (Aug. 1, 2001).
Grosse-Hovest et al., "A recombinant bispecific single-chain antibody induces targeted, supra-agonistic CD28-stimulation and tumor cell killing", European Journal of Immunology, May 2003; 33(5):1334-40.
Hämmerling et al., "Use of Hybrid Antibody with Anti-γG and Anti-Ferritin Specificities in Locating Cell Surface Antigens by Electron Microscopy," J. Exp. Med., Dec. 1, 1968;128:1461-73.
Hoad et al. "Characterization of monoclonal antibodies to human factor X/Xa: Initial observations with a quantitative ELISA procedure," J. Immunol. Methods, Feb. 15, 1991;136(2):269-78.
Hsia et al., "Treatment of acquired factor X inhibitor by plasma exchange with concomitant intravenous immunoglobulin and corticosteroids," Am. J. Hematol., Apr. 2008;83:318-20.
Huse et al., "Generation of a Large Combinatorial Library of the Immunoglobulin Repertoire in Phage Lambda," Science, Dec. 8, 1989;246:1275-81.
Kabsch et al., "On the use of sequence homologies to predict protein structure: identical pentapeptides can have completely different conformations," Proc Natl Acad Sci USA., Feb. 1984;81(4):1075-8.
Kang et al., "Linkage of recognition and replication functions by assembling combinatorial antibody Fab libraries along phage surfaces," Proc. Natl. Acad. Sci. USA, May 15, 1991;88:4363-6.
Karpovsky et al., "Production of Target-Specific Effector Cells Using Hetero-Cross-Linked Aggregates Containing Anti-Target Cell and Anti-Fcγ Receptor Antibodies," J. Exp. Med., Dec. 1, 1984;160:1686-701.
Kim et al., "Mammalian type I interferon receptors consists of two subunits: IFNaR1 and IFNaR2," Gene, Sep. 1, 1977;196:279-86.
Kroesen et al., "Phase I study of intravenously applied bispecific antibody in renal cell cancer patients receiving subcutaneous interleukin 2," Br. J. Cancer, Oct. 1994;70:652-61.
Kurokawa et al., "Enhanced Fibrinolysis by a Bispecific Monoclonal Antibody Reactive to Fibrin and Tissue Plasminogen Activator," Bio/Technology, Nov. 1989; 7:1163-7.
Lapan et al., "Interaction of the A1 Subunit of Factor VIIIa and the Serine Protease Domain of Factor X Identified by Zero-length Cross-linking," Thromb. Haemost., Sep. 1998;80:418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J. Nucl. Med., Oct. 1993; 34:1662-71.
Lenting et al., "The life cycle of coagulation factor VIII in view of its structure and function", Blood, Dec. 1, 1998;92(11):3983-96.
Link et al., "Production and Characterization of a Bispecific IgG Capable of Inducing T-Cell-Mediated Lysis of Malignant B Cells," Blood, Jun. 15, 1993;81:3343-9.
Löfqvist et al., "Haemophilia prophylaxis in young patients —a long-term follow-up," J. Intern. Med., May 1997;241:395-400.
Lu et al., "Fab-scFv fusion protein: an efficient approach to production of bispecific antibody fragments," J. Immunol. Methods, Sep. 15, 2002;267:213-26.
Lu et al., "Di-diabody: a novel tetravalent bispecific antibody molecule by design," J. Immunol. Methods, Aug. 2003;279:219-32.
Massino et al., "Quantitative analysis of the products of IgG chain recombination in hybrid hybridomas based on affinity chromatography and radioimmunoassay," J. Immunol. Methods, Feb. 14, 1997;201:57-66.
Mccafferty et al., "Phage antibodies: filamentous phage displaying antibody variable domains," Nature, Dec. 6, 1990;348:552-4.

(56) References Cited

OTHER PUBLICATIONS

Menegatti et al., "Factor X Deficiency," Semin Thromb. Hemost., Jun. 2009;35:407-15.
Mertens et al., "Factor VIII-Factor IX Interactions: Molecular Sites Involved in Enzyme-Cofactor Complex Assembly," Thromb. Haemost., Aug. 1999;82:209-17.
Milstein et al., "Hybrid hybridomas and their use in immunohistochemistry," Nature, Oct. 6-12, 1983;305:537-40.
Narhi et al., "Asn to Lys mutations at three sites which are N-glycosylated in the mammalian protein decrease the aggregation of Escherichia coli-derived erythropoietin," Protein Eng., Feb. 2001;14(2):135-40.
"National Haemophilia Foundation (NHF) Medical and Scientific Advisory Council (MASAC) Recommendations Concerning Prophylaxis," Medical Bulletin, No. 193, 1 page (1994).
Nilsson et al., "Twenty-five years' experience of prophylactic treatment in severe haemophilia A and B," J. Intern. Med., Jul. 1992;232:25-32.
Nilsson et al., "Induction of split tolerance and clinical cure in high-responding hemophiliacs with factor IX antibodies," Proc. Natl. Acad. Sci. U S A., Dec. 1986;83:9169-73.
Nitta et al., "Preliminary trial of specific targeting therapy against malignant glioma," Lancet, Feb. 17, 1990;335:368-371.
Okubo et al. "The production and characterization of four monoclonal antibodies to human factor X," Nara Med Assoc., 1987;38(1):20-28.
Piper et al., "Interferon therapy in primary care," Primary Care Update for Ob/Gyns, Jul. 2001;8(4):163-69.
Pokkuluri et al., "A domain flip as a result of a single amino-acid substitution," Structure, Aug. 15, 1998;6(8):1067-73.
Price et al., "Tissue factor and tissue factor pathway inhibitor," Anaesthesia, May 2004;59:483-92.
Ruef et al., "A bispecific antifibrin-antiplatelet urokinase conjugate (BAAUC) induces enhanced clot lysis and inhibits platelet aggregation," Thromb. Haemost., Jul. 1999;82(1):109-14.
Sato et al., "Properties of Two VEGF Receptors, Flt-1 and KDR, in Signal Transduction," Ann n. Y. Acad. Sci, May 2000;902:201-207, discussion 205-7.
Segal et al., "Introduction: bispecific antibodies," J. Immunol. Methods, Feb. 1, 2001;248:1-6.
Shima et al., "Factor VIII Taitei Kotai (2), Ketsuyubyo a Kanja Katsueki ni okeru in vitro Gyoko Kassei no Kento", Rinsho Ketsueki, Aug. 30, 2005;46(8):777 (#WS-36-5) (with English translation).
Stickney et al., "Bifunctional Antibody: A Binary Radiopharmaceutical Delivery System for Imaging Colorectal Carcinoma," Cancer Res., Dec. 15, 1991;51:6650-5.
Suresh et al., "Advantages of bispecific hybridomas in one-step immunocytochemistry and immunoassays," Proc. Natl. Acad. Sci. U S A., Oct. 1986;83:7989-93.
Taki, The Journal of Japanese Society on Thrombosis and Hemostasis, Feb. 2, 2002;13:109-113.
Thies et al., "The alternatively folded state of the antibody C(H)3 domain," J Mol Biol., Jun. 22, 2001;309(5):1077-85.
Weiner et al., "A Human Tumor Xenograft Model of Therapy with a Bispecific Monoclonal Antibody Targeting c-erbB-2 and CD16," Cancer Res., Jan. 1, 1993;53:94-100.
Weiner et al., "The Role of T Cell Activation in Anti-CD3 x Antitumor Bispecific Antibody Therapy," J. Immunol., Mar. 1, 1994;152:2385-92.
Xiang et al., "Production of Murine V-Human Crl Chimeric Anti-TAG72 Antibody Using V Region cDNA Amplified by PCR," Mol. Immunol., Aug. 1990;27:809-17.
Yasukawa et al., "Structure and expression of human B cell stimulatory factor-2 (BSF-2/IL-6) gene," EMBO J., Oct. 1987;6(10):2939-45.
Coloma et al., "Position effects of variable region carbohydrate on the affinity and in vivo behavior of an anti-(1-->6) dextran antibody," J Immunol., Feb. 15, 1999;162(4):2162-70.
Dufner et al., "Harnessing phage and ribosome display for antibody optimization," Trends Biotechnol., Nov. 2006;24(11):523-9. Epub Sep. 26, 2006.
Hird et al., "Tumour localisation with a radioactively labelled reshaped human monoclonal antibody," Br J Cancer, Nov. 1991;64(5):911-4.
Hong et al., "Enhanced cellular uptake and transport of polyclonal immunoglobulin G and fab after their cationization," J Drug Target., 2000;8(2):67-77.
Li et al., "Construction and characterization of a humanized anti-human CD3 monoclonal antibody 12F6 with effective immunoregulation functions," Immunology, Dec. 2005;116(4):487-98.
Marshall et al., "Rational design and engineering of therapeutic proteins," Drug Discov Today, Mar. 1, 2003;8(5):212-21.
Padlan, "X-ray crystallography of antibodies," Adv Protein Chem., 1996;49:57-133.
Pardridge et al., "Enhanced cellular uptake and in vivo biodistribution of a monoclonal antibody following cationization," J Pharm Sci., Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Sarkar et al., "Rational cytokine design for increased lifetime and enhanced potency using pH-activated 'histidine switching'," Nat Biotechnol., Sep. 2002;20(9):908-13. Epub Aug. 5, 2002.
Sharifi et al., "Improving monoclonal antibody pharmacokinetics via chemical modification," Q J Nucl Med., Dec. 1998;42(4):242-9.
Strohl, "Optimization of Fc-mediated effector functions of monoclonal antibodies," Curr Opin Biotechnol., Dec. 2009;20(6):685-91. doi: 10.1016/j.copbio.2009.10.011. Epub Nov. 4, 2009.
Tabrizi et al , "Elimination mechanisms of therapeutic monoclonal antibodies," Drug Discov Today, Jan. 2006;11(1-2):81-8.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Roopenian et al., "FcRn: the neonatal Fc receptor comes of age," Nat Rev Immunol., Sep. 2007;7(9):715-25. Epub Aug. 17, 2007.
Yang et al., "CDR walking mutagenesis for the affinity maturation of a potent human anti-HIV-1 antibody into the picomolar range," J Mol Biol., Dec. 1, 1995;254(3):392-403.

* cited by examiner

FIG. 2
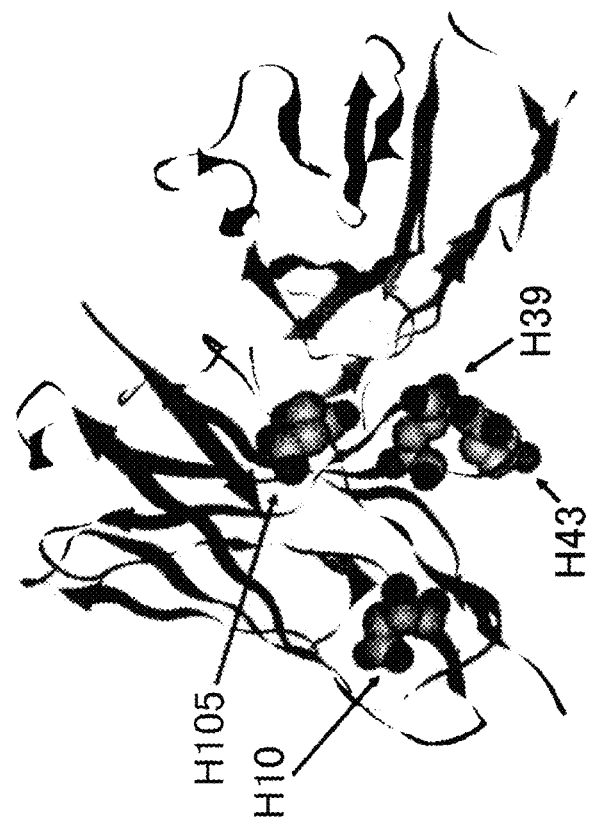
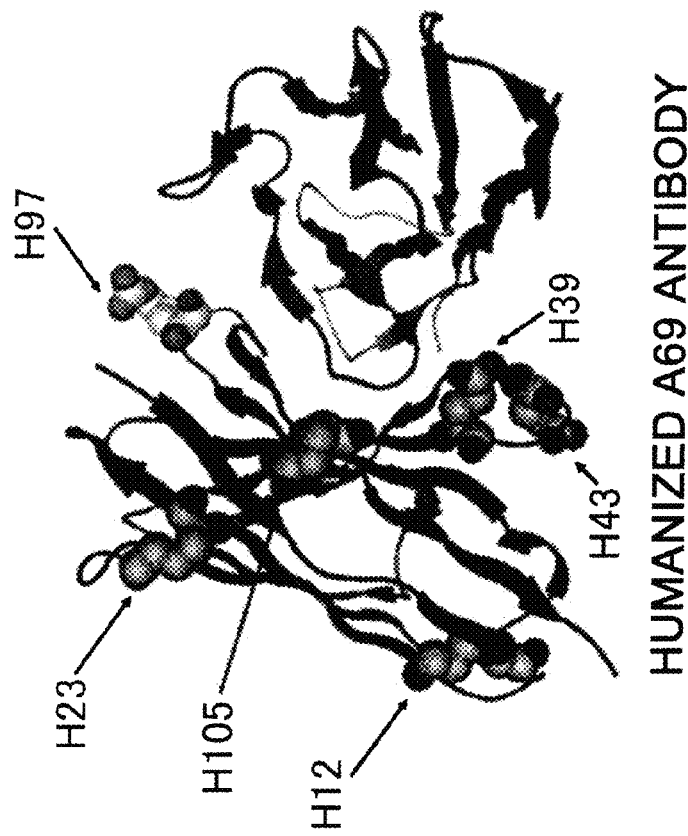

METHODS OF MODIFYING ANTIBODIES FOR PURIFICATION OF BISPECIFIC ANTIBODIES

CROSS-REFERENCE TO RELATED APPLICATIONS

This application is the National Stage of International Application Serial No. PCT/JP2007/057058, filed on Mar. 30, 2007, which claims the benefit of Japanese Application Serial No. 2006-097795, filed on Mar. 31, 2006 and Japanese Application Serial No. 2006-275804, filed on Oct. 6, 2006. The contents of the foregoing applications are hereby incorporated by reference in their entirety.

TECHNICAL FIELD

The present invention relates to methods of modifying antibodies for purification of bispecific antibodies, methods for separating the bispecific antibodies, and pharmaceutical compositions and such comprising the bispecific antibodies as active ingredients.

BACKGROUND ART

Due to their highly stable nature in blood and relatively few side effects, antibodies have been receiving much attention as pharmaceuticals. Of particular note are bispecific antibodies that can simultaneously recognize two types of antigens, e.g., antibody A and antibody B (see Non-Patent Document 1). MDX-210, which is currently under clinical trial investigation, is an IgG-type bispecific antibody that retargets FcγRI-expressing monocytes and such to HER-2/neu-expressing cancer cells (see Non-Patent Document 2). In general, antibodies are produced using genetic recombination techniques. One specific technique involves the cloning of a DNA encoding an antibody protein from antibody-producing cells, such as hybridomas or sensitized lymphocytes that produce antibodies or a phage library presenting antibody genes, and the insertion of such into a suitable vector, which is then transfected into host cells for antibody production. Production of IgG type bispecific antibodies using genetic recombination techniques involves the introduction of a total of four types of genes into cells, in which these genes of H chains and L chains constitute two types of IgGs of interest, and the secretion of the antibodies by coexpression. In this type of system, expression of the constituent genes of the wild type H chain and L chains leads to random association between two types of H chains and association between H and L chains, and thus, the proportion of the bispecific antibody of interest becomes very small. More particularly, only one out of ten types produced is the bispecific antibody of interest, rendering the production efficiency quite low. Decreased efficiency in the production of the antibody of interest is not only an obstacle for purifying the antibody of interest, but also increases the nonuniformity, such as the lot-to-lot differences, which, in turn, leads to swelling production costs.

Techniques for obtaining L chains commonly shared by both H chains, and the knobs-into-holes technique for heterologous association of H chains have been reported as efficient bispecific antibody production methods for developing bispecific antibodies. More specifically, a common L chain, which can maintain both antigen binding activities of the respective H chains that recognize antigen A and antigen B, is identified from a phage library or such. Then, formation of H chain heterodimers is promoted by substituting an amino acid side chain present in the CH3 region of one of the H chains with a larger side chain (knob), and substituting an amino acid side chain present in the CH3 region of the other H chain with a smaller side chain (hole), to place the knob within the hole. Thus, bispecific antibodies of interest can be efficiently obtained (see Patent Document 1, Non-Patent Document 3, and Non-Patent Document 4).

However, even when the knobs-into-holes technique is used for H chain heterodimers, although the content of the chain A-chain B heterodimer of interest can be increased up to a maximum of about 95% as shown in Non-Patent Document 3 and Non-Patent Document 4, the remaining 5% is impurities and consists of chain A and chain B homodimers. To develop bispecific antibodies as pharmaceuticals, the chain A-chain B heterodimers must be purified to the highest possible purity from the three types of molecular species (chain A homodimer, chain B homodimer, and chain A-chain B heterodimer) that are produced when a common L chain is used (Non-Patent Document 3 and Non-Patent Document 4). Therefore, it is necessary to remove the 5% impurities, which are the chain A and chain B homodimers, thereby purifying the chain A-chain B heterodimer to a high purity that allows the heterodimer to be developed into a pharmaceutical. When a common L chain is used without the knobs-into-holes technique, the production ratio of the chain A homodimer, chain A-chain B heterodimer, and chain B homodimer is theoretically 1:2:1, and the 50% impurities which are the chain A and chain B homodimers must be removed.

Several chromatographic methods for separating the chain A-chain B heterodimer from the chain A and chain B homodimers at the level of pharmaceutical manufacturing have been reported. Non-Patent Document 5 reports a method for selectively purifying the chain A-chain B heterodimer using mouse IgG2a as chain A and rat IgG2b as chain B. This method uses difference between the respective mouse IgG2a and rat IgG2b H chains in their affinity for protein A, and purifies the chain A-chain B heterodimer by controlling the pH for elution from protein A. However, since constant regions from mouse and rat are used, this method is difficult to apply to pharmaceuticals for human from the perspective of antigenicity. Furthermore, since this method cannot separate the chain A-chain B heterodimer, which is composed from H chains belonging to the same subclass, its use is limited.

A method for purifying the chain A-chain B heterodimer using hydrophobic interaction chromatography is reported in Non-Patent Document 6. However, the peak of the chain A-chain B heterodimer of interest containing anti-CD3 mouse IgG2a and anti-CD19 mouse IgG1 is not sufficiently separated. In addition, H chains belonging to different subclasses are used, and the difference in their hydrophobicity seems to be used for the separation. Thus, this method may not necessarily separate the chain A-chain B heterodimer composed from H chains belonging to the same subclass.

A method for purifying the chain A-chain B heterodimer using thiophilic affinity chromatography is reported in Non-Patent Document 7. However, this method cannot be adopted to separate the chain A-chain B heterodimer composed from H chains belonging to the same subclass, because it uses mouse IgG1 and rat IgG2a, and the free cysteines (thiol groups) in the hinge regions. In addition, since the free cysteines are involved in aggregation during storage, this method is not suitable for development of stable pharmaceutical formulations.

Affinity chromatography using antigens is reported in Non-Patent Document 8. However, since affinity chromatography using proteins or peptide antigens is problematic in terms of cost and column stability, production of pharmaceuticals using affinity chromatography is unconventional. Furthermore, to purify the chain A-chain B heterodimer that binds to both antigens, affinity chromatography must be performed twice, and this is expected to become costly. It has been reported that there are antibodies that recognize only the three-dimensional structures of antigens as well as antibodies that have desired functions but low affinity. For antibodies with such characteristics, it is difficult to adopt affinity chromatography that uses antigens. Therefore, purification of bispecific antibodies using affinity chromatography cannot be used widely.

As described above, purification of the chain A-chain B heterodimer of a bispecific antibody has been performed only within limited scope. There has been no report on methods for purifying the chain A-chain B heterodimer of a bispecific antibody composed from the same H chain subclass and constant region sequence to a high purity that is acceptable for pharmaceuticals. When two types of antibodies constituting a bispecific antibody have the same constant region sequence, the chain A-chain B heterodimer needs to be separated based solely on the differences in their variable region sequences. However, since the amino acid sequence homology between antibody variable regions is very high (Non-Patent Document 9), it has been difficult to purify the chain A-chain B heterodimer to a high purity that is acceptable for pharmaceuticals solely based on the differences in their variable region sequences.

[Patent Document 1]
WO 96/27011
[Non-Patent Document 1]
Marvin J S, and Zhu Z, "Recombinant approaches to IgG-like bispecific antibodies.", Acta. Pharmacol. Sin., June 2005, Vol. 26(6), p. 649-58.
[Non-Patent Document 2]
Segal D. M. et al., Current Opinion in Immunology, 1999, Vol. 11, p. 558-562.
[Non-Patent Document 3]
Merchant A M et al., "An efficient route to human bispecific IgG", Nat. Biotechnol., July 1998, Vol. 16(7), p. 677-81.
[Non-Patent Document 4]
Carter P, "Bispecific human IgG by design.", J. Immunol. Methods., February 2001, Vol. 248(1-2), p. 7-15.
[Non-Patent Document 5]
Lindhofer H et al., "Preferential species-restricted heavy/light chain pairing in rat/mouse quadromas. Implications for a single-step purification of bispecific antibodies.", J. Immunol., Jul. 1, 1995, Vol. 155(1), p. 219-25.
[Non-Patent Document 6]
Manzke O et al., "Single-step purification of bispecific monoclonal antibodies for immunotherapeutic use by hydrophobic interaction chromatography.", J. Immunol. Methods., Oct. 13, 1997, Vol. 208(1), p. 65-73.
[Non-Patent Document 7]
Kreutz F T et al., "Efficient bispecific monoclonal antibody purification using gradient thiophilic affinity chromatography.", J. Chromatogr. B. Biomed. Sci. Appl., Sep. 4, 1998, Vol. 714(2), p. 161-70.
[Non-Patent Document 8]
Gupta S and Suresh M, "Affinity chromatography and co-chromatography of bispecific monoclonal antibody immunoconjugates.", J. Biochem. Biophys. Methods., May 31, 2002, Vol. 51(3), p. 203-16. Review.
[Non-Patent Document 9]
Carl Branden, Introduction to Protein Structure 2nd edition, Newton Press.

DISCLOSURE OF THE INVENTION

Problems to be Solved by the Invention

The present invention was achieved in view of the above circumstances. An objective of the present invention is to provide methods for modifying the amino acids of antibody variable regions to efficiently purify bispecific antibodies, pharmaceutical compositions comprising the modified bispecific antibodies, and methods for producing the bispecific antibody pharmaceutical compositions. Another objective of the present invention is to provide bispecific antibodies in which the heavy chain constant regions have been modified, pharmaceutical compositions comprising the modified bispecific antibodies, and methods for producing the bispecific antibody pharmaceutical compositions.

Means for Solving the Problems

The present inventors conducted dedicated research on methods that substitute amino acids in antibody variable regions. These methods use a standard chromatography column to efficiently purify bispecific antibodies of interest which was conventionally challenging.

The present inventors devised methods for efficiently purifying bispecific antibodies using a chromatography column based on the difference in isoelectric points of the H chains of two types of antibodies, and the difference is introduced by modifying the amino acids present on the surface of the variable regions of the two types of antibodies that constitute a bispecific antibody. Specifically, the present inventors discovered sites of modification in the antibody H chain that enable regulation of the isoelectric point alone without reducing the antibody function (activity). Furthermore, the present inventors confirmed that bispecific antibodies obtained by the methods of the present invention actually maintain their functions.

As described above, the present inventors successfully developed methods for substituting amino acids in the antibody variable regions as efficient methods for purifying any bispecific antibody by using a standard chromatography column, and thereby completed the present invention.

The present inventors further devised methods to efficiently purify bispecific antibodies using a chromatography column based on the difference in isoelectric point. Constant regions of different subclasses originally having different isoelectric points are used as the constant regions of the two types of H chains that constitute a bispecific antibody. Furthermore, the present inventors confirmed that the bispecific antibodies obtained by the methods of the present invention actually maintain their functions.

The present invention relates to methods of substituting amino acids in the antibody variable regions for efficient purification by using a chromatography column, pharmaceutical compositions comprising the modified bispecific antibodies, and methods for producing the bispecific antibody pharmaceutical compositions. The present invention also relates to bispecific antibodies in which the heavy chain constant regions have been modified, pharmaceutical compositions comprising the modified bispecific antibodies, and methods for producing the bispecific antibody pharmaceutical compositions. More specifically, the present invention relates to the following:

[1] A method for producing a multispecific antibody comprising a first polypeptide and a second polypeptide, wherein the method comprises the steps of:
    (a) modifying both or either one of a nucleic acid encoding the amino acid residues of the first polypeptide and a nucleic acid encoding the amino acid residues of the second polypeptide, such that the difference between the isoelectric point of the first polypeptide and that of the second polypeptide will be increased;
    (b) culturing host cells to express the nucleic acids; and
    (c) collecting the multispecific antibody from the host cell culture.

[2] The method of [1], wherein the modification of step (a) is modifying the nucleic acids so that the peaks of the homomultimer of the first polypeptide, the homomultimer of the second polypeptide, and the heteromultimer of the first polypeptide and the second polypeptide will be separated in standard chromatography analysis.

[3] The method of [1], wherein the first polypeptide and the second polypeptide comprise a heavy chain variable region.

[4] The method of [3], wherein the multispecific antibody comprises a third polypeptide comprising a light chain variable region, and wherein the first polypeptide and the second polypeptide each forms a multimer with said third polypeptide.

[5] The method of any one of [1] to [4], wherein the first polypeptide and the second polypeptide comprise a heavy chain constant region.

[6] The method of [5], wherein the heavy chain constant regions comprised in the first polypeptide and the second polypeptide are heavy chain constant regions whose isoelectric points are different from each other.

[7] The method of [6], wherein the heavy chain constant regions with different isoelectric points are IgG1 and IgG4, or IgG1 and IgG2.

[8] The method of [1], wherein the multispecific antibody is a bispecific antibody.

[9] A multispecific antibody produced by the method of [1].

[10] A method for purifying a multispecific antibody comprising a first polypeptide and a second polypeptide, wherein the method comprises the steps of:
    (a) modifying both or either one of a nucleic acid encoding the amino acid residues of the first polypeptide and a nucleic acid encoding the amino acid residues of the second polypeptide, such that the difference between the isoelectric point of the first polypeptide and that of the second polypeptide will be increased;
    (b) culturing host cells to express the nucleic acids; and
    (c) purifying said multispecific antibody from the host cell culture by standard chromatography.

[11] The method of [10], wherein the modification of step (a) is modifying the nucleic acids so that the peaks of the homomultimer of the first polypeptide, the homomultimer of the second polypeptide, and the heteromultimer of the first polypeptide and the second polypeptide will be separated in standard chromatography analysis.

[12] The method of [10], wherein the first polypeptide and the second polypeptide comprise a heavy chain variable region.

[13] The method of [12], wherein the multispecific antibody comprises a third polypeptide comprising a light chain variable region, and wherein the first polypeptide and the second polypeptide each forms a multimer with said third polypeptide.

[14] The method of any one of [10] to [13], wherein the first polypeptide and the second polypeptide comprise a heavy chain constant region.

[15] The method of [14], wherein the heavy chain constant regions comprised in the first polypeptide and the second polypeptide are heavy chain constant regions whose isoelectric points are different from each other.

[16] The method of [15], wherein the heavy chain constant regions with different isoelectric points are IgG1 and IgG4, or IgG1 and IgG2.

[17] The method of [10], wherein the multispecific antibody is a bispecific antibody.

[18] A method for producing a multispecific antibody, wherein the method comprises the purification steps according to the method of [10].

[19] A multispecific antibody produced by the method of [18].

[20] A multispecific antibody comprising a first polypeptide and a second polypeptide, wherein the first polypeptide comprises a heavy chain variable region and/or a heavy chain constant region, wherein at least one amino acid residue selected from the amino acid residues at positions 10, 12, 23, 39, 43, and 105, Kabat numbering, in said heavy chain variable region, or the amino acid residues at positions 137, 196, 203, 214, 217, 233, 268, 274, 276, 297, 355, 392, 419, and 435, EU numbering, in said heavy chain constant region, carries a charge, and wherein the isoelectric point of the first polypeptide and that of the second polypeptide are different from each other.

[21] The multispecific antibody of [20], wherein the second polypeptide comprises a heavy chain variable region and/or a heavy chain constant region, wherein at least one amino acid residue selected from the amino acid residues at positions 10, 12, 23, 39, 43, and 105, Kabat numbering, in said heavy chain variable region, or the amino acid residues at positions 137, 196, 203, 214, 217, 233, 268, 274, 276, 297, 355, 392, 419, and 435, EU numbering, in said heavy chain constant region, is uncharged or carries the opposite charge of that of the charged amino acid residue selected in the heavy chain variable region and/or heavy chain constant region comprised in the first polypeptide.

[22] The multispecific antibody of [20], wherein the charged amino acid residue and the amino acid residue having the opposite charge of that of said charged amino acid residue are selected from the amino acid residues included in either of the following groups, respectively:
(a) glutamic acid (E), and aspartic acid (D); and
(b) lysine (K), arginine (R), and histidine (H).

[23] A multispecific antibody in which the isoelectric point of a first polypeptide and that of a second polypeptide are different, and wherein the peaks of the homomultimer of the first polypeptide, the homomultimer of the second polypeptide, and the heteromultimer of the first polypeptide and the second polypeptide are separated in standard chromatography analysis.

[24] The multispecific antibody of [23], wherein the first polypeptide and the second polypeptide comprise a heavy chain variable region.

[25] The multispecific antibody of [24], wherein the multispecific antibody comprises a third polypeptide comprising a light chain variable region, and wherein the first polypeptide and the second polypeptide each forms a multimer with said third polypeptide.

[26] The multispecific antibody of any one of [23] to [25], wherein the first polypeptide and the second polypeptide comprise a heavy chain constant region.

[27] The multispecific antibody of [26], wherein the heavy chain constant regions comprised in the first polypeptide and the second polypeptide are heavy chain constant regions whose isoelectric points are different from each other.

[28] The multispecific antibody of [27], wherein the heavy chain constant regions with different isoelectric points are IgG1 and IgG4, or IgG1 and IgG2.

[29] The multispecific antibody of [23], wherein the multispecific antibody is a bispecific antibody.

[30] A composition comprising the multispecific antibody of any one of [23] to [29], and a pharmaceutically acceptable carrier.

[31] A nucleic acid encoding a polypeptide constituting the multispecific antibody of any one of [23] to [29].

[32] A host cell comprising the nucleic acid of [31].

[33] A method for producing the multispecific antibody of any one of [23] to [29], wherein the method comprises the step of culturing the host cell of [32], and collecting the polypeptides from the cell culture.

[34] The multispecific antibody of [25], wherein the variable region of the first polypeptide comprises an amino acid sequence of any one of the following (a1) to (a7), wherein the variable region of the second polypeptide comprises an amino acid sequence of any one of the following (b1) to (b3), and wherein the variable region of the third polypeptide comprises an amino acid sequence of the following (c1) or (c2):
  (a1) SEQ ID NO: 7
  (a2) SEQ ID NO: 8
  (a3) SEQ ID NO: 9
  (a4) SEQ ID NO: 10
  (a5) SEQ ID NO: 11
  (a6) SEQ ID NO: 12
  (a7) SEQ ID NO: 13
  (b1) SEQ ID NO: 14
  (b2) SEQ ID NO: 15
  (b3) SEQ ID NO: 16
  (c1) SEQ ID NO: 17
  (c2) SEQ ID NO: 18

[35] The multispecific antibody of [34], wherein the variable region of the first polypeptide comprises the amino acid sequence of SEQ ID NO: 11, wherein the variable region of the second polypeptide comprises the amino acid sequence of SEQ ID NO: 16, and wherein the variable region of the third polypeptide comprises the amino acid sequence of SEQ ID NO: 17.

[36] The multispecific antibody of [34], wherein the variable region of the first polypeptide comprises the amino acid sequence of SEQ ID NO: 12, wherein the variable region of the second polypeptide comprises the amino acid sequence of SEQ ID NO: 16, and wherein the variable region of the third polypeptide comprises the amino acid sequence of SEQ ID NO: 18.

[37] The multispecific antibody of any one of [34] to [36], wherein the first polypeptide and the second polypeptide comprise the human IgG4 constant region, and wherein the third polypeptide comprises the human κ constant region.

BRIEF DESCRIPTION OF THE DRAWINGS

FIG. 2 depicts the result of antibody modeling for the humanized A69H chain variable region (hA69a) with humanized BBA (hAL-F123j4), and the humanized B26H chain variable region (hB26-F123e4) with humanized BBA (hAL-F123j4). The side chains of the amino acids whose surface charges can be modified are emphasized. The numbering was adopted from sequence numbers in the Kabat database (Kabat E A et al. 1991. Sequences of Proteins of Immunological Interest. NIH).

BEST MODE FOR CARRYING OUT THE INVENTION

Figure 1:
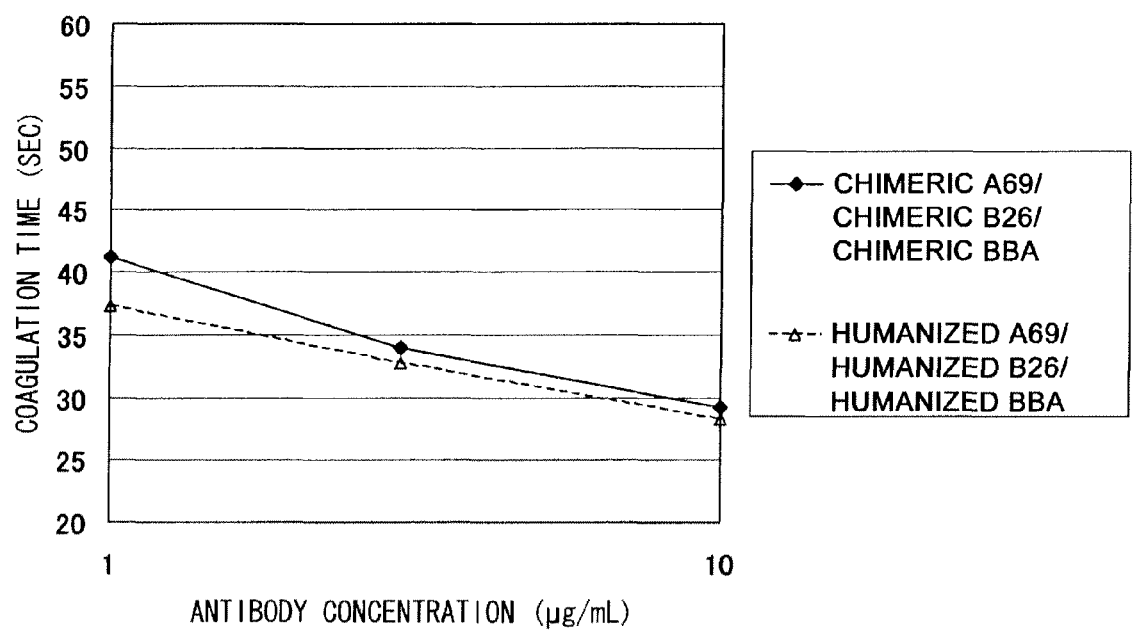
FIG. 1 depicts the result of evaluating the coagulation activity of a humanized bispecific antibody (humanized A69 (hA69a)/humanized B26 (hB26-F123e4)/humanized BBA (hAL-F123j4)). The result shows that the humanized bispecific antibody has a coagulation activity equal to or greater than that of a chimeric bispecific antibody.

The present invention provides methods of modifying antibodies for production of multispecific antibodies. A preferred embodiment of the production methods of the present invention is a method comprising modifying both or either one of a nucleic acid encoding the amino acid residues of a first polypeptide and a nucleic acid encoding the amino acid residues of a second polypeptide, so that the isoelectric points of the first polypeptide and second polypeptide will be different. That is, multispecific antibodies can be produced based on differences in isoelectric point (pI), and the difference can be introduced into polypeptides by altering the charges of the amino acid residues in the first polypeptide and second polypeptide. More specifically, a preferred production method comprises the following steps of:

(a) modifying both or either one of a nucleic acid encoding the amino acid residues of the first polypeptide and a nucleic acid encoding the amino acid residues of the second polypeptide, so that the difference between the isoelectric points of the first polypeptide and second polypeptide will be increased;

(b) culturing host cells to express the nucleic acids; and (c) collecting a multispecific antibody from the host cell culture.

In the present invention, "polypeptides" generally refers to peptides and proteins whose length is approximately ten amino acids or longer. Polypeptides are generally derived from organisms, but are not particularly limited thereto, and for example, they may be composed of an artificially designed sequence. They may also be naturally derived polypeptides, synthetic polypeptides, recombinant polypeptides, or such. Additionally, fragments of the above-mentioned polypeptides are also included in the polypeptides of the present invention.

In the present invention, the phrase "the difference between the isoelectric points of the polypeptides" means that the isoelectric points of two or more polypeptides are made unequal by modifying the charges of the amino acids on the surface of each polypeptide. The difference in the isoelectric points can be observed, for example, by using a technique such as isoelectric focusing. In the present invention, the isoelectric points are preferably modified without altering the structure and/or function (activity) of the polypeptides.

That is, the present invention provides a method for producing a multispecific antibody comprising a first polypeptide and a second polypeptide, wherein the method comprises the steps of:

(a) modifying both or either one of a nucleic acid encoding the amino acid residues of the first polypeptide and a nucleic acid encoding the amino acid residues of the second polypeptide, so that the difference between the isoelectric point of the first polypeptide and that of the second polypeptide will be 0.5 or more, preferably 0.7 or more, and more preferably 0.9 or more;

(b) culturing host cells to express the nucleic acids; and (c) collecting the multispecific antibody from the host cell culture.

Furthermore, the present invention provides methods of modifying antibodies for purification of multispecific antibodies. A preferred embodiment of the purification methods of the present invention is a method comprising the step of modifying both or either one of a nucleic acid encoding the amino acid residues of a first polypeptide and a nucleic acid encoding the amino acid residues of a second polypeptide, so that the isoelectric points of the first polypeptide and second polypeptide will be different. That is, the difference in isoelectric point (pI) is introduced into the polypeptides by altering the charges of the amino acid residues of the first polypeptide and those of the second polypeptide. Thus, multispecific antibodies can be purified using this difference in isoelectric points. More specifically, a purification method comprises the following steps of:

(a) modifying both or either one of a nucleic acid encoding the amino acid residues of the first polypeptide and a nucleic acid encoding the amino acid residues of the second polypeptide, so that the difference between the isoelectric point of the first polypeptide and second polypeptide will be increased;

(b) culturing host cells to express the nucleic acids; and (c) purifying said multispecific antibody from the host cell culture by standard chromatography.

Methods for producing multispecific antibodies which comprise the purification steps of the above-mentioned purification methods are also included in the present invention.

The nucleic acids of the present invention are generally cloned (inserted) into suitable vectors and then introduced into host cells. These vectors are not particularly limited so long as the inserted nucleic acids are stably maintained. For example, when *Escherichia coli* is used as a host, the cloning vectors are preferably pBluescript vectors (Stratagene) and such, while various commercially available vectors may be used. When vectors are used for the purpose of producing the multispecific antibodies (polypeptides) of the present invention, expression vectors are particularly useful. There is no particular limitation on expression vectors, so long as they can express polypeptides in test tubes, *E. coli*, cultured cells, or individual organisms. For example, preferred vectors include pBEST vectors (Promega) for expression in test tubes, pET vectors (Invitrogen) in *E. coli*, the pME18S-FL3 vector (GenBank Accession No. AB009864) in cultured cells, and the pME18S vector (Mol. Cell Biol. 8:466-472 (1998)) in individual organisms. Insertion of the DNAs of the present invention into vectors can be performed, for example, by standard methods such as ligase reactions using restriction enzyme sites (Current protocols in Molecular Biology edit. Ausubel et al. (1987) Publish. John Wiley & Sons. Section 11.4-11.11).

There is no particular limitation on the above-mentioned host cells, and various host cells are used depending on the purpose. Cells used for expressing polypeptides include bacterial cells (for example, Streptococcus, Staphylococcus, *E. coli*, Streptomyces, and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods, such as the calcium phosphate precipitation method, electroporation method (Current protocols in Molecular Biology edit. Ausubel et al. (1987) Publish. John Wiley & Sons. Section 9.1-9.9), lipofection method, and microinjection method.

For secreting host cell-expressed polypeptides into the lumen of the endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into culture media, the multispecific antibodies (polypeptides) produced by the above-mentioned methods can be harvested by collecting the media. When the polypeptides of the present invention are produced inside cells, the cells first are lysed, and then these polypeptides are collected.

The polypeptides of the present invention can be collected and purified from recombinant cell cultures using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

Furthermore, the present invention relates to compositions (agents) comprising a multispecific antibody of the present invention and a pharmaceutically acceptable carrier.

In the present invention, "pharmaceutical compositions" generally refers to agents for treating or preventing, or testing and diagnosing diseases.

The pharmaceutical compositions of the present invention can be formulated by methods known to those skilled in the art. For example, such pharmaceutical compositions can be used parenterally in the form of injections, which are sterile solutions or suspensions prepared with water or another pharmaceutically acceptable liquid. For example, such compositions may be formulated by appropriately combining with a pharmaceutically acceptable carrier or medium, specifically, sterile water, physiological saline, vegetable oil, emulsifier, suspension, surfactant, stabilizer, flavoring agent, excipient, vehicle, preservative, binder, or such, and mixed in a unit dose form that meets the generally accepted requirements for preparation of pharmaceuticals. In such preparations, the amount of active ingredient is adjusted such that a suitable amount within a specified range is obtained.

Sterile compositions for injection can be formulated using vehicles such as distilled water for injection, according to standard protocols for formulation.

Aqueous solutions for injection include, for example, physiological saline and isotonic solutions containing glucose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), non-ionic surfactants (polysorbate 80™, HCO-50, and such) may be used in combination.

Oils include sesame and soybean oils. Benzyl benzoate and/or benzyl alcohol can be used as solubilizers in combination. Buffers (for example, phosphate buffer and sodium acetate buffer), soothing agents (for example, procaine hydrochloride), stabilizers (for example, benzyl alcohol and phenol), and/or antioxidants can also be combined. Prepared injections are generally filled into appropriate ampules.

The pharmaceutical compositions of the present invention are preferably administered parenterally. For example, the compositions may be in the form of injections, transnasal agents, transpulmonary agents, or transdermal agents. For example, such compositions can be administered systemically or locally by intravenous injection, intramuscular injection, intraperitoneal injection, subcutaneous injection, or such.

The administration methods can be appropriately selected in consideration of a patient's age and symptoms. The dosage of a pharmaceutical composition comprising an antibody or a polynucleotide encoding an antibody may be set, for example, within the range of 0.0001 to 1000 mg/kg weight for each administration. Alternatively, the dosage may be, for example, from 0.001 to 100,000 mg per patient. However, in the present invention, the dosage is not necessarily limited to the ranges described above. Although the dosage and administration method vary depending on a patient's weight, age, symptoms, and such, those skilled in the art can select appropriate dosage and administration methods in consideration of the factors described above.

The multispecific antibodies of the present invention can be formulated by combining with other pharmaceutical components as necessary.

The present invention also provides nucleic acids encoding polypeptides that constitute the multispecific antibodies of the present invention. Furthermore, vectors that carry these nucleic acids are also included in the present invention.

The present invention also provides host cells carrying the above described nucleic acids. The host cells are not particularly limited and include, for example, *E coli* and various animal cells. The host cells may be used, for example, as a production system to produce and express the antibodies or polypeptides of the present invention. There are in vitro and in vivo systems for production of polypeptides. Production systems that use eukaryotic cells or prokaryotic cells are examples of an in vitro production system.

Eukaryotic cells that can be used as host cells include, for example, animal cells, plant cells, and fungal cells. Animal cells include: mammalian cells, for example, CHO (J. Exp. Med. (1995) 108, 945), COS, HEK293, 3T3, myeloma, BHK (baby hamster kidney), HeLa, and Vero; amphibian cells such as *Xenopus laevis* oocytes (Valle, et al., Nature (1981) 291: 338-340); and insect cells such as Sf9, Sf21, and Tn5. For expressing the antibodies of the present invention, CHO-DG44, CHO-DX11B, COS7 cells, HEK293 cells, and BHK cells can be suitably used. Of the animal cells, CHO cells are particularly preferable for large-scale expression. Vectors can be introduced into a host cell by, for example, calcium phosphate methods, DEAE-dextran methods, methods using cationic liposome DOTAP (Boehringer-Mannheim), electroporation methods, or lipofection methods.

It is known that plant cells such as *Nicotiana tabacum*-derived cells and *Lemna minor* cells are protein production systems, and these cells can be used to produce antibodies of the present invention by methods that culture calluses from these cells. Protein expression systems that use fungal cells including yeast cells, for example, cells of the genus *Saccharomyces* (*Saccharomyces cerevisiae*, *Saccharomyces pombe*, etc.), and cells of filamentous fungi, for example, the genus *Aspergillus* (*Aspergillus niger*, etc.) are known, and these cells can be used as a host to produce antibodies of the present invention.

When prokaryotic cells are used, production systems that use bacterial cells are available. Production systems that use bacterial cells including *Bacillus subtilis* as well as *E. coli* described above are known, and they can be used to produce antibodies of the present invention.

When an antibody is produced using a host cell of the present invention, a polynucleotide encoding an antibody of the present invention may be expressed by culturing the host cell transformed with an expression vector comprising the polynucleotide. Culturing can be performed according to known methods. For example, when animal cells are used as a host, DMEM, MEM, RPMI 1640, or IMDM may be used as the culture medium. The culture medium may be used with serum supplement solutions such as FBS or fetal calf serum (FCS). Alternatively, cells can be cultured in serum-free cultures. The preferred pH is about 6 to 8 during the course of culturing. Incubation is carried out typically at about 30 to 40° C. for about 15 to 200 hours. Medium is exchanged, aerated, or agitated, as necessary.

On the other hand, systems for producing polypeptides in vivo include, for example, those using animals and those using plants. A polynucleotide of interest is introduced into an animal or plant to produce the polypeptide in the body of the animal or the plant, and then the polypeptide is collected. The "host" of the present invention includes such animals and plants.

When animals are used, production systems that use mammals or insects are available. Mammals such as goat, pig, sheep, mouse, and cattle may be used (Vicki Glaser, SPECTRUM Biotechnology Applications (1993)). When mammals are used, transgenic animals may be used.

For example, a polynucleotide encoding a antibody of the present invention may be prepared as a fusion gene with a gene encoding a polypeptide specifically produced in milk, such as goat β-casein. Next, polynucleotide fragments containing this fusion gene are injected into goat embryos, which are then introduced back into female goats. The antibody of interest can be obtained from milk produced by the transgenic goats, which are born from the goats that received the embryos, or by their offspring. Appropriate hormones may be administered to the transgenic goats to increase the volume of milk containing the antibody produced by the transgenic goats (Ebert et al., Bio/Technology (1994) 12: 699-702).

Insects such as silkworms may be used for producing antibodies of the present invention. When silkworms are used, baculoviruses carrying a polynucleotide encoding an antibody of interest can be used to infect silkworms, so that the antibody of interest can be obtained from the body fluids of these silkworms (Susumu et al., Nature (1985) 315:592-594).

Plants used for producing antibodies of the present invention include, for example, tobacco. When tobacco is used, a polynucleotide encoding an antibody of interest is inserted into a plant expression vector, for example, pMON 530, and then the vector is introduced into a bacterium such as *Agrobacterium tumefaciens*. The bacteria are then used to infect tobacco such as *Nicotiana tabacum*, and the desired antibody can be obtained from the leaves of the tobacco (Ma et al., Eur. J. Immunol. (1994) 24: 131-138). Alternatively, the same bacteria can be used to infect *Lemna minor*, and after cloning, the desired antibody can be obtained from the cells of *Lemna minor* (Cox K. M. et al., Nat. Biotechnol. 2006 December; 24(12):1591-1597).

The antibody thus obtained may be isolated from the inside or outside (such as the medium and milk) of host cells, and purified as a substantially pure and homogenous antibody. Methods used for separating and purifying an antibody are not limited, and methods used in standard polypeptide purification may be applied. Antibodies may be isolated and purified by selecting an appropriate combination of, for example, chromatographic columns, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

Chromatographies include, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., (1996) Cold Spring Harbor Laboratory Press). These chromatographies can be carried out using liquid phase chromatography such as HPLC and FPLC. Examples of columns for affinity chromatography include protein A columns and protein G columns. Examples of the columns that use protein A include Hyper D, POROS, and Sepharose F. F. (Pharmacia).

An antibody can be modified arbitrarily, and peptides can be deleted partially from the antibody by treatment with an appropriate protein modifying enzyme before or after antibody purification, as necessary. Such protein modifying enzymes include, for example, trypsins, chymotrypsins, lysyl endopeptidases, protein kinases, and glucosidases.

Another preferred embodiment of the present invention includes a method for producing a multispecific antibody of the present invention, wherein the method comprises the steps of culturing the host cells of the present invention as described above and collecting the polypeptide from the cell culture.

In the present invention, the term "multispecific antibody" refers to an antibody that can specifically bind to at least two different types of antigens. Examples of preferred multispecific antibodies obtained by the production methods or purification methods of the present invention include bispecific antibodies (BsAbs) (also called dual-specificity antibodies) that can specifically bind to two antigens.

In the present invention, the term "different antigens" does not necessarily mean that the antigens themselves are different, and may mean that the epitopes are different. Therefore, for example, different epitopes within a single molecule are also included in the "different antigens" of the present invention. In the present invention, two antibodies that recognize different epitopes within a single molecule are regarded as antibodies that recognize different antigens.

The multispecific antibodies of the present invention are antibodies having specificity to two or more different antigens, or molecules comprising fragments of such antibodies.

In the above-mentioned methods of the present invention, the phrase "modification of nucleic acids" comprises modification of nucleic acids that results in separated peaks of a first polypeptide and a second polypeptide by standard chromatography analysis.

In the methods of the present invention, the phrase "modification of nucleic acids" refers to modifying nucleic acids that correspond to the amino acid residues that are introduced by "modification" of the present invention. More specifically, the phrase refers to altering nucleic acids encoding the original amino acid residues (before modification) to nucleic acids encoding amino acid residues that are introduced by the modification.

Usually, the phrase means gene manipulation or mutagenesis that modifies the original nucleic acids by inserting, deleting, or substituting at least one nucleotide, to produce a codon that encodes an amino acid residue of interest. More specifically, a codon encoding the original amino acid residue is replaced by a codon encoding the amino acid residue to be introduced by the modification. Such nucleic acid modifications can be carried out appropriately by those skilled in the art using known techniques, for example, site-directed mutagenesis or PCR mutagenesis.

The modification positions in the present invention include, for example, (1) amino acid residues on the surface of a polypeptide, (2) amino acid residues in the variable region, preferably in the FR region, and (3) amino acid residues in the constant region.

"Amino acids on the surface of a polypeptide" are amino acids whose side chains can contact solvent molecules (usually water molecules). It is not necessary for the entire side chain to be in contact with solvent molecules, and even if only part of the side chain is in contact with solvent molecules, the amino acid is considered to be an amino acid on surface. Those skilled in the art can produce homology models of polypeptides or antibodies by homology modeling and such using commercially available software, and thereby selecting appropriate residues as amino acids on the surface.

Those skilled in the art can suitably select surface amino acids in the antibody variable region using homology models produced by homology modeling and such. For example, in the H chain FR region, H1, H3, H5, H8, H10, H12, H13, H15, H16, H19, H23, H25, 126, H39, H42, H43, H44, H46, H68, H71, H72, H73, H75, H76, H81, H82b, H83, H85, H86, H105, H108, H110, and H112 are examples of surface amino acids. However, the surface amino acids of the present invention are not limited thereto. For the H chain CDR region, surface amino acids can be similarly selected using homology models. For example, H97 is exposed to the surface in most antibodies. In the L chain FR region, L1, L3, L7, L8, L9, L11, L12, L16, L17, L18, L20, L22, L38, L39, L41, L42, L43, L45, L46, L49, L57, L60, L63, L65, L66, L68, L69, L70, L74, L76, L77, L79, L80, L81, L85, L100, L103, L105, L106, L107, and L108 are examples of surface amino acids. However, the surface amino acids of the present invention are not limited thereto. Furthermore, for the L chain CDR region, surface amino acids can be similarly selected using homology models.

In the present invention, amino acid residues in the variable region include amino acid residues in the heavy chain variable region (VH) or light chain variable region (VL), and are preferably amino acid residues in the framework region (FR).

In the present invention, surface-exposed amino acids other than those in CDR are, for example, H10, H12, H23, H39, H43, and H105 in the FR region, but are not limited thereto.

In the present invention, polypeptides with nucleic acid modification are preferably a homomultimer of a first polypeptide, a homomultimer of a second polypeptide, and a heteromultimer of the first polypeptide and second polypeptide. As described in the Examples below, the homomultimer of a first polypeptide is, for example, a homodimer of the humanized A69-H chain and humanized BBA-L chain; a homomultimer of a second polypeptide is, for example, a homodimer of the humanized B26-H chain and humanized BBA-L chain; and a heteromultimer of a first polypeptide and a second polypeptide is, for example, a heterodimer of the humanized A69-H chain, humanized B26-H chain, and humanized BBA-L chain. However, the polypeptides are not limited thereto.

Examples of standard chromatography in the present invention include cation exchange chromatography, anion exchange chromatography, hydrophobic chromatography, hydroxyapatite chromatography, hydrophobic charge interaction chromatography, and chromatofocusing.

In the above-mentioned methods of the present invention, a first polypeptide and a second polypeptide preferably comprise a heavy chain variable region (VH). The variable region may comprise, for example, a complementary determining region (CDR) and a framework region (FR).

The number of amino acid residues that undergo modification in the methods of the present invention is not particularly limited. However, for example, when the variable region(s) of an antibody is modified, it is preferable that for the separation of polypeptides of interest, the number of modified amino acid residues be kept to the minimum as necessary, so as not to decrease the antigen binding activity or increase the antigenicity of the antibody.

In order to not increase the antigenicity, the amino acid sequences after modification in the present invention are preferably human sequences, but are not limited thereto. Furthermore, in order to turn each of the modified FRs (FR1, FR2, FR3, and FR4) into a human sequence, mutations may be introduced into positions other than those that have been modified for alteration of isoelectric point. The method of replacing each FR with a human sequence in this manner has been reported in a Non-Patent Document (Ono K. et al., Mol. Immunol. 1999 April; 36(6):387-395). Furthermore, to alter the isoelectric point of each FR, the FR can be modified into another human FR having a different isoelectric point (for example, FR3 can be replaced with another human FR having a lower isoelectric point). Such a humanization method has been reported in a Non-Patent Document (Dall'Acqua W F., Methods. 2005 May; 36(1):43-60).

Furthermore, when separation of the polypeptides of interest cannot be achieved by slight modifications to the surface charge, the desired multispecific antibody can be obtained by repeating modification of surface charge and evaluation of polypeptide separation.

Furthermore, in the above-mentioned methods of the present invention, a multispecific antibody preferably comprises a third polypeptide comprising a light chain variable region, and preferably, the first polypeptide and the second polypeptide each forms a multimer with the third polypeptide.

Additionally, in the above-mentioned methods of the present invention, a first polypeptide and a second polypeptide preferably comprise a heavy chain constant region that preferably generates different pIs for the first polypeptide and second polypeptide. Examples of such heavy chain constant regions include heavy chain constant regions of antibodies having different pIs. The pI difference can be introduced into the first polypeptide and the second polypeptide using the heavy chain constant regions of IgG1, IgG2, IgG3, or IgG4 which have pIs that are originally different from each other. Alternatively, the amino acids in the heavy chain constant regions of the first polypeptide and the second polypeptide that cause differences in isoelectric point among these subclasses can be modified alone, or in combination with adjacent amino acids that do not have any effect on the isoelectric points to generate non-wild-type human constant regions, and pI difference can be introduced into the two constant regions. Examples of positions to be modified for introducing pI difference into the constant regions include, for example, positions 137, 196, 203, 214, 217, 233, 268, 274, 276, 297, 355, 392, 419, and 435, EU numbering, in the H chain constant region.

Furthermore, since removal of sugar chains from a heavy chain constant region generates pI difference, position 297, which is a glycosylated site, is another example of a position to be modified for introducing pI difference.

For methods that comprise the above-mentioned first polypeptide and second polypeptide comprising a heavy chain constant region, methods that combine with the method in which the above-mentioned first polypeptide and second polypeptide comprise a heavy chain variable region, and/or the method in which the multispecific antibody comprises a third polypeptide comprising a light chain variable region, and a first polypeptide and a second polypeptide that each forms a multimer with the third polypeptide, are included in the present invention.

Multispecific antibodies produced by the above-mentioned methods are also included in the present invention.

Furthermore, in an embodiment, when the first polypeptide in the multispecific antibody provided by the present invention comprises a heavy chain variable region and/or a heavy chain constant region, at least one amino acid residue in the region is made to carry a charge so that "the isoelectric points will be different". For example, the amino acid residue(s) is selected from amino acid residues at positions 10, 12, 23, 39, 43, and 105, Kabat numbering, in the heavy chain variable region, or amino acid residues at positions 137, 196, 203, 214, 217, 233, 268, 274, 276, 297, 355, 392, 419, and 435, EU numbering, in the heavy chain constant region. Of the amino acid residues of the first polypeptide indicated by the above-mentioned numbering, amino acid residues other than the charged amino acid residue may have the same type of charge as that of the charged amino acid residue, or may be uncharged, or may have the opposite charge of that of the charged amino acid residue, as long as the isoelectric point of the first polypeptide and that of the second polypeptide are different.

The above-mentioned multispecific antibodies of the present invention comprise a second polypeptide that preferably has the opposite charge of that of the charged amino acid residue in the first polypeptide, or is uncharged. More specifically, the second polypeptide in the multispecific antibodies comprises a heavy chain variable region and/or a heavy chain constant region, and at least one amino acid residue in the region is uncharged or has the opposite charge of that of the amino acid residue selected to carry a charge in the heavy chain variable region and/or the heavy chain constant region in the first polypeptide. The amino acid residue(s) is selected from amino acid residues at positions 10, 12, 23, 39, 43, and 105, Kabat numbering, in the heavy chain variable region, or amino acid residues at positions 137, 196, 203, 214, 217, 233, 268, 274, 276, 297, 355, 392, 419, and 435, EU numbering, in the heavy chain constant region. Of the amino acid residues of the second polypeptide indicated by the above-mentioned numbering, amino acid residues other than the charged amino acid residue may have the same type of charge as that of the charged amino acid residue, or may be uncharged, or may have the opposite charge of that of the charged amino acid residue, as long as the isoelectric point of the first polypeptide and that of the second polypeptide are different.

To lower isoelectric points, it is desirable to apply, for example, an IgG2 or IgG4 sequence to position 137, an IgG1, IgG2, or IgG4 sequence to position 196, an IgG2 or IgG4 sequence to position 203, an IgG2 sequence to position 214, an IgG1, IgG3, or IgG4 sequence to position 217, an IgG1, IgG3, or IgG4 sequence to position 233, an IgG4 sequence to position 268, an IgG2, IgG3, or IgG4 sequence to position 274, an IgG1, IgG2, or IgG4 sequence to position 276, an IgG4 sequence to position 355, an IgG3 sequence to position 392, an IgG4 sequence to position 419, and an IgG1, IgG2, or IgG4 sequence to position 435. To increase isoelectric points, it is desirable to apply, for example, an IgG1 or IgG3 sequence to position 137, an IgG3 sequence to position 196, the IgG1 or IgG3 sequence to position 203, an IgG1, IgG3, or IgG4 sequence to position 214, an IgG2 sequence to position 217, an IgG2 sequence to position 233, an IgG1, IgG2, or IgG3 sequence to position 268, an IgG1 sequence to position 274, an IgG3 sequence to position 276, an IgG1, IgG2, or IgG3 sequence to position 355, an IgG1, IgG2, or IgG4 sequence to position 392, an IgG1, IgG2, or IgG3 sequence to position 419, and an IgG3 sequence to position 435.

It is not necessary to apply all of these sequences, as long as there is sufficient difference between the isoelectric points of the two H chains.

Some amino acids are known to be charged amino acids. Generally, lysine (K), arginine (R), and histidine (H) are known as positively charged amino acids (cationic amino acids). Aspartic acid (D), glutamic acid (E), and such are known as negatively charged amino acids (anionic amino acids).

Preferably, the above-mentioned "charged amino acid residues" are suitably selected from amino acid residues included in either one of groups (a) and (b) below, but are not particularly limited thereto:
(a) glutamic acid (E), and aspartic acid (D); and
(b) lysine (K), arginine (R), and histidine (H).

Regarding the above-mentioned antibodies, the phrase "having the same type of charge" means, for example, that the above-mentioned amino acid residue in the heavy chain variable region according to Kabat numbering and the above-mentioned amino acid residue in the heavy chain constant region according to EU numbering both carry an amino acid residue included in either one of the above-mentioned groups (a) and (b).

The phrase, "having the opposite charge" means that, for example, at least one of the above-mentioned amino acid residues, by Kabat numbering or EU numbering, in the second polypeptide comprising a heavy chain variable region and/or a heavy chain constant region is included in either one of the above-mentioned groups (a) or (b), and its corresponding amino acid residue at a position in the heavy chain variable region and/or heavy chain constant region comprised in the first polypeptide is included in the other group.

More specifically, the present invention provides multi-specific antibodies, in which the above-mentioned amino acid residues having the same type of charge are selected from the amino acid residues included in either one of the above-mentioned group (a) or (b).

In a preferred embodiment of the present invention, if the original amino acid residue (before modification) is already charged, it may be modified to be an uncharged amino acid residue.

In the present invention, an amino acid residue is preferably modified such that the isoelectric point (pI) of the first polypeptide and that of the second polypeptide will be different. Furthermore, when multiple amino acid residues are introduced by modification, a few uncharged amino acid residues may be included in these amino acid residues.

Furthermore, the present invention provides multispecific antibodies, wherein the variable region of the first polypeptide comprises the amino acid sequence of any one of (a1) to (a7) below, wherein the variable region of the second polypeptide comprises the amino acid sequence of any one of (b1) to (b3) below, and wherein the variable region of the third polypeptide comprises the amino acid sequence of (c1) or (c2) below:
(a1) SEQ ID NO: 7
(a2) SEQ ID NO: 8
(a3) SEQ ID NO: 9
(a4) SEQ ID NO: 10
(a5) SEQ ID NO: 11
(a6) SEQ ID NO: 12
(a7) SEQ ID NO: 13
(b1) SEQ ID NO: 14
(b2) SEQ ID NO: 15
(b3) SEQ ID NO: 16
(c1) SEQ ID NO: 17
(c2) SEQ ID NO: 18

The above amino acid sequences are specific examples of the amino acids subjected to modification in the present invention. However, the variable regions are not limited to those comprising these amino acids.

A preferred embodiment of the above-mentioned multispecific antibodies is, for example, a multispecific antibody, wherein the variable region of the first polypeptide comprises the amino acid sequence of SEQ ID NO: 11, wherein the variable region of the second polypeptide comprises the amino acid sequence of SEQ ID NO: 16, and wherein the variable region of the third polypeptide comprises the amino acid sequence of SEQ ID NO: 17.

Another preferred embodiment is, for example, a multispecific antibody, wherein the variable region of the first polypeptide comprises the amino acid sequence of SEQ ID NO: 12, wherein the variable region of the second polypeptide comprises the amino acid sequence of SEQ ID NO: 16, and wherein the variable region of the third polypeptide comprises the amino acid sequence of SEQ ID NO: 18.

A further preferred embodiment of the above-mentioned multispecific antibody is a multispecific antibody, wherein the first polypeptide and the second polypeptide comprise the human IgG4 constant region, and wherein the third polypeptide comprises the human κ constant region.

Herein, the term "antibody" is used in the broadest sense, and includes monoclonal antibodies, polyclonal antibodies, and mutant antibodies, such as chimeric antibodies, humanized antibodies, minibodies (including antibody fragments), and multispecific antibodies, as long as they display a desired biological activity. In the present invention, the methods of antibody modification of the present invention can be used favorably on these antibodies when they are obtained (produced).

The "antibodies" of the present invention include antibodies in which the charge of amino acid residues has been modified as described above, and whose amino acid sequences have been further modified by amino acid substitutions, deletions, additions, and/or insertions. The antibodies also include antibodies whose amino acid sequences have been modified by amino acid substitution, deletion, addition, and/or insertion, or chimerization, humanization, or such, and in which the charge of amino acid residues has been further modified. In short, modifications may be performed at the same time when mouse antibodies are humanized, or further modifications may be performed on humanized antibodies.

Amino acid sequence modifications, such as amino acid substitutions, deletions, additions, and/or insertions, and humanization and chimerization, can be achieved by methods known to those skilled in the art. When the antibodies of the present invention are prepared as recombinant antibodies, likewise, the amino acid sequences of the antibody variable and constant regions may also be modified by amino acid substitutions, deletions, additions, and/or insertions, or chimerization, humanization and the like.

The antibodies of the present invention may be derived from any animal, such as a mouse, human, rat, rabbit, goat, or camel. Furthermore, the antibodies may be modified, for example, chimeric antibodies, and in particular, modified antibodies that include amino acid substitutions in their sequence, such as humanized antibodies. The antibodies may be any type of antibody, such as antibody modification products linked with various molecules, antibody fragments, and minibodies.

"Chimeric antibodies" are antibodies prepared by combining sequences derived from different animals. An example is an antibody having heavy and light chain variable (V) regions from a mouse antibody and heavy and light chain constant (C) regions from a human antibody. Chimeric antibodies can be prepared by known methods. To obtain such chimeric antibodies, for example, a DNA encoding an antibody V region may be ligated with a DNA encoding a human antibody C region; the resulting ligation product can be inserted into an expression vector; and the construct can be introduced into a host to produce the chimeric antibody.

"Humanized antibodies" are also referred to as reshaped human antibodies, and can be obtained by substituting the complementary determining region (CDR) of a human antibody for the CDR of an antibody derived from a nonhuman mammal, for example, a mouse. Methods for identifying CDRs are known in the art (Kabat et al., Sequence of Proteins of Immunological Interest (1987), National Institute of Health, Bethesda, Md.; Chothia et al., Nature (1989) 342:877). General genetic recombination techniques suitable for this purpose are also known (see European Patent Application EP 125023; and WO 96/02576). For example, the CDR of a mouse antibody can be determined by known methods, and a DNA can be prepared such that it encodes an antibody in which the CDR is ligated with the framework region (FR) of a human antibody. A humanized antibody can then be produced using a system that uses conventional expression vectors. Such DNAs can be synthesized by PCR, using as primers several oligonucleotides designed to include portions that overlap the ends of both the CDR and FR regions (see the method described in WO 98/13388). Human antibody FRs linked via CDRs are selected such that the CDRs form a suitable antigen binding site. If required, amino acids in the FRs of an antibody variable region may be substituted so that the CDRs of the reshaped human antibody can form a suitable antigen binding site (Sato, K. et al., Cancer Res. (1993) 53:851-856). Modifiable amino acid residues in the FRs include portions that directly bind to an antigen via non-covalent bonds (Amit et al., Science (1986) 233: 747-53), portions that have some impact or effect on the CDR structure (Chothia et al., J. Mol. Biol. (1987) 196: 901-17), and portions involved in the interaction between VH and VL (EP 239400).

When the antibodies of the present invention are chimeric antibodies or humanized antibodies, the C regions of these antibodies are preferably derived from human antibodies.

For example, Cγ1, Cγ2, Cγ3, and Cγ4 can be used for the H chain, while Cκ and Cλ can be used for the L chain. Meanwhile, the human antibody C region may be modified as required to improve antibody or production stability. A chimeric antibody of the present invention preferably includes a variable region of an antibody derived from a nonhuman mammal and a constant region of a human antibody. A humanized antibody preferably includes CDRs of an antibody derived from a nonhuman mammal and FRs and C regions of a human antibody. The constant regions of the human antibodies include specific amino acid sequences, which vary depending on the isotype of the antibody, for example, IgG (IgG1, IgG2, IgG3, and IgG4), IgM, IgA, IgD, and IgE. The constant regions used to prepare the humanized antibodies of the present invention may be the constant regions of antibodies of any isotype. A constant region of human IgG is preferably used, although the invention is not limited thereto. The FRs derived from a human antibody, which are used to prepare the humanized antibodies, are not particularly limited, and thus may be derived from an antibody of any isotype.

The variable and constant regions of chimeric or humanized antibodies of the present invention may be modified by deletion, substitution, insertion, and/or addition, so long as the antibodies exhibit the same binding specificity as that of the original antibodies.

Since their antigenicity in the human body has been attenuated, chimeric and humanized antibodies using human-derived sequences are expected to find utility when administered to humans for therapeutic purposes or such.

In addition, minibodies are useful as the antibodies because of their in vivo kinetic characteristics and low-cost production using *E. coli*, plant cells, or such.

Antibody fragments are one type of minibody. The term "minibodies" includes antibodies that include an antibody fragment as a partial structural unit. The minibodies of the present invention are not particularly limited by their structure nor their method of production, so long as they have antigen binding activity. Some minibodies have an activity greater than that of a whole antibody (Orita et al., Blood (2005) 105:562-566). Herein, the "antibody fragments" are not particularly limited, so long as they are a portion of a whole antibody (for example, whole IgG). However, the antibody fragments preferably include a heavy chain variable region (VH) or a light chain variable region (VL). Examples of preferred antibody fragments are: Fab, F(ab')$_2$, Fab', and Fv. The amino acid sequence of a VH or VL in an antibody fragment may be modified by substitution, deletion, addition, and/or insertion. Furthermore, some portions of a VH and VL may be deleted, so long as the resulting fragments retain their antigen binding ability. For example, of the antibody fragments described above, "Fv" is a minimal antibody fragment composed of the complete antigen recognition and binding sites. "Fv" is a dimer (VH-VL dimer) composed of one unit of VH and one unit of VL bound very strongly by non-covalent bonding. An antigen binding site is formed on the surface of the VH-VL dimer by the three complementary determining regions (CDRs) of each variable region. Six CDRs confer an antigen binding site to the antibody. However, even one variable region (or half of an Fv composed of only three antigen-specific CDRs) has the ability to recognize and bind to an antigen, although its affinity is lower than that of the complete binding site. Thus, molecules smaller than Fv are also included in the context of antibody fragments of the present invention. The variable regions of an antibody fragment may also be chimerized or humanized.

The minibodies preferably include both VH and VL. Examples of suitable minibodies include antibody fragments such as Fab, Fab', F(ab')2, and Fv, and scFv (single-chain Fv), which can be prepared using antibody fragments, (Huston et al., Proc. Natl. Acad. Sci. USA (1988) 85: 5879-83; Pluckthun "The Pharmacology of Monoclonal Antibodies" Vol. 113, Resenburg and Moore (eds.), Springer Verlag, New York, pp. 269-315, (1994)); diabodies (Holliger et al., Proc. Natl. Acad. Sci. USA (1993) 90:6444-8; EP 404097; WO93/11161; Johnson et al., Method in Enzymology (1991) 203: 88-98; Holliger et al., Protein Engineering (1996) 9:299-305; Perisic et al., Structure (1994) 2:1217-26; John et al., Protein Engineering (1999) 12(7):597-604; Atwell et al., Mol. Immunol. (1996) 33:1301-12); sc(Fv)2 (Hudson et al, J Immunol. Methods (1999) 231:177-89; Orita et al., Blood (2005) 105:562-566); triabodies (Journal of Immunological Methods (1999) 231: 177-89); and tandem diabodies (Cancer Research (2000) 60:4336-41).

An antibody fragment can be prepared by treating an antibody with an enzyme, for example, a protease such as papain or pepsin (see Morimoto et al., J. Biochem. Biophys. Methods (1992) 24: 107-17; Brennan et al., Science (1985) 229:81). Alternatively, antibody fragments can also be produced by genetic recombination based on its amino acid sequence.

A minibody having a structure that results from modification of an antibody fragment can be prepared using antibody fragments obtained by enzyme treatment or genetic recombination. Alternatively, after constructing a gene which encodes a whole minibody, and introducing the construct into an expression vector, the minibody may be expressed in appropriate host cells (see, for example, Co et al., J. Immunol. (1994) 152: 2968-76; Better and Horwitz, Methods Enzymol. (1989) 178: 476-96; Pluckthun and Skerra, Methods Enzymol. (1989) 178: 497-515; Lamoyi, Methods Enzymol. (1986) 121: 652-63; Rousseaux et al., Methods Enzymol. (1986) 121: 663-9; Bird and Walker, Trends Biotechnol. (1991) 9: 132-7).

The above described scFVs are single-chain polypeptides that include two variable regions linked together via a linker or such, as required. The two variable regions in an scFv are typically one VH and one VL, but an scFv may include two VH or two VL. In general, scFv polypeptides include a linker between the VH and VL domains, thereby forming a paired portion of VH and VL required for antigen binding. A peptide linker composed of ten or more amino acids is typically used as the linker between VH and VL when forming an intramolecular paired portion between VH and VL. However, the linkers of the scFv of the present invention are not limited to such peptide linkers, so long as they do not inhibit the formation of an scFv. To review scFv, see Pluckthun "The Pharmacology of Monoclonal Antibody", Vol. 113 (Rosenburg and Moore ed., Springer Verlag, NY, pp. 269-315 (1994)).

The term, "diabodies (Db)" refers to bivalent antibody fragments constructed by gene fusion (P. Holliger et al., Proc. Natl. Acad. Sci. USA 90: 6444-6448 (1993); EP 404,097; WO93/11161 and such). Diabodies are dimers composed of two polypeptide chains, wherein each polypeptide chain includes within the same chain a light chain variable region (VL) and a heavy chain variable region (VH) connected with a linker short enough to disable interaction of these two regions, for example a linker of about five amino acid residues. VL and VH encoded on the same polypeptide chain will form a dimer because the linker between VL and VH is too short to form a single chain V region fragment. Therefore, the resulting diabody has two antigen-binding sites. Herein, when VL and VH directed against two different epitopes (a and b) are expressed simultaneously as combinations of VLa-VHb and VLb-VHa connected with a linker of about five residues, they are secreted as bispecific Db.

Since diabodies include two molecules of scFvs, they thus composed of four variable regions, and as a result have two antigen binding sites. When the objective is to form a diabody, unlike as in the case with scFvs that do not form dimers, ordinarily, linkers forming a connection between VH and VL in each scFv molecules are linkers of about five amino acids when used as peptide linkers. However, scFv linkers for diabody formation are not limited to such peptide linkers so long as they do not interfere with scFv expression and diabody formation.

More preferably, in the present invention, an example of a multispecific antibody is a bispecific antibody.

The above-mentioned "bispecific antibody" may be, for example, an antibody having a structure in which a heavy chain variable region and a light chain variable region are linked in a single chain (for example, sc(Fv)2). The bispecific antibody may also be an antibody-like molecule (for example, scFv-Fc) produced by fusing an scFv (or sc(Fv)2), in which a heavy chain variable region and a light chain variable region are linked, to an Fc region (a constant region lacking the CH1 domain). A multispecific antibody consisting of scFv-Fc has an (scFv)2-Fc type structure with VH1-linker-VL1-Fc as the first polypeptide and VH2-linker-VL2-Fc as the second polypeptide. Alternatively, the bispecific antibody may be an antibody-like molecule in which a single domain antibody is linked with an Fc region (Curr. Opin. Drug Discov. Devel. 2006, 9(2), 184-93).

As for the genes encoding the H chain or L chain of antibodies before introduction of mutations by methods of the present invention (herein, it may be simply referred to as "an antibody of the present invention"), known sequences can be used, or they can be obtained by methods known to those skilled in the art. For example, they may be obtained from an antibody library, or they may be obtained by cloning genes encoding the antibody from hybridomas producing monoclonal antibodies.

Regarding antibody libraries, many antibody libraries are already well known, and since methods for producing antibody libraries are known, those skilled in the art can appropriately obtain antibody libraries. For example, regarding antibody phage libraries, one can refer to the literature such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 3245-60; Vaughan et al., Nature Biotechnology 1996, 14: 309-14; and Japanese Patent Kohyo Publication No. (JP-A) H20-504970 (unexamined Japanese national phase publication corresponding to a non-Japanese international publication). In addition, known methods, such as methods that use eukaryotic cells as libraries (WO95/15393) and ribosome display methods, may be used. Furthermore, techniques to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO92/01047, WO92/20791, WO93/06213, WO93/11236, WO93/19172, WO95/01438, and WO95/15388.

As for methods for obtaining genes encoding antibodies from hybridomas, known techniques may be used, involving the use of desired antigens or cells expressing the desired antigens as sensitizing antigens, using these to perform immunizations according to conventional immunization methods, fusing the immune cells thus obtained with known parent cells by ordinary cell fusion methods, screening monoclonal antibody producing cells (hybridomas) by ordinary screening methods, synthesizing cDNAs of antibody variable regions (V regions) from mRNAs of the obtained hybridomas using reverse transcriptase, and linking them with DNAs encoding the desired antibody constant regions (C regions).

More specifically, without being particular limited to the following examples, sensitizing antigens for obtaining the above-mentioned antibody genes encoding the H chains and L chains include both complete antigens with immunogenicity and incomplete antigens composed of haptens and such that do not show antigenicity. For example, full length proteins and partial peptides of proteins of interest can be used. In addition, it is known that substances composed of polysaccharides, nucleic acids, lipids, and such may become antigens. Thus, there are no particular limitations on antigens of the antibodies of the present invention. Antigens can be prepared by methods known to those skilled in the art, and they can be prepared, for example, by the following methods using baculoviruses (for example, WO98/46777). Hybridomas can be produced, for example, the following methods of Milstein et al. (G. Kohler and C. Milstein, Methods Enzymol. 1981, 73: 3-46), and such. When the immunogenicity of an antigen is low, it can be linked to a macromolecule that has immunogenicity, such as albumin, and then used for immunization. Furthermore, by linking antigens with other molecules if necessary, they can be converted into soluble antigens. When transmembrane molecules such as receptors are used as antigens, portions of the extracellular regions of the receptors can be used as a fragment, or cells expressing transmembrane molecules on their cell surface may be used as immunogens.

Antibody-producing cells can be obtained by immunizing animals using suitable sensitizing antigens described above. Alternatively, antibody-producing cells can be prepared by in vitro immunization of lymphocytes that can produce antibodies. Various mammals can be used as the animals for immunization, where rodents, lagomorphas and primates are generally used. Examples of such animals include mice, rats, and hamsters for rodents, rabbits for lagomorphas, and monkeys including the cynomolgus monkey, rhesus monkey, hamadryas, and chimpanzees for primates. In addition, transgenic animals carrying human antibody gene repertoires are also known, and human antibodies can be obtained by using these animals (see WO96/34096; Mendez et al., Nat. Genet. 1997, 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H1-59878 (examined, approved Japanese patent application published for opposition)). Furthermore, desired human antibodies can be obtained by immunizing transgenic animals carrying a complete repertoire of human antibody genes, with desired antigens (see WO93/12227, WO92/03918, WO94/02602, WO96/34096, and WO96/33735).

Animal immunization can be carried out by appropriately diluting and suspending a sensitizing antigen in Phosphate-Buffered Saline (PBS), physiological saline, or such, and forming an emulsion by mixing an adjuvant if necessary, followed by an intraperitoneal or subcutaneous injection into animals. After that, the sensitizing antigen mixed with Freund's incomplete adjuvant is preferably administered several times every four to 21 days. Antibody production can be confirmed by measuring the target antibody titer in animal sera using conventional methods.

Antibody-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, 1986, 59-103). When required, hybridoma cells can be cultured and grown, and the binding specificity of the antibody produced from these hybridomas can be measured using known analysis methods, such as immunoprecipitation, radioimmunoassay (RIA), and enzyme-linked immunosorbent assay (ELISA). Thereafter, hybridomas that produce antibodies of interest whose specificity, affinity, or activity has been determined can be subcloned by methods such as limiting dilution.

Next, genes encoding the selected antibodies can be cloned from hybridomas or antibody-producing cells (sensitized lymphocytes, and such) using probes that may specifically bind to the antibodies (for example, oligonucleotides complementary to sequences encoding the antibody constant regions). Cloning from mRNA using RT-PCR is also possible. Immunoglobulins are classified into five different classes, IgA, IgD, IgE, IgG, and IgM. These classes are further divided into several subclasses (isotypes) (for example, IgG-1, IgG-2, IgG-3, and IgG-4; IgA-1 and IgA-2; and such). H chains and L chains used in the present invention to produce antibodies are not particularly limited and may derive from antibodies belonging to any of these classes or subclasses; however, IgG is particularly preferred.

Herein, it is possible to modify H-chain-encoding genes and L-chain-encoding genes using genetic engineering techniques. Genetically modified antibodies, such as chimeric antibodies, humanized antibodies that have been artificially modified for the purpose of decreasing heterologous antigenicity and such against humans, can be appropriately produced if necessary for antibodies such as mouse antibodies, rat antibodies, rabbit antibodies, hamster antibodies, sheep antibodies, and camel antibodies. Chimeric antibodies are antibodies composed of a nonhuman mammal antibody H chain and L chain variable regions, such as mouse antibody, and the H chain and L chain constant regions of human antibody. They can be obtained by ligating the DNA encoding a variable region of a mouse antibody to the DNA encoding a constant region of a human antibody, incorporating them into an expression vector, and introducing the vector into a host for production of the antibody. A humanized antibody, which is also called a reshaped human antibody, can be synthesized by PCR from a number of oligonucleotides produced so that they have overlapping portions at the ends of DNA sequences designed to link the complementary determining regions (CDRs) of an antibody of a nonhuman mammal such as a mouse. The obtained DNA can be ligated to a DNA encoding a human antibody constant region. The ligated DNA can be incorporated into an expression vector, and the vector can be introduced into a host to produce the antibody (see EP239400 and WO96/02576). Human antibody FRs that are ligated via the CDR are selected when the CDR forms a favorable antigen-binding site. If necessary, amino acids in the framework region of an antibody variable region may be substituted such that the CDR of the reshaped human antibody forms an appropriate antigen-binding site (K. Sato et al., Cancer Res. 1993, 53: 851-856).

In addition to the humanization techniques described above, antibodies may be modified to improve their biological properties, for example, antigenic affinity. In the present invention, such modifications can be carried out using methods such as site-directed mutagenesis (see for example, Kunkel (1985) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, 99%, etc.), when compared to the amino acid sequence of the original antibody variable region. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. Generally, naturally-occurring amino acid residues are classified into groups based on the characteristics of their side chains: (1) hydrophobic: alanine, isoleucine, valine, methionine, and leucine; (2) neutral hydrophilic: asparagine, glutamine, cysteine, threonine, and serine; (3) acidic: aspartic acid, and glutamic acid; (4) basic: arginine, histidine, and lysine; (5) residues that affect the orientation of the chain: glycine, and proline; and (6) aromatic: tyrosine, tryptophan, and phenylalanine.

Ordinarily, a total of six complementary determining regions (CDRs; hypervariable regions) present in the H chain and L chain variable regions interact to form the antigen binding site(s) of an antibody. Even one of these variable regions is known to have the ability to recognize and bind to the antigen, although the affinity will be lower than when all binding sites are included. Therefore, antibody genes of the present invention encoding the H chain and L chain only have to encode fragment portions having each of the antigen binding sites of H chain and L chain, and polypeptides encoded by these genes only have to maintain affinity with the desired antigens.

For example, as described above, desired bispecific antibodies that actually have activities can be obtained efficiently by the methods of the present invention.

Heavy chain variable regions are generally composed of three CDR regions and four FR regions, as described above. In a preferred embodiment of the present invention, amino acid residues subjected to "modification" can be appropriately selected, for example, from amino acid residues in the CDR regions or FR regions. Generally, modification of amino acid residues in the CDR regions can decrease affinity towards antigens. Therefore, in the present invention, amino acid residues subjected to "modification" are not particularly limited, but are preferably appropriately selected from amino acid residues in the FR regions.

Furthermore, sequences that can be used as variable region FRs for antibodies in organisms such as human or mouse can be appropriately obtained by those skilled in the art using public databases. More specifically, amino acid sequence information of the FR regions can be obtained by means described later in the Examples.

All prior art references cited herein are incorporated by reference into this specification.

EXAMPLES

Herein below, the present invention will be specifically described with reference to the Examples, but it is not to be construed as being limited thereto.

Example 1

Humanization of Bispecific Antibodies Carrying a Hybrid L Chain

A bispecific antibody composed of a combination of the anti-Factor IXa antibody A69-VH, anti-Factor X antibody B26-VH, and hybrid L chain (BBA), which was the most effective in shortening the blood coagulation time in Japanese Patent Application No. 2005-112514, was humanized as follows.

1-1. Homology Search of Human Antibodies

A database was constructed by obtaining amino acid sequence data of human antibodies from the publicly disclosed in Kabat Database (ftp://ftp.ebi.ac.uk/pub/databases/kabat/) and IMGT Database (http://imgt.cines.fr/), and homology search was performed on the database for the mouse A69H chain variable region (amino acid sequence: SEQ ID NO: 19), mouse B26H chain variable region (amino acid sequence: SEQ ID NO: 20), and mouse BBA L chain variable region (amino acid sequence: SEQ ID NO: 21). The results confirmed that they have high homologies to the human antibody sequences below, and it was thus decided that they could be used as framework region (hereinafter referred to as FR) for humanized antibodies.

(1) A69H chain variable region: KABATID-000064 (Kabat Database) (Kipps et al., J. Clin. Invest. 1991; 87:2087-2096)
(2) B26H chain variable region: EMBL Accession No. AB063872 (IMGT Database) (Unpublished Data)
(3) BBA L chain variable region: KABATID-024300 (Kabat Database) (Welschof et al., J. Immunol. Method. 1995; 179:203-214)

The complementary determining region (hereinafter referred to as CDR) of each of the mouse antibodies was grafted into the FR of human antibodies of (1)-(3), and humanized antibodies were thus prepared.

Moreover, the homology search web site publicly disclosed by NCBI (http://www.ncbi.nlm.nih.gov/BLAST/) was used to search for secretory signal sequences of human antibodies that are highly homologous to human antibodies of (4)-(6). The following secretory signal sequences obtained by the search were used.

(4) A69H chain variable region: GenBank Accession No. AF062257
(5) B26H chain variable region: GenBank Accession No. ACC18248
(6) BBA L chain variable region: GenBank Accession No. AAA59100

1-2. Construction of Humanized Antibody Gene Expression Vectors

For a nucleotide sequence encoding the amino acid sequence covering from the secretory signal sequence to the antibody variable region, twelve synthetic oligo-DNAs of about 50 bases were prepared, such that about 20 bases at the 3' end hybridize with each other. The synthetic oligo-DNAs were designed such that they encode a human sequence at the 5' side and a mouse sequence at the 3' side, or such that all the nucleotides encode a human sequence. Furthermore, a primer that anneals to the 5'-end of an antibody variable region gene and has the XhoI cleavage sequence, and a primer that encodes the 5'-end sequence of the intron sequence, anneals to the 3'-end of an antibody variable region gene, and has the SfiI cleavage sequence were prepared.

1 µL each of synthetic oligo-DNAs prepared at 2.5 µM were mixed, and 1×TaKaRa Ex Taq Buffer, 0.4 mM dNTPs, and 0.5 unit of TaKaRa Ex Taq (all from Takara) were added to prepare a 48 µL reaction solution. After heating at 94° C. for five minutes, two cycles of reaction at 94° C. for two minutes, 55° C. for two minutes, and 72° C. for two minutes were carried out to assemble and elongate each of the synthetic oligo-DNAs. Next, 1 µL (10 µM each) each of the primers that anneal to the 5' end and 3' end of the antibody gene were added, and the antibody variable region gene was amplified by 35 cycles of reaction at 94° C. for 30 seconds, 55° C. for 30 seconds, and 72° C. for one minute, and then reaction at 72° C. for five minutes. After PCR was carried out, the whole amount of the reaction solution was subjected to 1% agarose gel electrophoresis. Amplified fragments of the desired size (about 400 bp) were purified using the QIAquick Gel Extraction Kit (QIAGEN) according to the method described in the attached instruction manual, and eluted with 30 µL of sterilized water. The fragments were cloned using the pGEM-T Easy Vector System (Promega) according to the method described in the attached instruction manual. The nucleotide sequence of each DNA fragment was determined using the BigDye Terminator Cycle Sequencing Kit (Applied Biosystems) and ABI PRISM 3730xL DNA Sequencer or ABI PRISM 3700 DNA Sequencer (Applied Biosystems) according to the method described in the attached instruction manual.

The H-chain variable region fragment-inserted plasmid was digested with XhoI and SfiI, and the L-chain variable region fragment-inserted plasmid was digested with EcoRI, after they were confirmed to have the correct humanized antibody variable region gene sequence. Then, the reaction solutions were subjected to 1% agarose gel electrophoresis. DNA fragments having the desired size (about 400 bp) were purified using the QIAquick Gel Extraction Kit (QIAGEN) according to the method described in the attached instruction manual, and eluted with 30 µL of sterilized water. Thereafter, vectors for expression in animal cells were prepared as follows. To preferentially express IgG4 with H chains of a heterologous combination, an IgG4 that has amino acid substitution in its CH3 portion was used by referring to the knobs-into-holes technique for IgG1 (Merchant A M et al., Nature Biotechnology, 1998, Vol. 16, p. 677-681). Furthermore, to promote H-chain dimer formation, amino acid substitution (-ppcpScp-→-ppcpPcp-) was also introduced into the hinge. Humanized A69H chain expression vector was prepared by inserting the humanized A69H chain variable region antibody gene fragment into an expression vector prepared by inserting an Y349C and T366W-substituted constant region gene into pCAGGS comprising a chicken β-actin promoter (Niwa et al., Gene, 1991, 108: 193-199). Humanized B26H chain expression vector was prepared by inserting the humanized B26H chain variable region antibody gene fragment into an expression vector prepared by inserting an E356C, T366S, L368A, and Y407V-substituted constant region gene to pCAGGS. The plasmid (pCAG-gκcDNA) was prepared by inserting a wild-type antibody L chain constant region into pCAGGS, and was digested with EcoRI to prepare an expression vector into which the humanized BBA L chain variable region antibody gene fragment was inserted. Ligation reaction was performed using the Rapid DNA Ligation Kit (Roche Diagnostics), and the E. coli strain DH5α (TOYOBO) was transformed.

1-3. Expression of Humanized Bispecific Antibodies

Humanized bispecific antibodies were expressed using the following method. Human fetal renal carcinoma cell-derived humanized bispecific antibodies were expressed using the method described in Example 1-2, or using the following method. Human fetal renal carcinoma cell-derived HEK293H strain (Invitrogen) was suspended in a DMEM medium (Invitrogen) containing 10% Fetal Bovine Serum (Invitrogen), seeded at a cell density of $5-6 \times 10^5$ cells/mL (10 mL per dish) in dishes used for adhesive cells (10-cm diameter, CORNING), and cultured for one day and night in a $CO_2$ incubator (37° C., 5% $CO_2$). Then, the medium was removed by suction, and 6.9 mL of CHO-S-SFM-II (Invitrogen) medium containing 1% Fetal Bovine Serum (Invitrogen) was added. The plasmid DNA mixture solution prepared in 1-2 (total of 13.8 µg) was mixed with 20.7 µL of 1 µg/mL Polyethylenimine (Polysciences Inc.) and 690 µL of CHO-S-SFMII medium, left to stand at room temperature for ten minutes, and then added to the cells in each dish. The cells were then incubated in a $CO_2$ incubator (37° C., 5% $CO_2$) for four to five hours. Then, 6.9 mL of CHO-S-SFM-II (Invitrogen) medium containing 1% Fetal Bovine Serum (Invitrogen) was added and then the cells were incubated in a $CO_2$ incubator for three days. The culture supernatant was collected, then cells were removed by centrifugation (at approximately 2000 g for five minutes at room temperature), and the solution was sterilized by passing it through a 0.22 µm filter MILLEX®-GV (Millipore). The sample was stored at 4° C. until use.

1-4. Purification of Humanized Bispecific Antibodies

100 µL of rProtein A Sepharose™ Fast Flow (Amersham Biosciences) was added to the culture supernatant obtained by the method described in Example 1-2, and the solution was mixed by rotation at 4° C. for four hours. The solution was transferred to an Ultrafree®-MC 0.22-µm filter cup (Millipore). After three washes with 500 µL of TBS containing 0.01% Tween® 20, the rProtein A Sepharose™ resin was suspended in 100 µL of 50 mM aqueous sodium acetate solution containing 0.01% Tween® 20 at pH 3.3, and left to stand for two minutes, and then, the antibody was eluted. The eluate was immediately neutralized by adding 6.7 µL of 1.5 M Tris-HCl, pH 7.8.

1-5. Quantification of Humanized Bispecific Antibody Concentration

Measurements were performed by two methods described below.

Goat anti-human IgG (Biosource International) was adjusted to 1 µg/mL with a coating buffer, and immobilized to a Nunc-Immuno plate (Nunc). After blocking with a diluent buffer (D.B.), a sample of the culture supernatant suitably diluted with D.B. was added. Furthermore, eleven three-fold serial dilutions of human IgG4 (humanized anti-TF antibody, see WO 99/51743) starting from 2000 ng/mL were made with D.B., and added as a standard for antibody concentration calculation. After three washes, goat anti-human IgG, alkaline phosphatase (Biosource International) was added for reaction. After five washes, the color was developed using Sigma 104® phosphatase substrate (Sigma-Aldrich) as a substrate, and the absorbance at 405 nm was measured on an absorbance reader Model 3550 (Bio-Rad Laboratories) with a reference wavelength of 655 nm. Using the Microplate Manager III (Bio-Rad Laboratories) software, human IgG concentration in the culture supernatant was calculated from the standard curve.

Alternatively, measurements were performed with Biacore 1000 (BIACORE) using Protein A-immobilized Sensor Chip CM5 (BIACORE). More specifically, according to the manufacturer's protocol, an activated sensor chip was reacted with Protein A (SIGMA) solution diluted to 50 µg/mL with 10 mM aqueous sodium acetate solution (pH 4.0, BIACORE) at 5 µL/minute for 30 minutes, and then a blocking procedure was carried out to produce a Protein A-immobilized sensor chip. This sensor chip was used to measure the concentrations of the culture supernatant and the purified products on Biacore 1000 (BIACORE). HBS-EP Buffer (BIACORE) was used for the immobilization of the sensor chip and for the concentration measurements. Six two-fold serial dilutions of a humanized IgG4 antibody (humanized anti-TF antibody, see WO99/51743) starting from 4000 ng/mL were made with HBS-EP Buffer, and used as a standard for the concentration measurements.

1-6. Blood Coagulation Activity Assay for Humanized Bispecific Antibodies

To determine whether a bispecific antibody is capable of correcting the coagulation ability of hemophilia A blood, effects of the antibody on the activated partial thromboplastin time (APTT) were determined using Factor VIII-deficient plasma. 50 µL of an antibody solution at a variety of concentrations, 50 µL of Factor VIII-deficient plasma (Biomerieux), and 50 µL of the APTT reagent (Dade Behring) were mixed and heated at 37° C. for three minutes. Coagulation reaction was initiated by adding 50 µL of 20 mM $CaCl_2$ (Dade Behring) to the mixture. The time period until coagulation was measured with KC10A (Amelung) linked to CR-A (Amelung).

Using a calibration curve produced by defining the coagulation time of Factor VIII-deficient plasma as 0% and the coagulation time of normal plasma as 100%, the Factor VIII-like activity (%) of a bispecific antibody was calculated from the coagulation time measured when the bispecific antibody was added.

1-7. Acquisition of Humanized Bispecific Antibodies Having Blood Coagulation Activity The human antibody FR of humanized bispecific antibodies that displayed decreased blood coagulation ability in the above-mentioned blood coagulation activity assay were subjected to amino acid modification in order to increase the activity. More specifically, the QuikChange Site-Directed Mutagenesis Kit (Stratagene) was used to introduce mutations into the humanized antibody variable region according to the method described in the attached instruction manual. The H-chain variable region fragment-inserted plasmid digested with XhoI and SfiI, and the L-chain variable region fragment-inserted plasmid was digested with EcoRI, after they were confirmed to have the desired humanized antibody variable region gene sequence. Then, the reaction solutions were subjected to 1% agarose gel electrophoresis. DNA fragments having the desired size (about 400 bp) were purified using the QIAquick Gel Extraction Kit (QIAGEN) according to the method described in the attached instruction manual, and eluted with 30 µL of sterilized water. Then, plasmids for expression in animal cells were prepared according to the method described in Example 1-2. Humanized bispecific antibodies were prepared according to the method described in Examples 1-3, 1-4, and 1-5, and blood coagulation activity was evaluated according to the method described in Example 1-6.

By repeating amino acid modifications of the FR sequence and assessment of blood coagulation ability, a humanized bispecific antibody (humanized A69 (hA69a)/humanized B26 (hB26-F123e4)/humanized BBA (hAL-F123j4)) having the same level of activity as the chimeric bispecific antibody (A69/B26/BBA) was obtained (FIG. 1). The antibody variable region sequences are shown in the following SEQ ID NOs.

(1) humanized A69 antibody VH (hA69a): SEQ ID NO: 1 (nucleotide sequence), SEQ ID NO: 2 (amino acid sequence)
(2) humanized B26 antibody VH (hB26-F123e4): SEQ ID NO: 3 (nucleotide sequence), SEQ ID NO: 4 (amino acid sequence)
(3) humanized BBA antibody VL (HAL-F123j4): SEQ ID NO: 5 (nucleotide sequence), SEQ ID NO: 6 (amino acid sequence)

Example 2

Selection of Sites in the Variable Region Amino Acid Modification Positions for Separation of Bispecific Antibodies In preparation of a bispecific antibody, when two types of H chains and one type of L chain are used for expression, the following three types of antibodies are expressed: a homodimer of the humanized A69H chain and humanized BBA L chain, a homodimer of the humanized B26H chain and humanized BBA L chain, and a heterodimer of the humanized A69H chain, humanized B26H chain, and humanized BBA L chain. The objective is to purify only the bispecific antibody by separating these three types of antibodies, and thus amino acid modifications were carried out to decrease the isoelectric point of the humanized A69H chain variable region and increase the isoelectric point of the humanized B26H chain variable region.

First, antibody Fv region models were prepared for the humanized A69 antibody and humanized B26 antibody by homology modeling using the MOE software (Chemical Computing Group Inc.), and the amino acid resides exposed on the surface of the variable regions of the humanized A69 antibody and humanized B26 antibody were confirmed. The models are shown in FIG. 2. According to a detailed analysis of these models, of the surface-exposed amino acids in the FR sequence outside CDR, H10, H12, H23, H39, H43, and H105 (based on Kabat numbering; Kabat E A et al. 1991. Sequences of Proteins of Immunological Interest. NIH) are thought to be candidates that can alter the isoelectric point without decreasing the activity.

Example 3

Amino Acid Modifications in the Variable Regions of Humanized Bispecific Antibodies Amino acid modifications were carried out at the sites selected in Example 2 to prepare modified antibodies. Specifically, the QuikChange Site-Directed Mutagenesis Kit (Stratagene) was used to introduce mutations into the produced humanized A69 antibody H-chain variable region (hA69a, nucleotide SEQ ID NO: 1) and humanized B26 antibody H-chain variable region (hB26-F123e4, nucleotide SEQ ID NO: 3) according the method described in the attached instruction manual. The H-chain variable region fragment-inserted plasmid was confirmed to have the desired humanized antibody variable region gene sequence, and digested with XhoI and SfiI. Then, the reaction solution was subjected to 1% agarose gel electrophoresis. DNA fragments having the desired size (about 400 bp) were purified using the QIAquick Gel Extraction Kit (QIAGEN) according to the method described in the attached instruction manual, and eluted with 30 μL of sterilized water. According to the method described in Example 1-2, H-chain expression vectors were prepared by inserting the prepared DNA fragments into an expression plasmid carrying a wild-type constant region and an expression plasmid in which the constant region amino acids have been replaced using the knobs-into-holes technique. Thereafter, humanized bispecific antibodies were prepared by the method described in Examples 1-3, 1-4, and 1-5. Sequences of the modified humanized antibody variable regions are shown in the SEQ ID NOs in Table 1 shown below.

TABLE 1

| Name | Modified position(s) | Amino acid SEQ ID NO: |
|---|---|---|
| Humanized A69 H chain variable region | | |
| hA69a | — | 2 |
| hA69-p18 | Q43E, Q105E | 7 |
| hA69-p8 | K12V, Q43E, Q105E | 8 |
| hA69-p17 | K23T, Q43E, Q105E | 9 |
| hA69-p16 | K12V, K23T, Q43E, Q105E | 10 |
| HA69-PFL | Q1E, K12V, K23T, G27Y, Q43E, N97L, Q105E | 11 |
| hA69-KQ | Q1E, K12Q, G16A, G27Y, S30T, Q43E, N97Q, Q105E | 12 |
| hA69-N97R | N97R | 13 |
| Humanized B26 H chain variable region | | |
| hB26-F123e4 | — | 4 |
| hB26-p19 | Q43K, Q105R | 14 |
| hB26-p15 | Q39K, Q43K, Q105R | 15 |
| hB26-PF | Q1E, P9A, D10Q, M28T, A37V, Q43K, Q105R | 16 |

Example 4

Analysis of Modified Humanized Antibodies by Isoelectric Focusing

To evaluate the alteration of surface charge due to amino acid modifications in the variable region, modified antibodies were prepared and analyzed by isoelectric focusing.

The humanized BBA L-chain (hAL-F123j4) expression vector was simultaneously expressed together with the H-chain expression vector of unmodified hA69a, or hA69-p18, hA69-p8, hA69-p17, or hA69-p16 modified from the humanized A69H chain. Five types of antibodies composed of hA69a, hA69-p18, hA69-p8, hA69-p17, or hA69-p16 homodimers were prepared. Similarly, the humanized BBA L-chain expression vector was simultaneously expressed together with the H-chain expression vector of unmodified hB26-F123e4, or hB26-p19 or hB26-p15 modified from the humanized B26H chain. Three types of antibodies composed of hB26-F123e4, hB26-p19, or hB26-p15 homodimers were prepared. Isoelectric focusing was performed as follows. PhastGel Dry IEF gel (Amersham Biosciences) was swollen for about 30 minutes in the swelling solution described below using the Phastsystem Cassette (Amersham Biosciences).

| 20% Glycerol | 0.95 mL |
|---|---|
| MilliQ water | 0.95 mL |
| Bio-Lyte 7/9 (Bio-Rad) | 10 μL |
| Bio-Lyte 3/10 (Bio-Rad) | 10 μL |
| Pharmalyte 8-10.5 for IEF (Amersham Biosciences) | 80 μL |

Electrophoresis was performed using the swollen gel by PhastSystem (Amersham Biosciences) according to the following program. The samples were applied to the gel in Step 2. A pI calibration kit (Amersham Biosciences) was used as the pI marker.

| Step 1: | 2000 V | 2.5 mA | 3.5 W | 15° C. | 75 Vh |
|---|---|---|---|---|---|
| Step 2: | 200 V | 2.5 mA | 3.5 W | 15° C. | 15 Vh |
| Step 3: | 2000 V | 2.5 mA | 3.5 W | 15° C. | 410 Vh |

After electrophoresis, the gel was fixed with 20% TCA, and then silver stained using a silver staining kit, protein (Amersham Biosciences) according to the protocol attached to the kit. After staining, the isoelectric points of the samples were calculated from the known isoelectric points of the pI marker.

Figure 3:
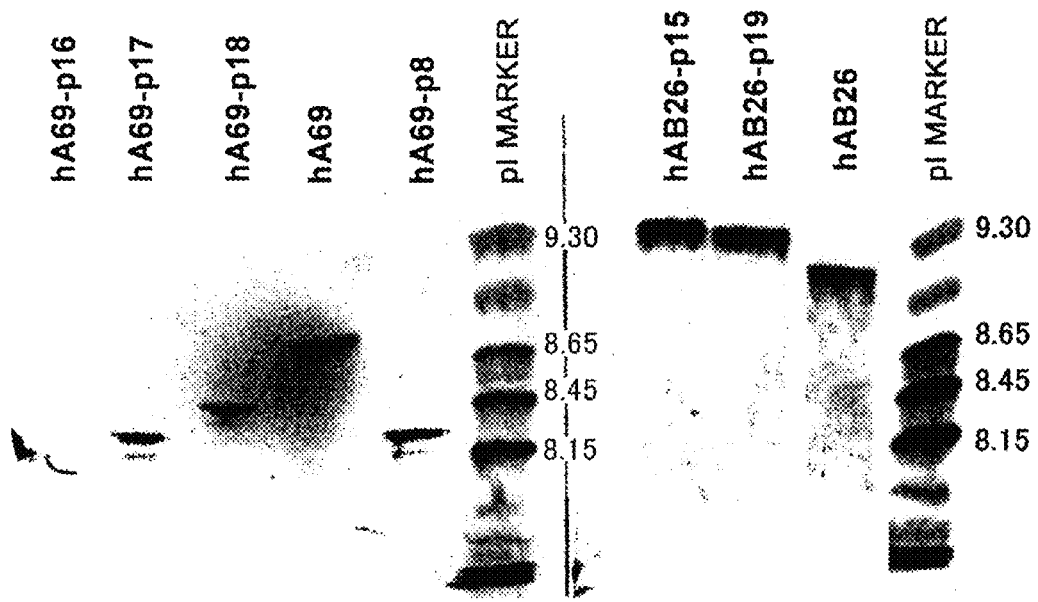
FIG. 3 is a photograph depicting the result of isoelectric focusing analysis of the unmodified humanized A69 antibody homodimer, humanized A69 antibody homodimers having a modified variable region, the unmodified humanized B26 antibody homodimer, and humanized B26 antibody homodimers having a modified variable region. The result confirms that the isoelectric points are altered by the modifications.

The results of analysis of the unmodified and modified humanized A69 antibody homodimers and the humanized B26 antibody homodimer are shown in FIG. 3. Band shifts were observed in the isoelectric focusing due to modification of the surface charge. The isoelectric points of the respective antibodies estimated in reference to the pI marker were approximately 8.4 for modified hA69-p18, approximately 8.2 for modified hA69-p17, approximately 8.2 for modified hA69-p8, and approximately 8.1 for modified hA69-p16, in contrast to approximately 8.8 for the unmodified hA69a homodimer. That is, the modification was able to provide a maximum isoelectric point difference of approximately 0.7. Similarly, regarding the humanized B26 homodimers, the isoelectric points were approximately 9.3 for modified hB26-p19 and approximately 9.4 for modified hB26-p15, in contrast to approximately 9.1 for unmodified hB26-F123e4. That is, the modification was able to provide a maximum isoelectric point difference of approximately 0.3. It was shown that the isoelectric point can be altered by modifying the charges on the surface amino acids in the variable region selected for this examination: H12, H23, H39, H43, and H105.

Example 5

Cation Exchange Chromatographic Analysis of Modified Humanized Antibodies

Cation exchange chromatographic analysis was performed by the following method using the modified antibodies produced in Example 4 to evaluate the effect of the modification on the separation of the two antibodies. The conditions for the cation exchange chromatographic analysis were as follows. The retention time was calculated for the humanized A69 antibody homodimer and the humanized B26 antibody homodimer.

Column: ProPac WCX-10, 4×250 mm, (Dionex)
Mobile phase: A: 10 mmol/L $NaH_2PO_4/Na_2HPO_4$, pH 6.25
B: 10 mmol/L $NaH_2PO_4/Na_2HPO_4$, 500 mmol/L NaCl, pH 6.25
Flow rate: 1.0 mL/min
Gradient: 10% B (5 min)→(40 min)→60% B→(5 min)→100% B (5 min)

Detection: 220 nm

Figure 4:
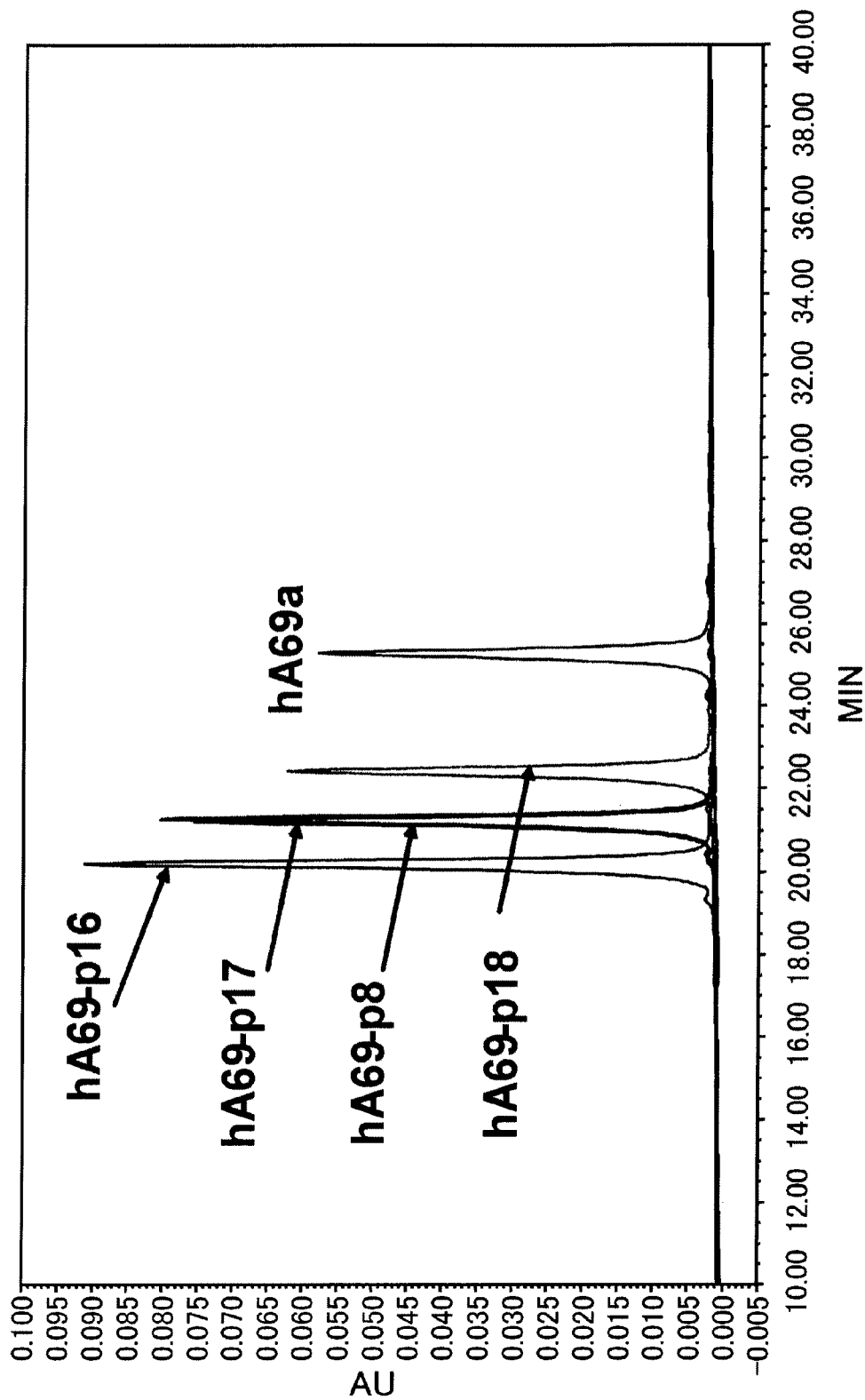
FIG. 4 depicts the result of cation exchange chromatographic analysis of humanized A69 antibody homodimers having a modified variable region. The result confirms that the peaks of the modified antibodies have been shifted compared to that of the unmodified antibody.
Figure 5:
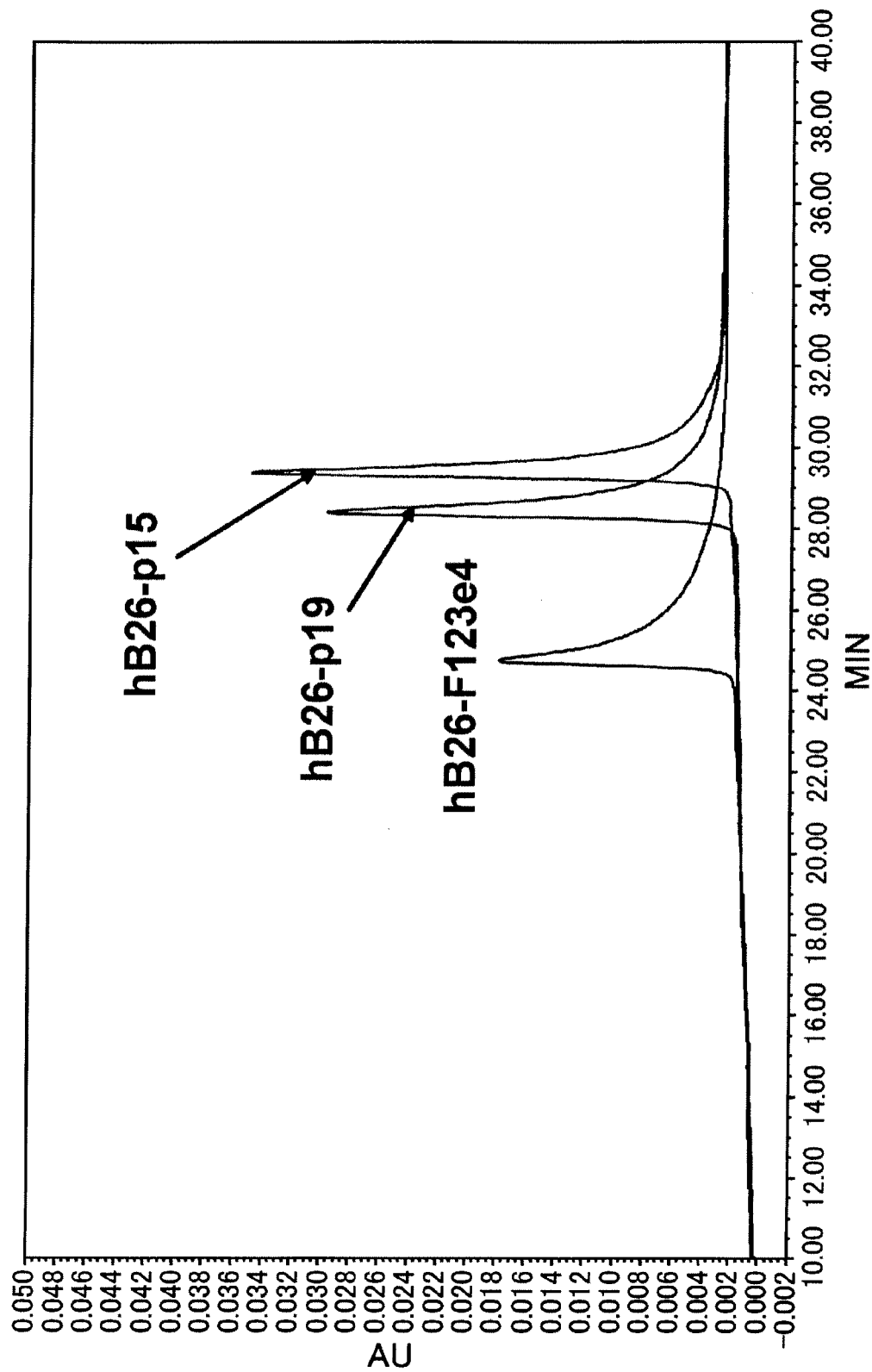
FIG. 5 depicts the result of cation exchange chromatographic analysis of humanized B26 antibody homodimers having a modified variable region. The result confirms that the peaks of the modified antibodies have been shifted compared to that of the unmodified antibody.

The results of analysis of the five types of unmodified and modified humanized A69 antibody homodimers, and the three types of unmodified and modified humanized B26 antibody homodimers are shown in FIG. 4 and FIG. 5, respectively. The retention time for both the unmodified humanized A69 antibody homodimer and the humanized B26 antibody homodimer was around 25 minutes, and thus separation of these homodimers was impossible, much less isolation of the desired bispecific antibody. Peak shifts were observed when comparing the unmodified humanized A69 antibody with those that have been modified to have lower isoelectric points, and the retention time was decreased to approximately 22.4 minutes, approximately 21.2 minutes, and approximately 20.2 minutes, as the number of modifications increased. Peak shifts were observed when comparing the unmodified humanized B26 antibody with those that have been modified to have higher isoelectric points for the variable region, and the retention time was increased to approximately 28.4 minutes and approximately 29.4 minutes, as the number of modifications increased. Thus, it was shown that the retention time can be altered by modifying the charges on the surface amino acids in the variable region selected for this examination, H12, H23, H39, H43, and H105, and thereby modifying the surface charges of the two types of antibodies.

Figure 9:
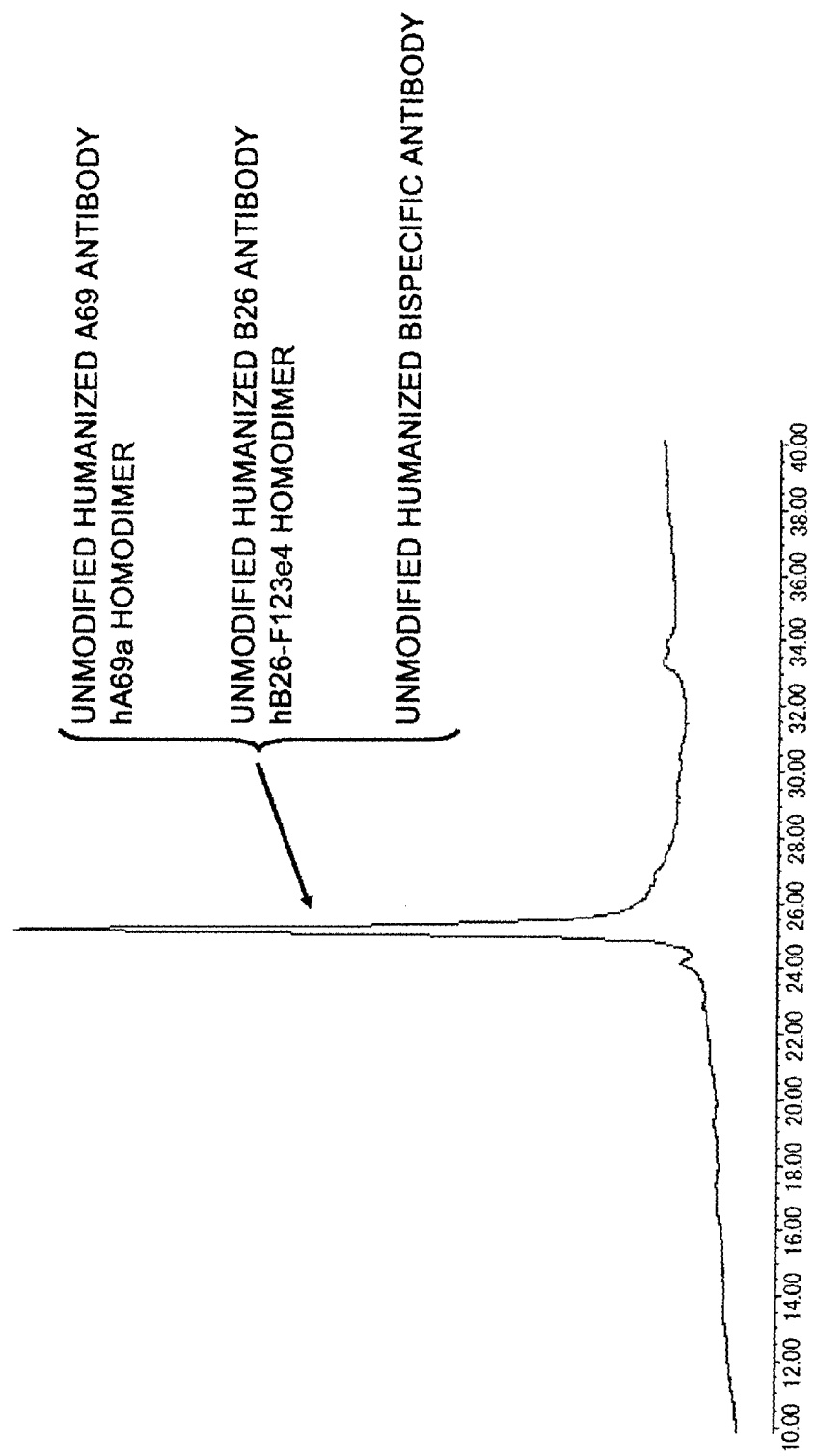
FIG. 9 depicts the result of cation exchange chromatographic analysis of an unmodified humanized bispecific antibody prepared using unmodified humanized A69-H chain hA69a, unmodified humanized B26-H chain hB26-F123e4, and humanized BBA-L chain hAL-F123j4. As a result, the two types of homodimers and the bispecific antibody were eluted as a single peak without separation.

According to the isoelectric point measurements in Example 4, despite a pI difference of 0.3 between the unmodified hA69a homodimer and the unmodified hB26-F123e4 homodimer, the retention time for both of the homodimers was around 25 minutes, and thus they could not be separated (FIG. 9). However, the pI difference between the unmodified hA69a homodimer and hB26-p19 was 0.5, and thus they were separated by a retention time difference of approximately 2.6 minutes. Also, the pI difference between hA69-p18 and the hB26 homodimer was 0.7, and thus they were separated by a retention time difference of approximately 3.4 minutes. Moreover, a maximum pI difference of 1.3 was generated between hA69-p16 and hB26-p15, and thus they were separated by a retention time difference of approximately 9.2 min. As described, the modifications made it possible to separate the two homodimers for the first time.

Example 6

Coagulation Activity Assessment of Modified Humanized Bispecific Antibodies

Based on the observation of surface charge alteration made through the analyses in Examples 4 and 5, two types of modified humanized antibody H chains (hA69-p8 and hB26-p15) and a humanized L chain (hAL-F123j4) were expressed to prepare humanized bispecific antibodies. An expression vector, into which The IgG4 constant region based on the knobs-into-holes technique was inserted into an expression vector, and it was used as the H-chain expression vector to efficiently promote heterodimerization. Coagulation activities were assessed according to the method described below using prepared humanized bispecific antibodies.

To determine whether a bispecific antibody is capable of correcting the coagulation ability of hemophilia A blood, effects of the antibody on the activated partial thromboplastin time (APTT) were determined using Factor VIII-deficient plasma. 50 µL of an antibody solution at a variety of concentrations, 50 µL of Factor VIII-deficient plasma (Biomerieux), and 50 µL of the APTT reagent (Dade Behring) were mixed and heated at 37° C. for three minutes. Coagulation reaction was initiated by adding 50 µL of 20 mM $CaCl_2$ (Dade Behring) to the mixture. The time period until coagulation was measured with KC10A (Amelung) linked to CR-A (Amelung).

Using a calibration curve produced by defining the coagulation time of Factor VIII-deficient plasma as 0% and the coagulation time of normal plasma as 100%, the Factor VIII-like activity (%) of a bispecific antibody was calculated from the coagulation time measured when the bispecific antibody was added.

Figure 6:
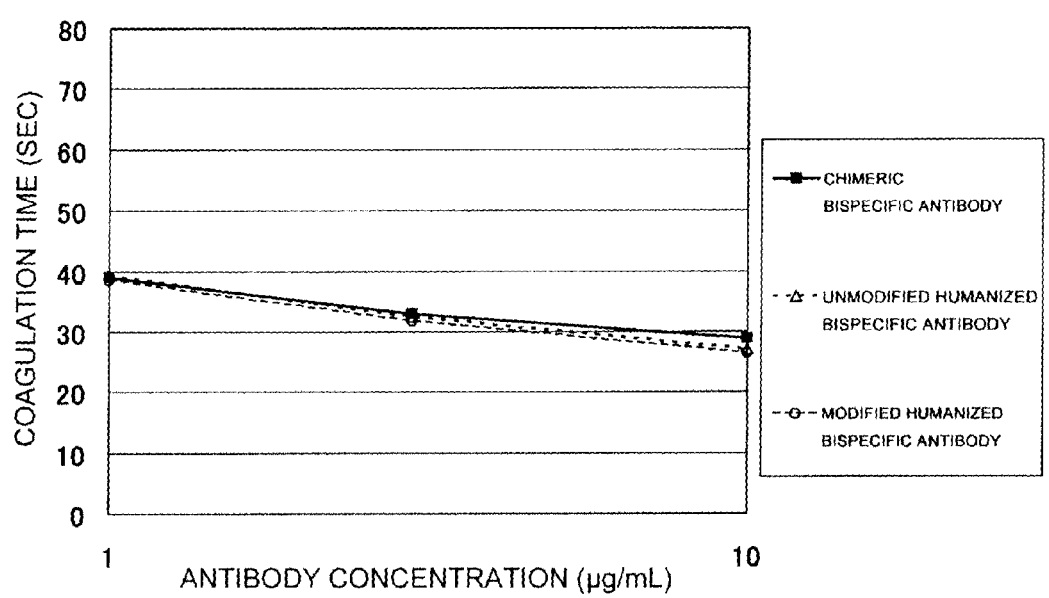
FIG. 6 depicts the result of evaluating the coagulation activity of humanized bispecific antibodies having a modified variable region (knobs-into-holes technique has been applied to the H chain constant regions). The result shows that the modified antibodies have a coagulation activity equivalent to that of the unmodified antibody.

The results of the activity assessment are shown in FIG. 6. Since the humanized bispecific antibody with a modified variable region showed a coagulation activity equivalent to that of the unmodified humanized bispecific antibody, it was shown that modification of the variable region in this Example does not affect antibody activities.

Example 7

Preparation and Assessment of CDR-Modified Humanized Antibodies

Figure 7:
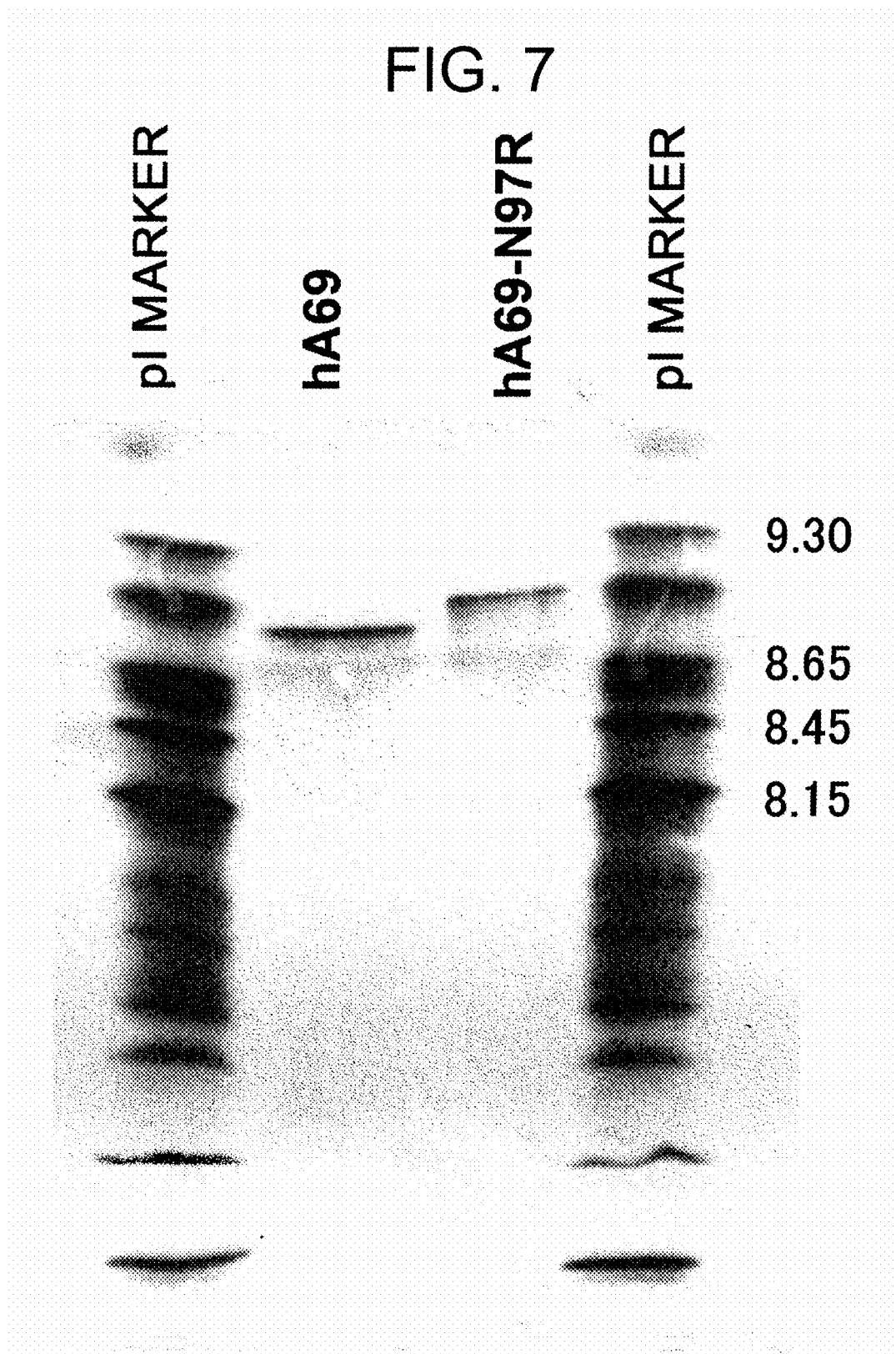
FIG. 7 is a photograph depicting the result of isoelectric focusing analysis of a humanized A69 antibody homodimer having a modified variable region (CDR). The results confirm that the band of the modified antibody has been shifted compared to that of the unmodified antibody.

As a result of the analysis of the humanized A69 antibody model produced in Example 2, H97 was confirmed to be a surface-exposed amino acid. Of the antibodies shown in Table 1, the humanized A69H chain hA69-N97R has a sequence in which asparagine at position 97 in CDR3 has been replaced with arginine. Modified antibodies were prepared by producing an expression vector carrying hA69-N97R according to the method of Example 1-2, and expressing it together with the humanized BBA L chain hAL-F123j4. To evaluate the alteration of surface charge of this antibody, isoelectric focusing was performed according to the method of Example 4. As indicated in FIG. 7, while the isoelectric point of the unmodified antibody (hA69a/hAL-F123j4) was 8.9, that of the modified antibody (hA69-N97R/hAL-F123j4) was 9.1, and thus alteration of the surface charge was also observed in the amino acid substitution of CDR.

Figure 8:
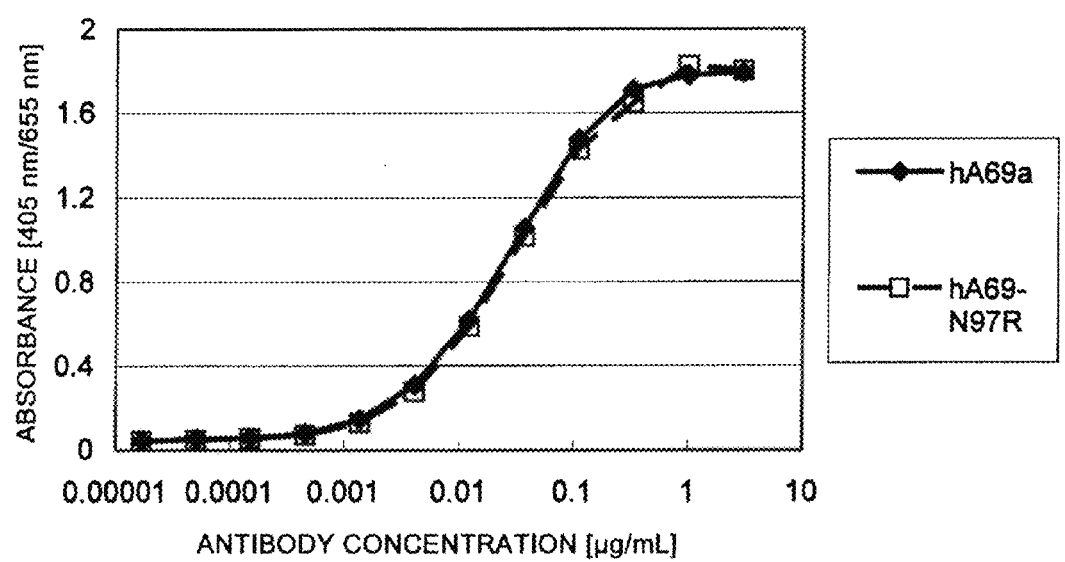
FIG. 8 depicts the result of evaluating the binding activity of the humanized A69 antibody homodimer having a modified variable region (CDR) towards the antigen Factor IXa. The result shows that the modified antibody has a binding activity equivalent to that of the unmodified antibody.

To evaluate the function of the modified antibodies, the activity of binding to the antigen, Factor IXa, was assayed by the following method. Factor IXaβ (Enzyme Research Laboratories) diluted to 1 µg/mL with coating buffer (100 mM sodium bicarbonate, pH 9.6, 0.02% sodium azide) was dispensed at 100 µL/well into a Nunc-Immuno plate (Nunc-Immuno™ 96 MicroWell™ plates MaxiSorp™ (Nalge Nunc International)), and then incubated overnight at 4° C. After three washes with PBS(−) containing Tween® 20, the plate was blocked with diluent buffer (50 mM Tris-HCl, pH 8.1, 1% bovine serum albumin, 1 mM $MgCl_2$, 0.15 M NaCl, 0.05% Tween® 20, 0.02% sodium azide) at room temperature for two hours. After removal of the buffer, a purified antibody diluted in the diluent buffer was added to the plate at 100 µL/well and incubated at room temperature for one hour. The plate was washed three times, then alkaline phosphatase-labeled goat anti-mouse IgG (BIOSOURCE) diluted at 1/4000 with the diluent buffer was added at 100 µL/well. This was then incubated at room temperature for one hour. The plate was washed five times, then a chromogenic substrate (Sigma) was added at 100 µL/well. This was then incubated at room temperature for 30 minutes. The absorbance at 405 nm (control: 655 nm) was measured using the Model 3550 Microplate Reader (Bio-Rad Laboratories). As a result, as shown in FIG. 8, the antibody in which the CDR had been modified to alter the surface charge showed a binding activity equivalent to that of the antibody before modification. Thus, it was shown that when the surface charge is modified, the sites of modification may not only be in the FR indicated in Example 5, but also in the CDR.

Example 8

Preparation and Assessment of Humanized Bispecific PF Antibodies

An unmodified humanized bispecific antibody was prepared using the unmodified antibodies (humanized A69H chain hA69a and humanized B26H chain hB26-F123e4) shown in Table 1, as well as the humanized BBA L chain hAL-F123j4 (SEQ ID NO: 5). A humanized bispecific PF antibody was prepared using the modified antibodies (the modified form of the humanized A69H chain hA69-PFL and the modified form of the humanized B26H chain hB26-PF) shown in Table 1, as well as the humanized BBA L chain hAL-s8 (SEQ ID NO: 17). According to the method described in Example 1-2, H-chain expression vectors were prepared using an expression vector carrying the wild-type constant region, and the antibodies were prepared by the method described in Examples 1-3, 1-4, and 1-5. Using a mixture solution containing the two types of homodimers and the bispecific antibody, cation exchange chromatographic analysis was carried out according to the method described in Example 5.

Figure 10:
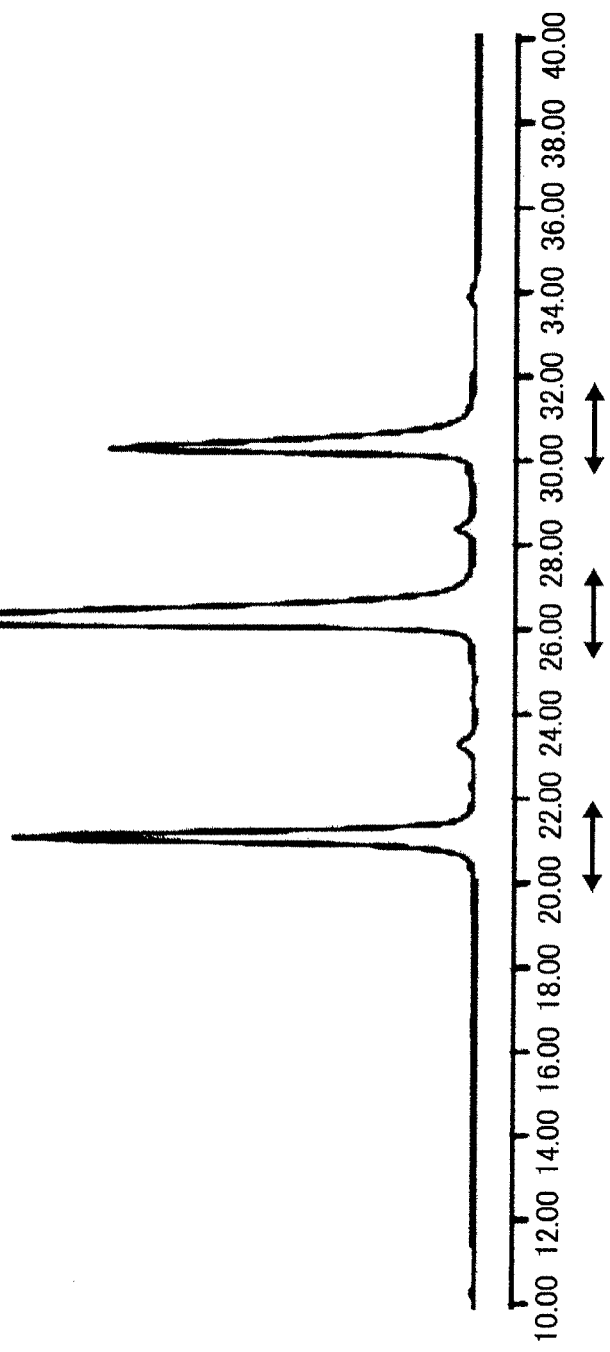
FIG. 10 depicts the result of cation exchange chromatographic analysis of a humanized bispecific PF antibody prepared using hA69-PF, a modified form of the humanized A69-H chain; hA26-PF, a modified form of the humanized B26-H chain; and hAL-s8, the humanized BBA-L chain. As a result, the two types of homodimers and the bispecific antibody were individually separated and eluted as three peaks in the following order: thA69-PF homodimer, humanized bispecific PF antibody, and hB26-PF homodimer.

The results of analysis of the unmodified humanized bispecific antibody and humanized bispecific PF antibody are shown in FIGS. 9 and 10. Regarding the unmodified humanized bispecific antibody, the results showed that the two types of homodimers and the bispecific antibody failed to separate, and were eluted as a single peak. In contrast, regarding the humanized bispecific PF antibody, each of the two types of homodimers and the desired bispecific antibody were separated, and were eluted as three peaks in the following order: hA69-PF homodimer, humanized bispecific PF antibody, and hB26-PF homodimer. By fractionating the three types of peaks in cation exchange chromatographic analysis, the two types of homodimers and the humanized bispecific PF antibody were purified. These fractions were concentrated using Amicon Ultra, MWCO 10000 (Millipore), then dialyzed overnight against 20 mM sodium acetate, 150 mM NaCl, pH 6.0 while cooling. Then, the concentrations were measured.

Figure 11:
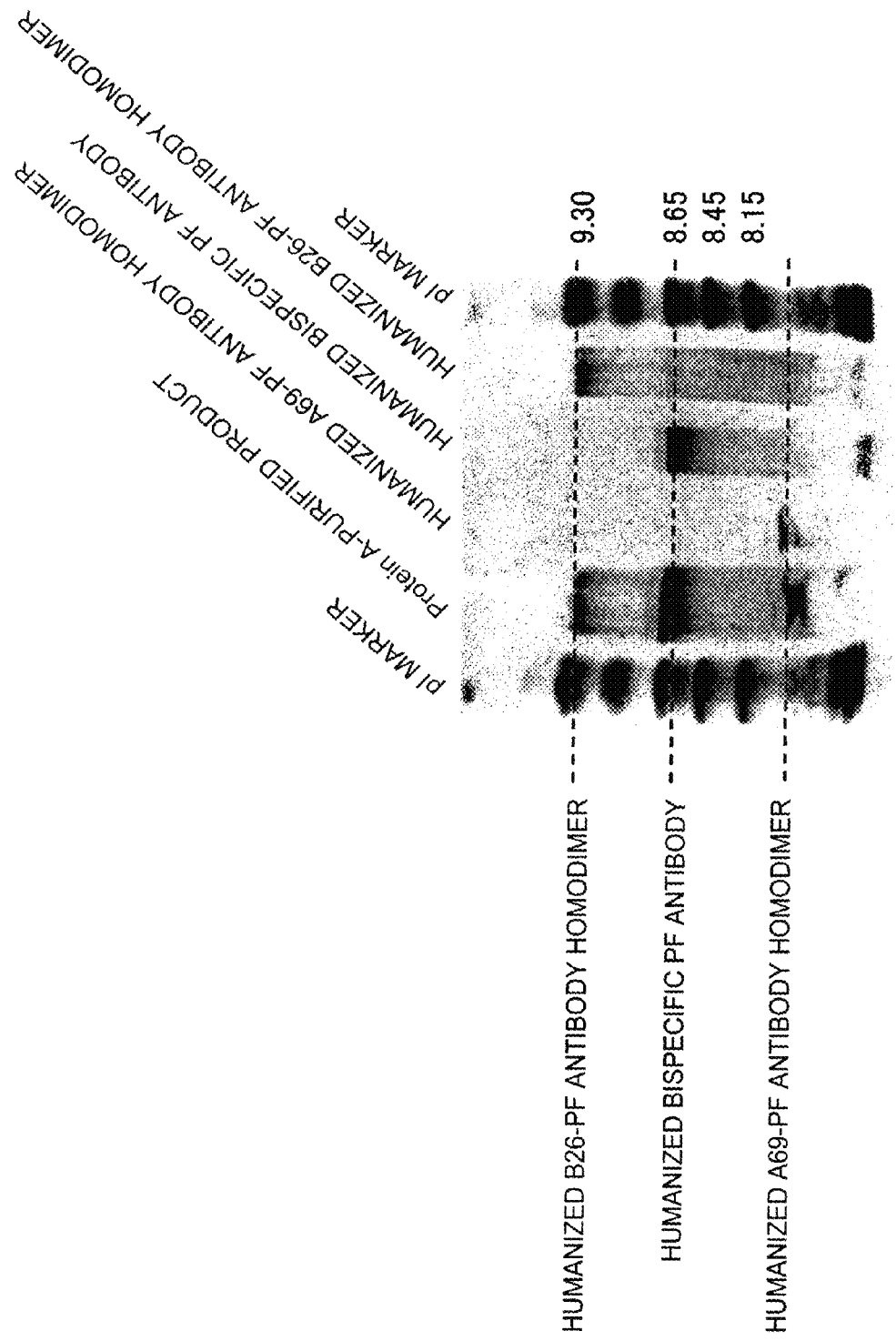
FIG. 11 is a photograph depicting the result of isoelectric focusing analysis of purified humanized A69 antibody-PF homodimers, humanized B26-PF antibody homodimers, and humanized bispecific PF antibodies. The result confirms that the bispecific antibody of interest has been purified.

After purifying each antibody, isoelectric focusing was performed according to the method described in Example 4. As shown in FIG. 11, the three bands of antibodies were present before the cation exchange chromatographic analysis, and thus it was confirmed that each of the antibodies can be purified by cation exchange chromatography. The following was also confirmed. The isoelectric points of the humanized A69-PF antibody homodimer, humanized bispecific PF antibody, humanized B26-PF antibody homodimer were approximately 7.9, approximately 8.6, and approximately 9.2, respectively. The isoelectric point difference between the humanized A69-PF antibody homodimer and the humanized bispecific PF antibody was approximately 0.7, while the isoelectric point difference between the humanized B26-PF antibody homodimer and the humanized bispecific PF antibody was approximately 0.6.

Figure 12:
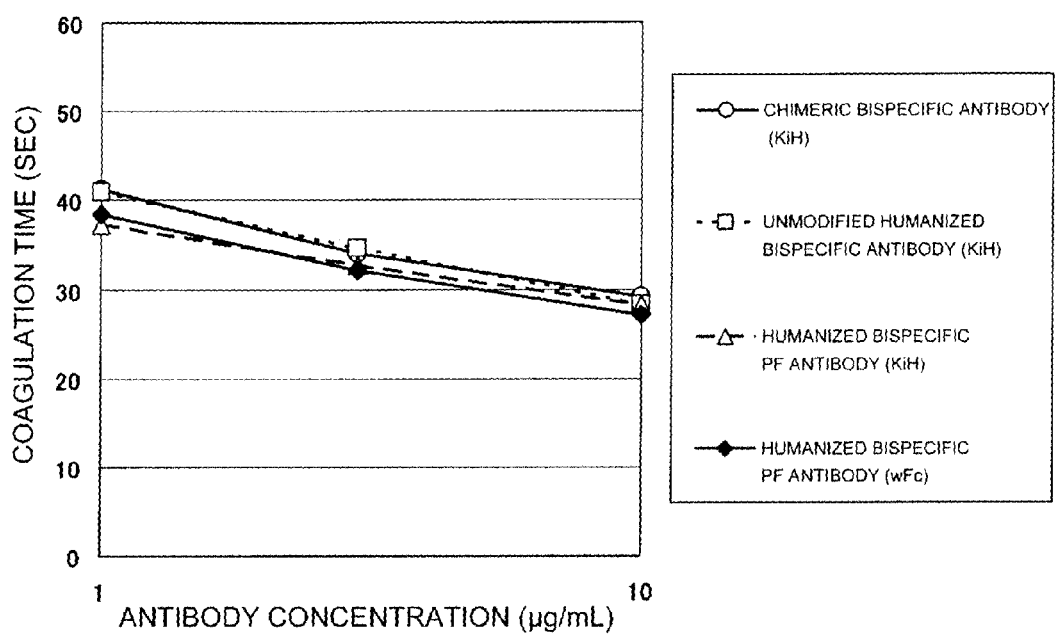
FIG. 12 depicts the result of evaluating the coagulation activity of purified humanized bispecific PF antibodies (the H chain constant region is wild-type). The result shows that the purified antibodies have a coagulation activity equivalent to that of the bispecific antibody KiH, the H chain constant region of which was produced by the knobs-into-holes technique.

Next, the coagulation activity of the bispecific PF antibody purified according to the method described in Example 6 was evaluated. The coagulation activity was compared with those of the following three types of antibodies expressed using an IgG4 constant region with the knobs-into-holes technique: the aforementioned chimeric bispecific antibody; the bispecific antibody composed of hA69a (SEQ ID NO: 2), hB26-F123e4 (SEQ ID NO: 4), and hAL-F123j4 (SEQ ID NO: 6) whose variable regions were not modified; and the bispecific antibody having the same variable regions as those of the purified bispecific PF antibody. The results of the evaluation are shown in FIG. 12. The coagulation activity of the bispecific PF antibody carrying an IgG4 constant region prepared based on the knobs-into-holes technique was equivalent to that of the bispecific PF antibody carrying a wild-type constant region purified by cation exchange chromatography. Thus, it was shown that in the present example, modifications at H10, H12, H23, H39, H43, and H105 in the variable region enable purification of bispecific antibodies to a high purity without affecting their activities.

Example 8

Establishment of Cell Lines Expressing Humanized Bispecific Antibodies

To prepare modified humanized bispecific antibodies, antibody-expressing cell lines were established as follows.

The H-chain constant region was amplified by PCR using the wild-type H-chain constant region gene of human IgG4 as a template, as well as a 5'-end primer designed such that the nucleotide sequence encoding the two amino acids (Ala-Ser) at the N terminus of the H-chain constant region will be the NheI recognition sequence (GCTAGC), and a primer designed to anneal to the 3'-end and carry the NotI recognizing site, and was linked to a vector prepared by digesting the pBluescriptKS+ vector (TOYOBO) with NheI and NotI (both from Takara), to produce pBCH4 comprising the IgG4 constant region gene. PCR was performed using a primer that is complementary to the 5'-end nucleotide sequence of the H-chain variable region of the humanized A69H chain antibody (hA69-KQ) and humanized B26H chain antibody (hB26-PF) shown in Table 1, and which has a Kozak sequence (CCACC) and the EcoRI recognition sequence, and a primer that is complementary to the 3'-end nucleotide sequence and has the NheI recognition sequence. The obtained PCR products were digested with EcoRI and NheI (both from Takara), and were inserted into pBCH4 similarly digested with EcoRI and NheI, to link the variable region and the constant region. The prepared humanized A69H chain antibody vector was digested with EcoRI and NheI (both from Takara), and was cloned into the pCXND3 expression vector for animal cells similarly digested with EcoRI and NotI.

The course of construction of the present vector pCXND3 will be described below. To separate the antibody H chain gene and the vector in DHFR-ΔE-rVH-PM1-f (see WO92/19759), it was digested at the EcoRI and SmaI restriction sites to recover only the vector part. Subsequently, the EcoRI-NotI-BamHI adaptor (Takara) was cloned into this vector. The resulting vector was named pCHOI. The region of pCHOI for expressing the DHFR gene was cloned into the HindIII restriction site of pCXN (Niwa et al., Gene 1991; 108: 193-200). The resulting vector was named pCXND3. Furthermore, the prepared humanized B26H chain antibody vector was digested with EcoRI and NotI (both from Takara), and was cloned in the pCXZD1 expression vector for animal cells similarly digested with EcoRI and NotI. The pCXZD1 vector is an expression vector in which the neomycin resistance gene of the pCXND3 vector has been replaced with a Zeocin resistance gene. Furthermore, PCR was performed using a synthetic oligonucleotide that is complementary to the 5'-end nucleotide sequence of the L chain variable region of the humanized BBA L chain antibody (hAL-AQ, SEQ ID NO: 18) and which has a Kozak sequence, and a synthetic oligonucleotide that is complementary to the 3'-end nucleotide sequence and has the BsiWI site. The obtained PCR product was cloned in the pBCL vector, in which the human kappa chain constant region was inserted into the pBluescript KS+ vector. The human L chain variable region and constant region were linked together via the BsiWI site. The produced L chain gene fragment was cloned into the expression vector pUCAG. The pUCAG vector was prepared by digesting pCXN (Niwa et al., Gene 1991; 108: 193-200) with the restriction enzyme BamHI to obtain a 2.6-kbp fragment, and cloning the fragment into the BamHI restriction site of the pUC19 vector (TOYOBO). The vector produced by cloning the L chain into pUCAG was digested with the restriction enzyme BamHI, and this was cloned into the expression vector pHygDHFR-4b containing a hygromycin resistance gene. The three types of expression vectors thus produced were linearized with restriction enzymes, and then they were transfected into CHO-DG44 cells to establish antibody-expressing cell lines.

Preparation of stable expression cell lines was carried out as follows. Genes were introduced by the electroporation method using Gene Pulser II (Bio-Rad). Each antibody expression vector and 0.75 mL of CHO cells ($1\times10^7$ cells/ml) suspended in PBS were mixed together, and cooled on ice for ten minutes. Then, the mixture was transferred into a cuvette, and then a pulse was applied at 1.5 kV and a capacitance of 25 µFD. After a recovery time of ten minutes at room temperature, the cells subjected to the electroporation treatment were suspended in 40 mL of CHO-S-SFMII medium (Invitrogen) containing 1×HT supplement (Invitrogen). A ten-fold diluted solution was prepared using the same culture medium, and added at 100 µL/well to a 96-well culture plate. After culturing in a $CO_2$ incubator (5% $CO_2$) for one day and night, Geneticin (Invitrogen), Zeocin (Invitrogen), and Hygromycin B (Invitrogen) were added at 0.5 mg/mL, 0.6 mg/mL, and 0.4 mg/mL, respectively, and culture was continued for two weeks. Colonies of transfected cells showing drug resistance were sequentially cultured and expanded. Large scale culturing was carried out using the established high expression cell lines, and the culture supernatant was obtained.

Example 9

Separation and Purification of Humanized Bispecific Antibodies Using a Standard Preparative Column Bispecific antibodies were purified from the culture supernatant obtained in Example 8 by the following method. The culture supernatant was applied to a rProtein A Sepharose Fast Flow column (Amersham Biosciences, 50 mm I.D.×9.9 cm H.=194.3 mL with resin) equilibrated using an equilibration buffer (20 mmol/L sodium phosphate buffer, 1 mmol/L NaCl). After washing with washing buffer 1 (20 mmol/L sodium phosphate buffer, 1 mol/L NaCl, pH 7.0), and then with washing buffer 2 (50 mmol/L sodium acetate buffer, pH 6.0), elution was carried out using 100 mmol/L acetic acid. Immediately after elution, the eluate was diluted three-fold with 20 mmol/L sodium acetate buffer, pH 6.0.

The obtained purified solution was applied to a standard preparative column, SP TOYOPEARL 650M column (TOSO, 26 mm I.D.×22.3 cm H.=118.3 mL with resin) equilibrated with Solvent A (20 mmol/L sodium acetate buffer, pH 6.0). Separation was performed based on the difference in surface charge between antibodies, using the following solutions and gradient conditions.

Solvent A: 20 mmol/L sodium acetate buffer, pH 6.0
Solvent B: 20 mmol/L sodium acetate buffer, 1 mol/L NaCl, pH 6.0
Flow Rate: 10 mL/min (113 cm/h), or 5.3 mL/min (60 cm/h) only at the time of elution

| Gradient: | 0 → 15% B | Step wise | 3 Column Volume (CV) flushed |
|---|---|---|---|
| | 15 → 22% B | gradient | 2.5 CV |
| | 22 → 30% B | gradient | 6 CV |
| | 30 → 100% B | Step wise | 3 CV flushed |

Figure 13:
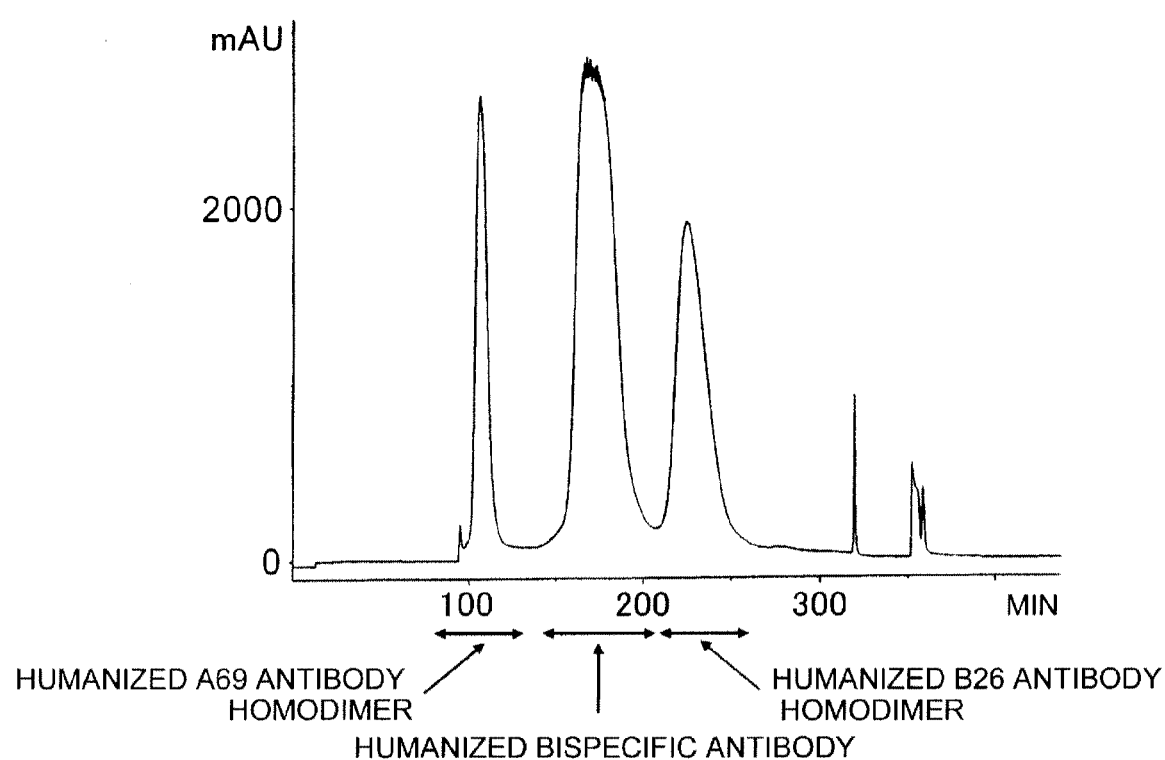
FIG. 13 depicts a chromatogram obtained when the bispecific antibody was purified from a culture supernatant containing three types of antibodies, the humanized A69 antibody homodimer, humanized B26 antibody homodimer, and humanized bispecific antibody, using a standard preparative column.

As a result of the elution, three peaks were detected as shown in FIG. 13. Thus, it was shown that bispecific antibodies can be also separated and purified using a standard preparative column.

Example 10

Activity Assessment of Modified Humanized Bispecific Antibodies

Figure 14:
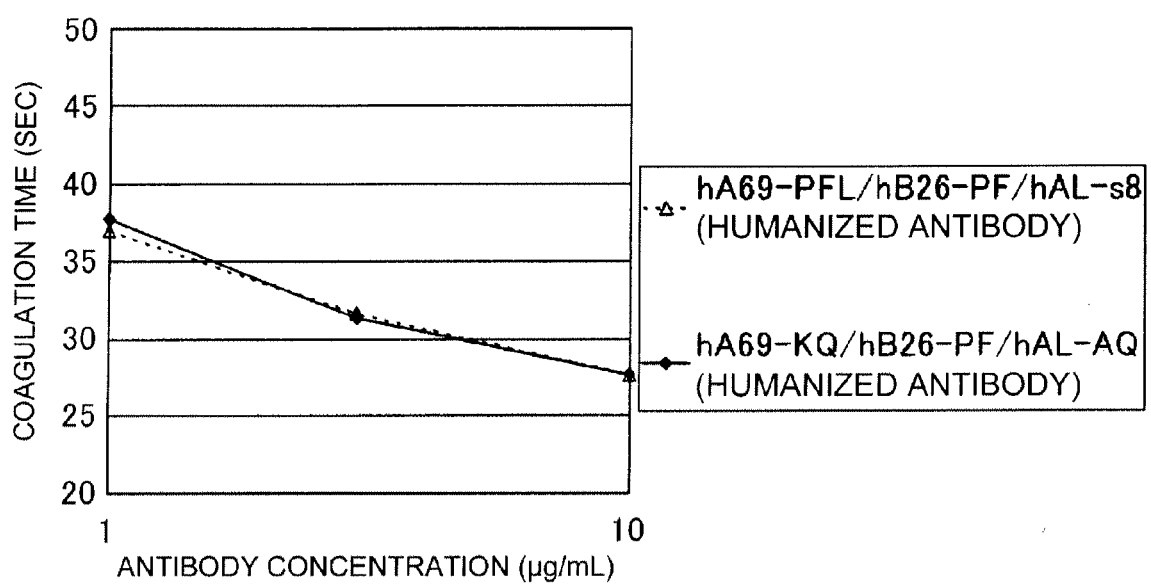
FIG. 14 depicts the result of evaluating the coagulation activity of a humanized bispecific antibody (the H chain constant region is wild-type) purified using a standard preparative column. The results show that the humanized bispecific antibody has a coagulation activity equivalent to that of the humanized bispecific PF antibody.

The coagulation activity of the humanized bispecific antibody prepared in Example 9 was evaluated according to the method described in Example 6. The results of the evaluation are shown in FIG. 14. The humanized bispecific antibody purified in Example 9 had a coagulation activity equivalent to that of the humanized bispecific PF antibody prepared in Example 8. Thus, it was shown that even if amino acid sequences of the variable regions are slightly different in hA69-PFL and hA69-KQ, or even if the antibodies are purified using a standard preparative column, the antibody activities were not affected.

In view of the above, it was shown that the humanized bispecific antibody of interest and the two types of homodimeric antibodies can be separated and purified without modifying the structure or function (activity) of the antibody, by altering the surface charge through modification of the H-chain variable region when preparing the bispecific antibody. Since it was shown that bispecific antibodies can be separated and purified on a standard preparative column using the present method, this will be useful as a method for producing pharmaceuticals comprising a bispecific antibody.

Example 11

Production of Subclass Hybrid Antibodies 11-1. Cloning of the Human IgG2 Antibody H-Chain Constant Region Gene The following procedures were carried out to clone the human IgG2 antibody H-chain constant region gene.

For amplification of the cDNA fragment, 50 µL of reaction solution (1 µL each of 20 µM K62 primer (5' cac cgt ctc ctc agc ctc cac caa 3', SEQ ID NO: 22) and K63 primer (5' gtg gca ctc att tac ccg gag aca 3', SEQ ID NO: 23), 5 µL of MTC Multiple Tissue cDNA Panels (peripheral leukocytes) (Clontech), 4 µL of 5× Prime STAR Buffer, 4 µL of 2.5 mM dNTPs, and 1 µL of PrimeSTAR HS DNA Polymerase (the above from Takara)) was prepared, and this was subjected to PCR. PCR was performed using a thermal cycler GeneAmp PCR system 9700 (Perkin Elmer), by heating at 98° C. for two minutes, followed by 30 cycles of reacting at 98° C. for ten seconds, 60° C. for five seconds, and 72° C. for two minutes per cycle, and finally heating at 72° C. for ten minutes. After PCR, the reaction solution was subjected to 1% agarose gel electrophoresis. Amplified fragments having the size of interest (approximately 1000 bp) were purified using the QIAquick Gel Extraction Kit (QIAGEN) according to the method described in the attached instruction manual, and eluted with 50 μL of sterile water. Then, r-Taq treatment was performed to add A (Adenosine) to the ends of the amplified fragments. For the r-Taq treatment, the obtained amplified fragments were incubated in 10 μL of rTaq reaction solution (1 μL of 10×rTaq reaction solution, 1 μL of 2.5 mM dNTPs, 1 μL of rTaq, and 7 μL of the above-mentioned amplified fragments) at 72° C. for 30 minutes. The r-Taq-treated fragments were cloned into the pCR2.1-TOPO vector (Invitrogen), and the nucleotide sequences were determined. The nucleotide sequence of each DNA fragment was determined by a DNA sequencer ABI PRISM 3730xL Genetic Analyzer (Applied Biosystems) using the BigDye Terminator 3.1 Cycle Sequencing Kit (Applied Biosystems) according to the method described in the attached instruction manual.

The determined nucleotide sequences were compared to the sequence of Accession No. BX640623. If nucleotides in a determined sequence encode an amino acid sequence different from the corresponding sequence of BX640623, such nucleotides were considered to be mutations inserted during PCR amplification. In such cases, amino acid substitutions were performed using the Quick Change Site-Directed Mutagenesis Kit (Stratagene) so that the amino acid sequence will be the same as that of BX640623. The Quick Change Site-Directed Mutagenesis Kit (Stratagene) was used according to the method described in the attached instruction manual. Furthermore, to link the human IgG2H chain constant region gene to a desired variable region gene, a mutation was introduced such that the first two amino acids (Ala-Ser) of the human IgG2H chain constant region were encoded by the restriction enzyme NheI recognition sequence (GCTAGC). The nucleotide sequence and amino acid sequence of the human IgG2H-chain constant region used in this examination are shown in SEQ ID NOs: 24 and 25, respectively.

11-2. Construction of Expression Vectors of Subclass-Substituted Antibodies

Antibody expression vectors, in which the H-chain variable region of the humanized PM-1 antibody is linked to one of the H chain constant regions of human IgG1, human IgG2, and human IgG4, were prepared as follows.

PCR was performed using a synthetic oligonucleotide that has a Kozak sequence and is complementary to the 5'-end nucleotide sequence of the H-chain variable region of the humanized anti-human interleukin 6 receptor antibody (humanized PM-1 antibody) described in a Non-Patent Document (Sato K. et al., Cancer Research 1993, 53:851-856), and a synthetic oligonucleotide that has the NheI recognition sequence and is complementary to the 3'-end nucleotide sequence. The obtained PCR product was cloned into the pB-CH vector, in which the human IgG1 H chain constant region (see Sato, K. et al., Cancer Research 1993, 53:851-856) was inserted into the pBluescript KS+ vector (TOYOBO). The H chain gene fragment, in which the H-chain variable region and constant region were linked, was inserted into the pCAGGS vector whose expression is regulated by the chicken β-actin promoter (Niwa et al. 1991 Gene, 108: 193-199). The PCR-amplified H-chain variable region gene of the humanized PM-1 antibody was linked to the human IgG4 constant region gene (see WO 99/51743) or the human IgG2H chain gene prepared in Example 11-1 via the 5'-end NheI site, and then inserted into the pCAGGS vector. Each H-chain expression vector expresses the H chain by linking the H-chain variable region of the humanized PM-1 antibody to the humanized H chain constant region via the NheI sequence.

Similarly, PCR was performed using a synthetic oligonucleotide that has a Kozak sequence and is complementary to the 5'-end nucleotide sequence of the L-chain variable region of the humanized PM-1 antibody, and a synthetic oligonucleotide that has the restriction enzyme BsiWI recognition sequence and is complementary to the 3'-end nucleotide sequence. The obtained PCR product was cloned into the pB-CL vector, in which the human kappa chain constant region was inserted into the pBluescript KS+ vector (TOYOBO). The L chain gene fragment, in which the L-chain variable region and constant region were linked, was inserted into the pCAGGS vector whose expression is regulated by the chicken β-actin promoter. The L chain is expressed by linking the L-chain variable region of the humanized PM-1 antibody to the human kappa chain constant region via the BsiWI sequence.

11-3. Expression of Subclass Hybrid Antibodies

Subclass hybrid antibodies can be produced by combining any two of the humanized PM-1 antibody H chain expression vectors carrying the constant region of human IgG1, human IgG2, or human IgG4, and coexpressing them with the humanized PM-1 antibody L-chain expression vector in cells for expression. Each antibody was expressed by the method described in Example 4-2 or the following method. Human fetal renal carcinoma cell-derived HEK293H strain (Invitrogen) was suspended in a DMEM medium (Invitrogen) containing 10% Fetal Bovine Serum (Invitrogen), and this was seeded at a cell density of $5-6 \times 10^5$ cells/mL (10 mL per dish) in dishes used for adhesive cells (10-cm diameter, CORNING) and cultured for one day and night in a $CO_2$ incubator (37° C., 5% $CO_2$). Then, the medium was removed by suction, and 6.9 mL of CHO-S-SFM-II (Invitrogen) medium was added. As described below, the mixture solutions for expressing the different subclass antibodies and the mixture solutions for expressing the hybrid antibodies (a total of 13.8 μg) were prepared using the plasmid DNAs prepared in 11-2.

(1) L-chain expression vector 6.9 μg, IgG1 H-chain expression vector 6.9 μg
(2) L-chain expression vector 6.9 μg, IgG2H-chain expression vector 6.9 μg
(3) L-chain expression vector 6.9 μg, IgG4H-chain expression vector 6.9 μg
(4) L-chain expression vector 6.9 μg, IgG1 H-chain expression vector 3.45 μg, IgG2H-chain expression vector 3.45 μg
(5) L-chain expression vector 6.9 μg, IgG2H-chain expression vector 3.45 μg, IgG4H-chain expression vector 3.45 μg
(6) L-chain expression vector 6.9 μg, IgG1 H-chain expression vector 3.45 μg, IgG4H-chain expression vector 3.45 μg Each mixture solution was mixed with 20.7 μL of 1 μg/mL Polyethylenimine (Polysciences Inc.) and 690 μL of CHO-S-SFMII medium, left to stand at room temperature for ten minutes, then added to the cells in each dish, and then the cells were then incubated in a $CO_2$ incubator (37° C., 5% $CO_2$) for four to five hours. Thereafter, 6.9 mL of CHO-S-SFM-II (Invitrogen) medium was added and then the cells were incubated in a $CO_2$ incubator for three days. The culture supernatant was collected, then cells were removed by centrifugation (at approximately 2000 g for five minutes at room temperature), and the solution was sterilized by passing it through a 0.22 µm filter MILLEX®-GV (Millipore). The sample was stored at 4° C. until use.

11-4. Purification of Subclass Hybrid Antibodies

100 µL of rProtein A Sepharose™ Fast Flow (Amersham Biosciences) was added to the culture supernatant obtained by the method described in Example 11-3, and the solution was mixed by rotation at 4° C. for four hours. The solution was transferred to an Ultrafree®-MC 0.22-µm filter cup (Millipore). After three washes with 500 µL of TBS, the rProtein A Sepharose™ resin was suspended in 100 µL of 50 mM aqueous sodium acetate solution at pH 3.0, and left to stand for two minutes, and then, the antibody was eluted. The eluate was immediately neutralized by adding 6.7 µL of 1.5 M Tris-HCl, 150 mM NaCl, pH 8.0. The buffer of the obtained antibody solution was exchanged by dialyzing it against PBS for activity measurement, or against 20 mM acetic acid buffer containing 150 mM NaCl, pH 6.0 for DSC measurement. Hereinbelow, the purified antibody carrying the H-chain constant region of human IgG1 will be referred to as "unmodified humanized anti-PM-1 antibody", the antibody carrying the H-chain constant region of human IgG2 will be referred to as "IgG2-substituted humanized anti-PM-1 antibody", and the antibody carrying the H-chain constant region of human IgG4 will be referred to as "IgG4-substituted humanized anti-PM-1 antibody".

11-5. Quantification of Subclass Hybrid Antibody Concentration

The absorbance of the antibody-containing solution obtained in 11-4 at 280 nm was measured on ND-1000 Spectrophotometer (NanoDrop) using 2 µL of the solution, or on the DU600 spectrophotometer (BECKMAN) using 50 µL of the solution. The antibody concentration was calculated from the obtained values using the following equation. PBS, or 20 mM acetic acid buffer containing 150 mM NaCl at pH6.0 was used as the blank.

$$\text{Antibody concentration (mg/mL)} = \text{absorbance} \times \text{dilution factor} / 14.6 \times 10$$

Example 12

Analyses of Subclass Hybrid Antibodies 12-1. Analysis of Subclass Hybrid Antibodies by Isoelectric Focusing Isoelectric focusing analysis was carried out to evaluate the alteration of surface charge as a result of substitution in the constant region.

Isoelectric focusing was performed as follows. PhastGel Dry IEF (Amersham Biosciences) gel was swollen for about 30 minutes in the swelling solution described below using the Phastsystem Cassette (Amersham Biosciences).

| | |
|---|---|
| 20% Glycerol | 1.5 mL |
| Pharmalyte 8-10.5 for IEF (Amersham Biosciences) | 100 mL |

Electrophoresis was performed using the swollen gel by PhastSystem (Amersham Biosciences) according to the following program. The samples were applied to the gel in Step 2. A pI calibration kit (Amersham Biosciences) was used as the pI marker.

| | | | | | |
|---|---|---|---|---|---|
| Step 1: | 2000 V | 2.5 mA | 3.5 W | 15° C. | 75 Vh |
| Step 2: | 200 V | 2.5 mA | 3.5 W | 15° C. | 15 Vh |
| Step 3: | 2000 V | 2.5 mA | 3.5 W | 15° C. | 410 Vh |

After electrophoresis, the gel was fixed with 20% TCA, and then silver stained using a silver staining kit, protein (Amersham Biosciences) according to the protocol attached to the kit. After staining, the isoelectric points of the samples were calculated from the known isoelectric points of the pI marker.

Figure 15:
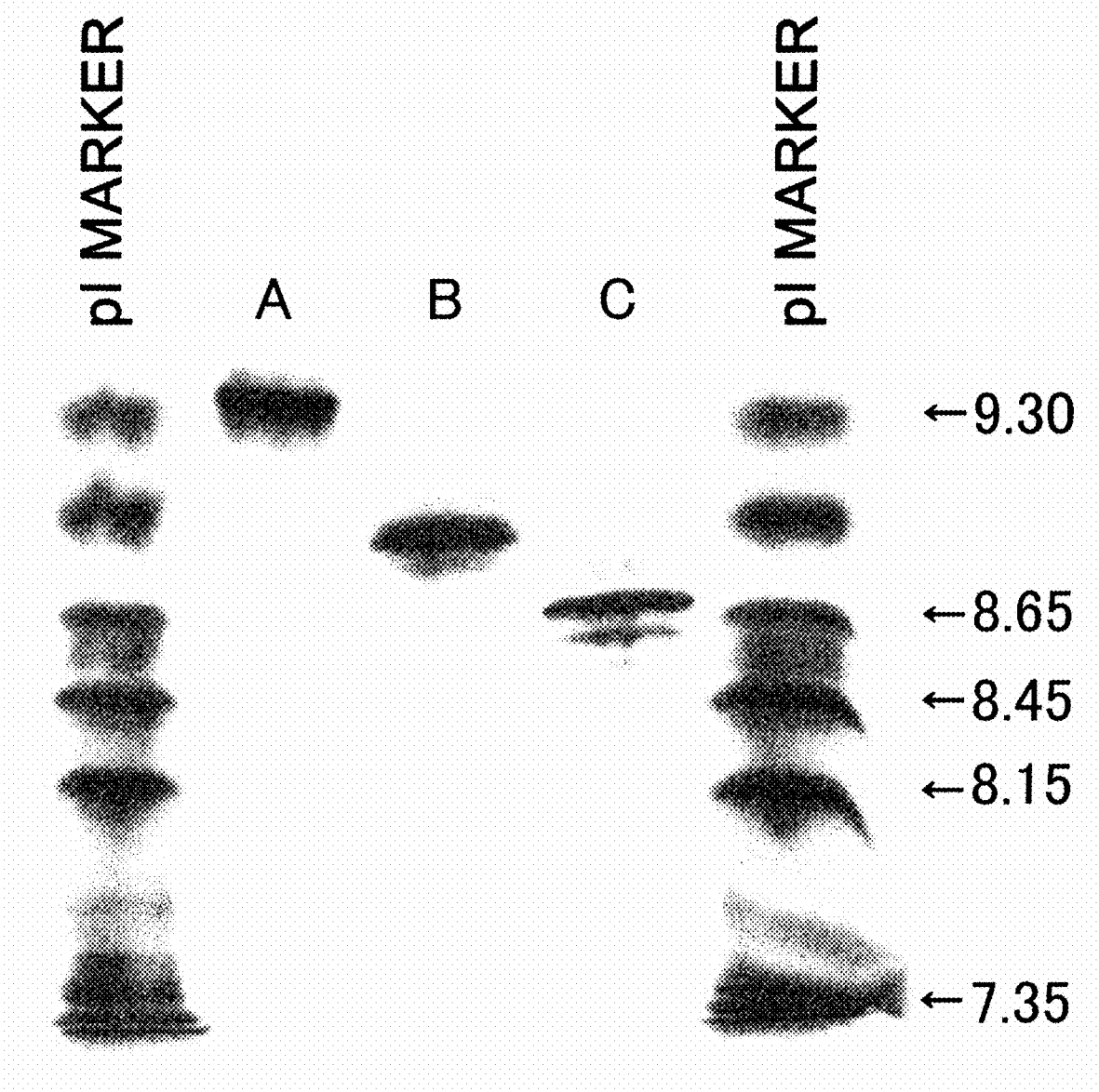
FIG. 15 is a photograph depicting the result of isoelectric focusing analysis of unmodified, IgG2-substituted, and IgG4-substituted humanized PM-1 antibodies. The result confirms that the modifications alter the isoelectric point of the antibody. A: unmodified humanized PM-1 antibody; B: IgG2-substituted humanized PM-1 antibody; C: IgG4-substituted humanized PM-1 antibody.

The results of analysis of the unmodified, IgG2-substituted and IgG4-substituted humanized PM-1 antibodies are shown in FIG. 15. Band shifts were observed in isoelectric focusing due to subclass substitution. The isoelectric points of the respective antibodies estimated in reference to the pI marker were approximately 8.9 for the IgG2-substituted humanized PM-1 antibody, and approximately 8.7 for the IgG4-substituted humanized PM-1 antibody, in contrast to approximately 9.3 for the unmodified humanized PM-1 antibody. That is, the substitution was able to provide a maximum isoelectric point difference of approximately 0.6. It was shown in this examination that the isoelectric points can be altered by substituting the constant region of an antibody subclass.

Figure 16:
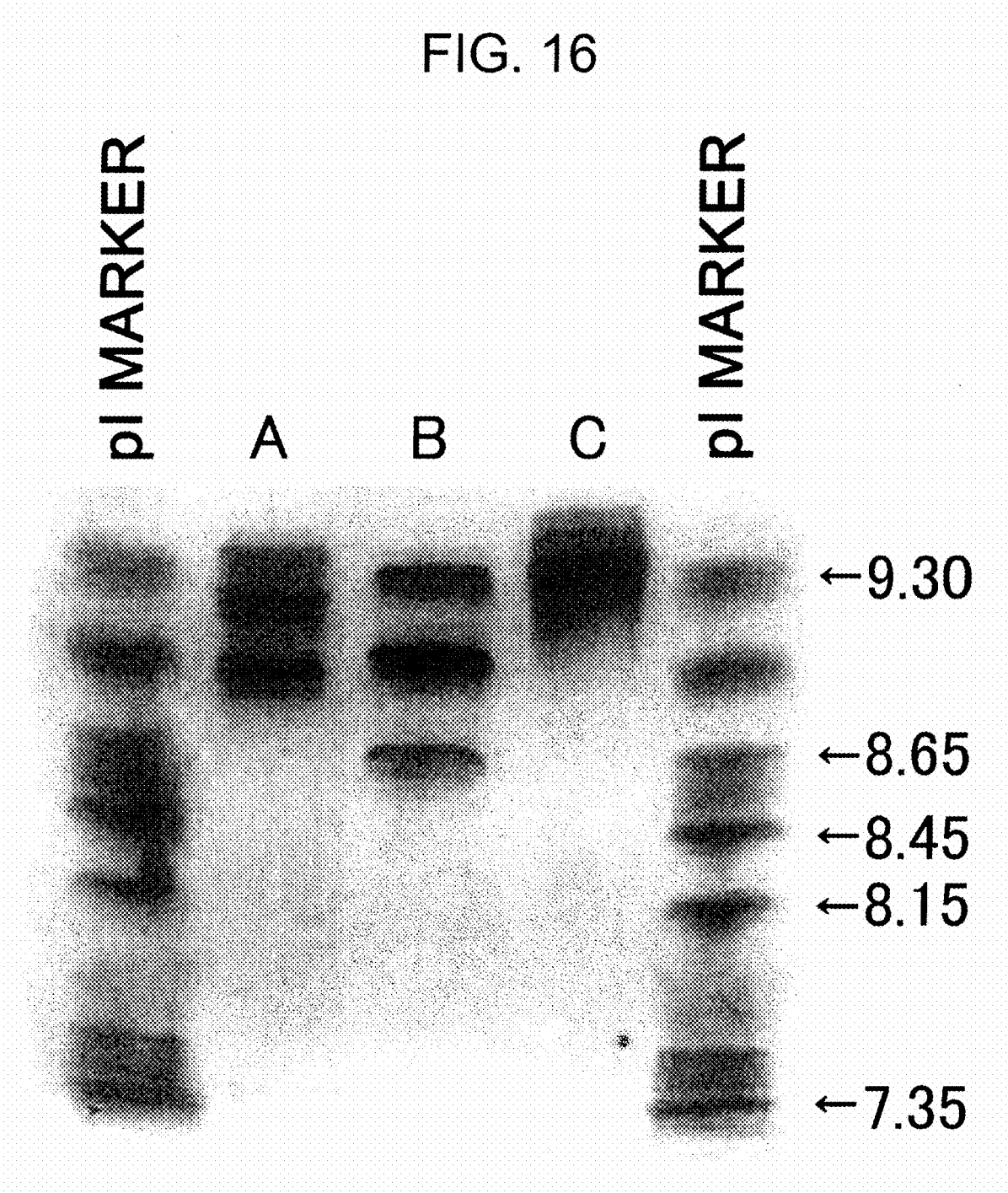
FIG. 16 is a photograph depicting the result of isoelectric focusing analysis of the unmodified humanized PM-1 antibody coexpressed with the IgG2-substituted or IgG4-substituted humanized PM-1 antibody. The result shows that the different subclass antibodies and subclass hybrid antibodies are separated according to their pI differences. A: coexpression of the unmodified humanized PM-1 antibody and the IgG2-substituted humanized PM-1 antibody; B: coexpression of the unmodified humanized PM-1 antibody and the IgG4-substituted humanized PM-1 antibody; C: humanized PM-1 antibody purified product (bulk).

Next, the results of analysis of coexpressed unmodified and IgG2-substituted humanized PM-1 antibodies, and coexpressed unmodified and IgG4-substituted humanized PM-1 antibodies are shown in FIG. 16. Herein, three major bands corresponding to the homodimers of the respective subclasses and the heterodimer were observed in each combination. The isoelectric points of the respective subclass hybrid antibodies estimated in reference to the pI marker were 9.2 for the unmodified humanized PM-1/IgG2-substituted human PM-1 hybrid antibody and 9.0 for the unmodified humanized PM-1/IgG4-substituted human PM-1 hybrid antibody. It was shown in this study that subclass hybrid antibodies can be produced by coexpressing a combination of expression vectors of subclass antibodies, and that the hybrid antibodies can be separated by their difference in isoelectric points.

12-2. Cation Exchange Chromatographic Analysis of Subclass Hybrid Antibodies

Cation exchange chromatographic analysis was performed by the following method using the subclass hybrid antibodies prepared in Example 11, and the effect of the subclass substitution on separation was evaluated. The conditions for cation exchange chromatographic analysis were as follows. The retention time was calculated for the unmodified humanized PM-1 antibody, the IgG2-substituted humanized PM-1 antibody, the IgG4-substituted humanized PM-1 antibody, the hybrid antibody of the unmodified humanized PM-1 antibody and IgG2-substituted humanized PM-1 antibody, and the hybrid antibody of the unmodified humanized PM-1 antibody and IgG4-substituted humanized PM-1 antibody.

Figure 17:
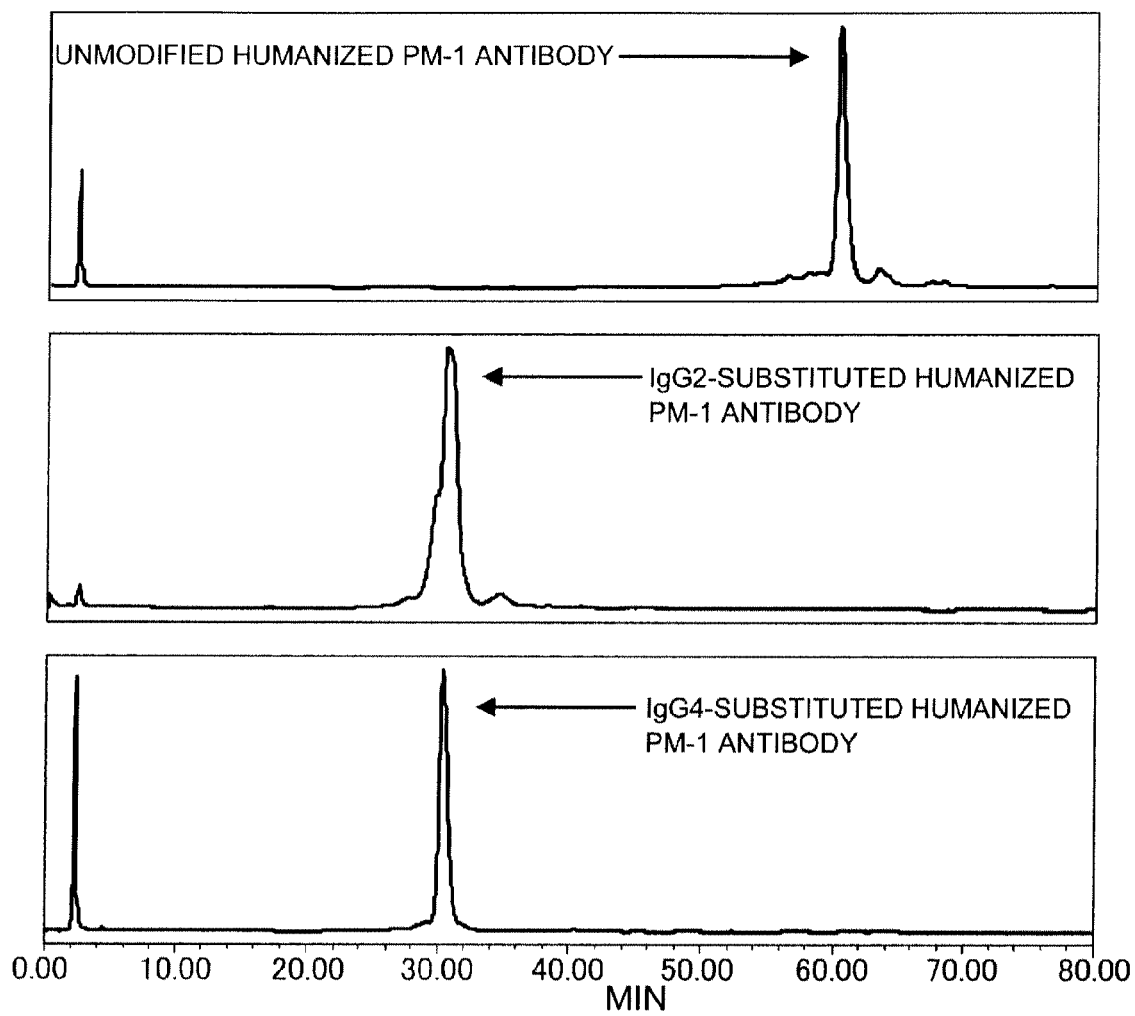
FIG. 17 depicts the result of cation exchange chromatographic analysis of singly expressed unmodified, IgG2-substituted, and IgG4-substituted humanized PM-1 antibodies. The result confirms that the peaks of the modified antibodies have been shifted compared to that of the unmodified antibody.
Figure 18:
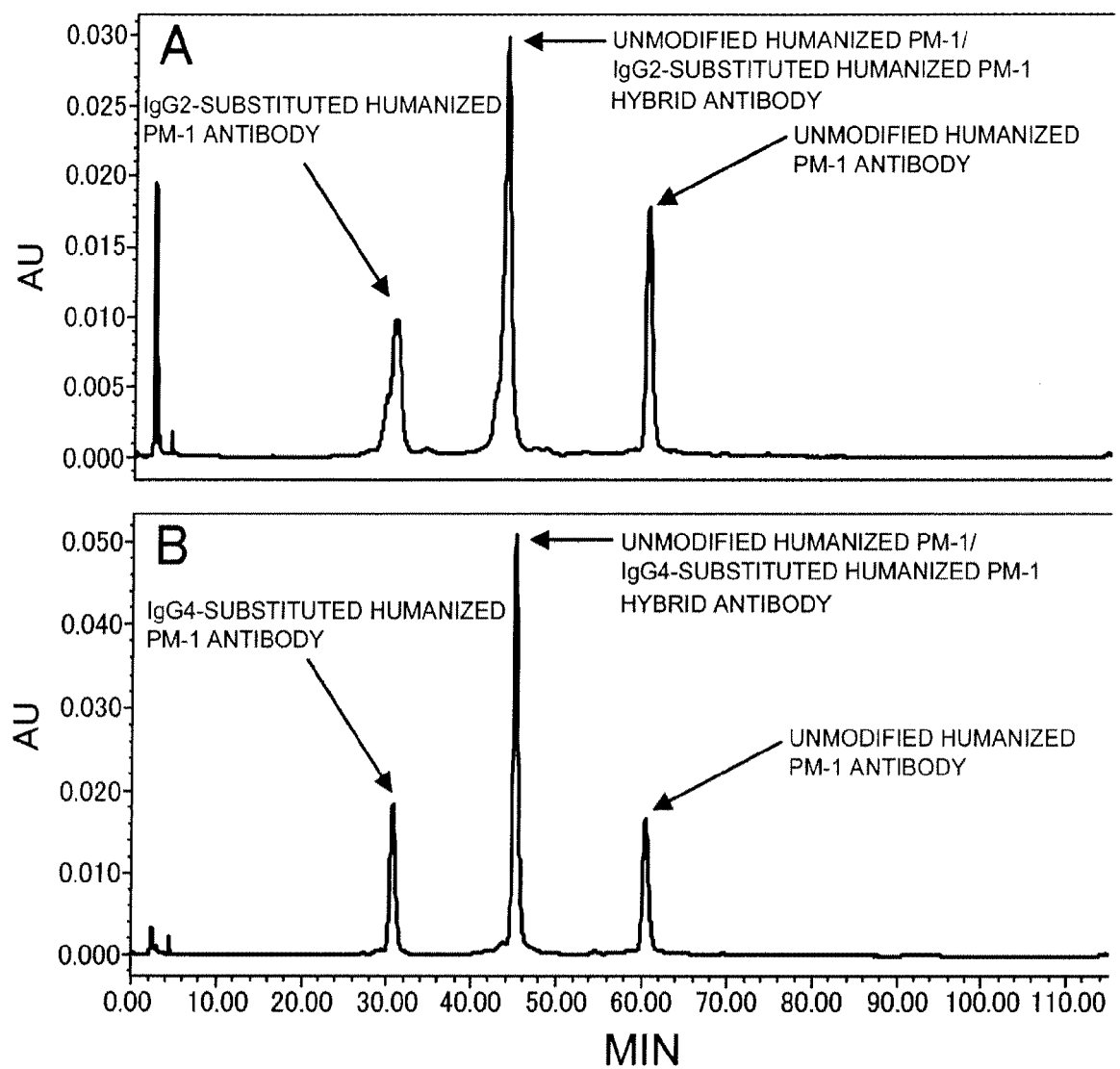
FIG. 18 depicts the result of cation exchange chromatographic analysis of the unmodified humanized PM-1 antibody coexpressed with the IgG2-substituted or IgG4-substituted humanized PM-1 antibody. As a result, the homodimers of each subclass and the heterodimer were observed as three major peaks in the combination of the unmodified humanized PM-1 antibody and the IgG2-substituted humanized PM-1 antibody, and in the combination of the unmodified humanized PM-1 antibody and the IgG4-substituted humanized PM-1 antibody. A: coexpression of the unmodified humanized PM-1 antibody and the IgG2-substituted humanized PM-1 antibody; B: coexpression of the unmodified humanized PM-1 antibody and the IgG4-substituted humanized PM-1 antibody.

Column: ProPac WCX-10, 4×250 mm, (Dionex)
    Mobile phase: A: 25 mmol/L MES/NaOH, pH 6.1
    B: 25 mmol/L MES/NaOH, 250 mmol/L NaCl, pH 6.1
    Flow rate: 0.5 mL/min
    Gradient: 25% B (5 min)→(105 min)→67% B→(1 min)→100% B (5 min)
    Detection: 280 nm The results of analysis of singly expressed unmodified, IgG2-substituted, and IgG4-substituted humanized PM-1 antibodies are shown in FIG. 17. The retention time of the unmodified humanized PM-1 antibody, IgG2-substituted humanized PM-1 antibody, and IgG4-substituted humanized PM-1 antibody was 60.2 minutes, 30.5 minutes, and 30.3 minutes, respectively. That is, the retention time was altered by slightly less than 30 minutes due to subclass substitution. On the other hand, the retention time was nearly the same for the IgG2-substituted humanized PM-1 antibody and the IgG4-substituted humanized PM-1 antibody, which showed a pI difference according to isoelectric focusing. Next, the results of analysis of coexpressing unmodified and IgG2-substituted humanized PM-1 antibodies, and coexpressing unmodified and IgG4-substituted humanized PM-1 antibodies are shown in FIG. 18. The homodimers of each subclass and heterodimer were observed as three main peaks in the combination of the unmodified humanized PM-1 antibody and IgG2-substituted humanized PM-1 antibody, and the combination of the unmodified humanized PM-1 antibody and IgG4-substituted humanized PM-1 antibody. The retention time was approximately 43.8 minutes for the unmodified humanized PM-1/IgG2-substituted humanized PM-1 hybrid antibody, and approximately 45.1 minutes for the unmodified humanized PM-1/IgG4-substituted humanized PM-1 hybrid antibody. That is, these antibodies were separated from the respective homodimers with a retention time difference of 10 minutes or more. It was shown in this examination that subclass hybrid antibodies can be produced by coexpressing a combination of expression vectors of subclass antibodies, and that the hybrid antibodies can be separated by ion exchange chromatography.

Example 13

Figure 19:
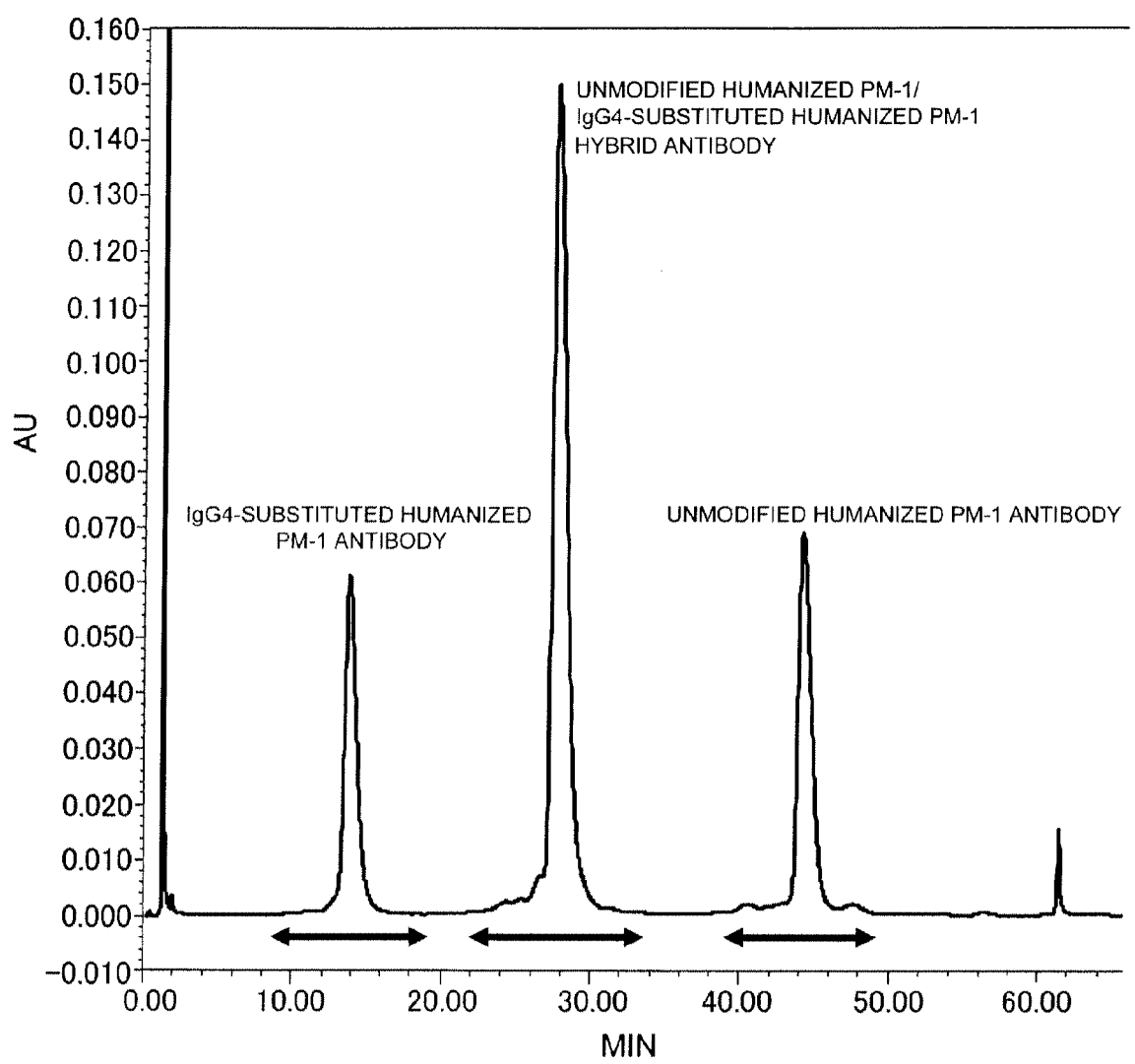
FIG. 19 depicts the result of purification of the homodimers and heterodimer by cation exchange chromatography from coexpression of the unmodified humanized PM-1 antibody and the IgG4-substituted humanized PM-1 antibody. As a result, three peaks were eluted in the following order: IgG4-substituted humanized PM-1 antibody homodimer, unmodified humanized PM-1/IgG4-substituted humanized PM-1 hybrid antibody, and unmodified humanized PM-1 antibody homodimer. These peaks were fractionated. Arrows indicate the approximate fractionation ranges.
Figure 20:
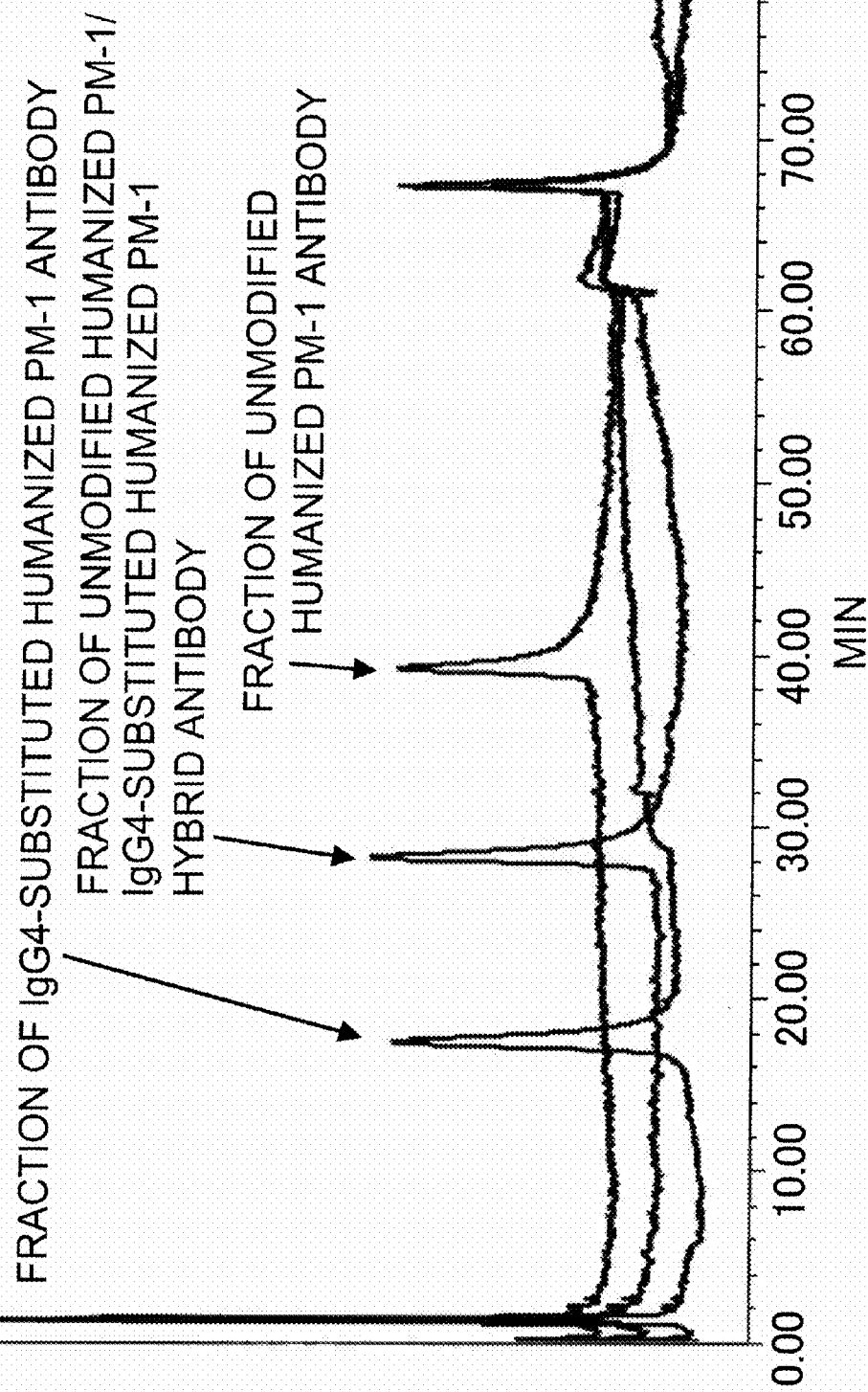
FIG. 20 depicts the result of rechromatography of the unmodified humanized PM-1 antibody homodimer, unmodified humanized PM-1/IgG4-substituted humanized PM-1 hybrid antibody, and IgG4-substituted humanized PM-1 antibody homodimer, which were purified by cation exchange chromatography. As a result, the subclass hybrid antibody was confirmed to be purified.

Separation and Purification of Subclass Hybrid Antibodies by Cation Exchange Chromatography The antibody solutions obtained in Example 11 were concentrated using Amicon-Ultra4 (Amicon), then enveloped in EasySep (TOMY SEIKO). After buffer exchange was performed by dialysis against 5 mM citric acid buffer (pH 6.5), subclass hybrid antibodies were purified under the following conditions.
Column: Poly CAT A, 4.6×100 mm, particle diameter: 3 μm, pore diameter: 150 nm (Poly LC)
Mobile Phase: A: 25 mmol/L MES/NaOH, pH 6.1
B: 25 mmol/L MES/NaOH, 250 mmol/L sodium acetate, pH 6.1
Flow rate: 1.0 mL/min
Gradient: 35% B (5 min)→(54 min)→65% B→ (1 min)→100% B (5 min)
Detection: 280 nm
Approximately 100 to 200 μg was loaded each time, and peaks of the unmodified humanized PM-1 antibody, unmodified humanized PM-1/IgG4-substituted humanized PM-1 subclass hybrid antibody, and IgG4-substituted humanized PM-1 antibody were fractionated. A chromatogram of the fractionations is shown in FIG. 19. Peak fractions from multiple experiments were combined, concentrated using Amicon-Ultra4 (Amicon), and then enveloped in EasySep (TOMY SEIKO). The buffer was exchanged by dialysis against PBS for activity measurement, or against 20 mM acetic acid buffer containing 150 mM NaCl, pH 6.0 for DSC measurement. The fractionated peaks were reanalyzed under conditions similar to those described above and the results are shown in FIG. 20. This shows that subclass hybrid antibodies can be fractionated and purified by ion exchange chromatography methods.

This technique enables separation of antibodies carrying a common H-chain variable region by using constant regions of different subclasses with different pI values. Thus, even if different H-chain variable regions do not have a pI difference, bispecific antibodies can be separated by ion exchange chromatography by linking the H-chain variable regions to subclass H-chain constant regions with different pI values. Furthermore, if the H-chain variable regions are different, the pI difference between the molecules can be increased to further facilitate separation and purification by combining the above technique with the technique for introducing mutations into the variable region as shown in Example 9. Even if introduction of mutations into the H-chain variable region is difficult, bispecific antibodies can be separated and purified by ion exchange chromatography by substituting the H-chain variable region with a naturally-occurring IgG subclass sequence, without worrying about antigenicity.

Example 14

Isoelectric Focusing of Fractionated and Purified Subclass Hybrid Antibody Products To evaluate the purity of the fractionated products, isoelectric focusing analysis was carried out.
Isoelectric focusing was carried out as follows. PhastGel Dry IEF (Amersham Biosciences) gel was swollen for about 30 minutes in the swelling solution described below using the Phastsystem Cassette (Amersham Biosciences).

| | |
|---|---|
| MilliQ water | 1.5 mL |
| Pharmalyte 5-8 for IEF (Amersham Biosciences) | 50 μL |
| Pharmalyte 8-10.5 for IEF (Amersham Biosciences) | 50 μL |

Electrophoresis was performed using the swollen gel by PhastSystem (Amersham Biosciences) according to the following program. The samples were applied to the gel in Step 2. A pI calibration kit (Amersham Biosciences) was used as the pI marker.

| | | | | | |
|---|---|---|---|---|---|
| Step 1: | 2000 V | 2.5 mA | 3.5 W | 15° C. | 75 Vh |
| Step 2: | 200 V | 2.5 mA | 3.5 W | 15° C. | 15 Vh |
| Step 3: | 2000 V | 2.5 mA | 3.5 W | 15° C. | 410 Vh |

Figure 21:
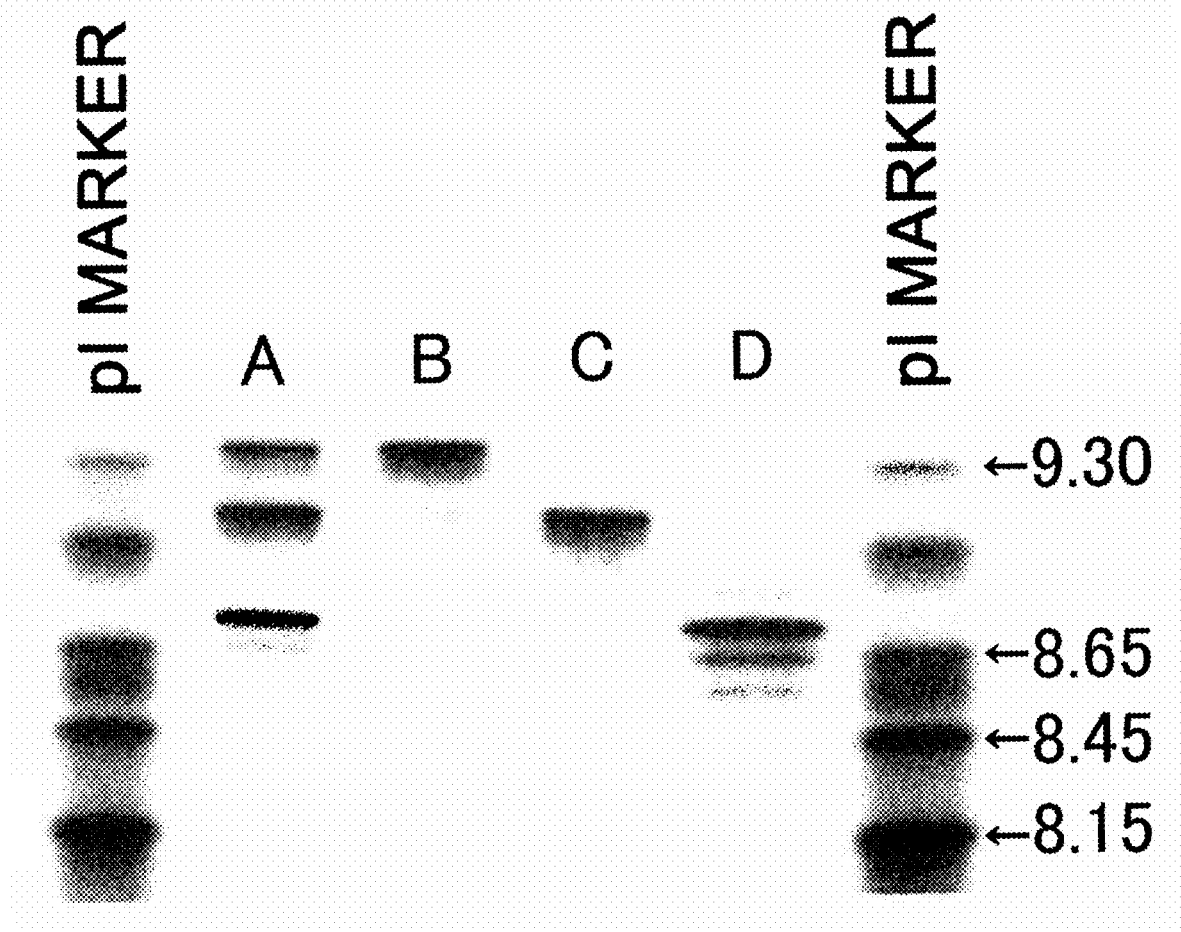
FIG. 21 is a photograph depicting the result of isoelectric focusing analysis of the unmodified humanized PM-1 antibody homodimer, unmodified/IgG4-substituted humanized PM-1 hybrid antibody, and IgG4-substituted humanized PM-1 antibody homodimer, which were purified by cation exchange chromatography. As a result, the subclass hybrid antibody of interest was confirmed to be purified. A: coexpression of the unmodified humanized PM-1 antibody and the IgG4-substituted humanized PM-1 antibody; B: fraction of the unmodified humanized PM-1 antibody; C: fraction of the unmodified humanized PM-1/IgG4-substituted humanized PM-1 hybrid antibody; D: fraction of the IgG4-substituted humanized PM-1 antibody.

After electrophoresis, the gel was fixed with 20% TCA, and then silver stained using a silver staining kit, protein (Amersham Biosciences) according to the protocol attached to the kit.
The results of analysis of the fractionated and purified subclass hybrid antibody products are shown in FIG. 21. It was shown that the products can be purified without containing any subclass homodimer by using ion exchange chromatography.

Example 15

Activity Assessment of Fractionated and Purified Subclass Hybrid Antibody Products 15-1. Establishment of Human gp130-Expressing BaF3 Cell Line and Human gp130/Human IL-6 Receptor-Coexpressing BaF3 Cell Line
To obtain a cell line showing IL-6-dependent growth, a BaF3 cell line expressing human gp130 was established as described below.
The full-length human gp130 cDNA (Hibi et al., Cell 1990; 63:1149-1157 (GenBank Accession No.

NM_002184)) was amplified by PCR, and cloned into the pCOS2Zeo expression vector, from which the DHFR gene expression site of pCHOI (Hirata et al., FEBS Letter 1994; 356:244-248) was removed, and to which a Zeocin resistance gene expression site was inserted, to construct pCOS2Zeo/gp130.

10 μg of pCOS2Zeo/gp130 was mixed with BaF3 cells ($0.8 \times 10^7$ cells) suspended in PBS, then a pulse was applied at 0.33 kV and a capacity of 950 pFD using Gene Pulser (Bio-Rad). BaF3 cells subjected to the gene transfer by electroporation treatment were cultured for one day and night in RPMI1640 medium (Invitrogen) containing 0.2 ng/mL of mouse interleukin-3 (Peprotech), 10% Fetal Bovine Serum (hereinafter referred to as FBS, HyClone). Then, the cells were selected by adding RPMI 1640 medium containing 100 ng/mL of human interleukin-6 (R&D), 100 ng/mL of soluble human interleukin-6 receptor (R&D systems), and 10% FBS, to establish a human gp130-expressing BaF3 cell line (hereinafter referred to as BaF3/gp130).

15-2. Assessment of the Activity of Fractionated and Purified Subclass Hybrid Antibody Products to Neutralize Human IL-6

IL-6 neutralizing activity was evaluated using BaF3/gp130 showing IL-6-dependent growth, as described below. Purified unmodified humanized PM-1 antibody, unmodified/IgG4-substituted humanized PM-1 subclass hybrid antibody, and IgG4-substituted humanized PM-1 antibody were diluted in RPMI1640 containing 10% FBS to 10 μg/mL. Seven three-fold serial dilutions were prepared in this solution, and 50 μL of each solution was dispensed into each well of a 96-well plate (CORNING). Next, after washing three times with RPMI1640 medium containing 10% FBS (HyClone), BaF3/gp130 was suspended at $5 \times 10^4$ cells/mL in RPMI 1640 medium containing 60 ng/mL of human interleukin-6 (TORAY), 60 ng/mL of soluble human IL-6 receptor (prepared by the present inventors' company), and 10% FBS. 50 μL of this suspension was added to each well and mixed. Then, antibody samples were dispensed. Soluble human IL-6 receptor was prepared by the method indicated below. A gene that encodes the 1st to the 344th amino acids of the soluble human IL-6 receptor (Yamasaki et al., Science 1988; 241:825-828 (GenBank Accession No. X12830)) was introduced into CHO cells. Then, the receptor was purified from the culture supernatant. Cells were cultured for 72 hours under conditions of 37° C. and 5% $CO_2$. Then, WST-8 reagent (Cell Counting Kit-8, Dojindo Laboratories) diluted two-fold with PBS was added at 20 μL/well. Immediately after, the absorbance at 450 nm (reference wavelength: 620 nm) was measured using SUNRISE CLASSIC (TECAN). After a two-hour culture, the absorbance at 450 nm (reference wavelength: 620 nm) was measured again. The IL-6 neutralizing activity was evaluated using the change in absorbance during the two-hour culture as an index.

Figure 22:
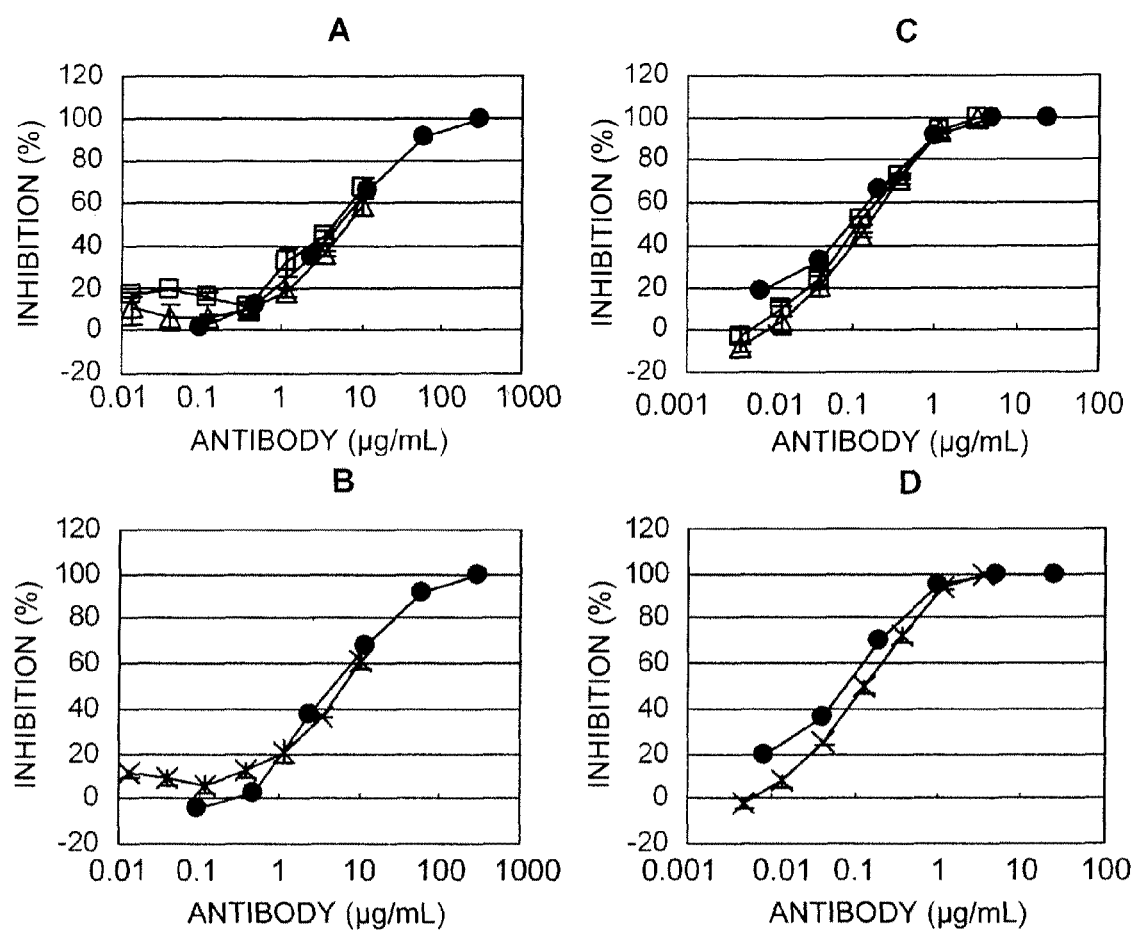
FIG. 22 depicts the result of evaluating the human IL-6 neutralizing activity of the unmodified humanized PM-1 antibody homodimer, unmodified humanized PM-1/IgG4-substituted humanized PM-1 hybrid antibody, and IgG4-substituted humanized PM-1 antibody homodimer, which were purified by cation exchange chromatography. As a result, all the antibodies showed a neutralizing activity equivalent to that of the purified humanized PM-1 antibody. A and B: BaF3 cell line expressing human gp130; C and D: BaF3 cell line coexpressing human gp130 and human IL-6 receptor. Filled circle (●): humanized PM-1 antibody purified product (bulk); open square (□): unmodified humanized PM-1 antibody; open triangle (Δ): IgG4-substituted humanized PM-1 antibody; x: unmodified humanized PM-1/IgG4-substituted humanized PM-1 hybrid antibody.

As a result, as shown in FIG. 22, the fractioned and purified unmodified humanized PM-1 antibody, unmodified/IgG4-substituted humanized PM-1 subclass hybrid antibody, and IgG4-substituted humanized PM-1 antibody had neutralizing activities equivalent to that of a purified product of humanized PM-1 antibody (bulk). In view of the above, it was shown that the subclass hybrid antibodies do not lose their original antigen-binding activities, and they function as neutralizing antibodies.

INDUSTRIAL APPLICABILITY

In the methods of the present invention, the isoelectric point of an antibody can be altered by only a small number of amino acid substitutions without changing its structure/function (activity). This enables efficient purification of bispecific antibodies to high purity using a standard chromatography column. The high purity allows development of the bispecific antibodies into pharmaceuticals. Thus, the methods of the present invention are highly useful for developing bispecific antibodies as pharmaceuticals.

Bispecific antibodies that actually have activities can be obtained efficiently by the methods of the present invention.

The invention claimed is:

1. A method for producing a modified multispecific human or humanized antibody comprising a first polypeptide and a second polypeptide, wherein the method comprises the steps of:
   (a) providing a pair of nucleic acids respectively encoding a pair of polypeptides, wherein the pair of polypeptides is either a pair of human or humanized antibody heavy chains or a pair of human or humanized antibody light chains;
   (b) modifying one or both of the nucleic acids to alter one or more surface amino acid residues of the encoded polypeptide(s), thereby generating a modified pair of nucleic acids encoding a modified pair of polypeptides, wherein the modification increases the difference between the respective isoelectric points of the pair of polypeptides;
   (c) providing host cells containing the modified pair of nucleic acids;
   (d) culturing the host cells so that they express the modified pair of nucleic acids; and
   (e) using a method comprising ion exchange chromatography to purify, from the host cell culture, a modified human or humanized multispecific antibody comprising the modified pair of polypeptides, wherein ion exchange chromatography separates the modified human or humanized multispecific antibody from homomultimers formed from each polypeptide of the modified pair of polypeptides based on the difference between the respective isoelectric points of the modified pair of polypeptides,
   wherein the one or more surface amino acid residues that are altered comprise at least one amino acid residue located at a position or positions selected from heavy chain variable region positions 1, 3, 5, 8, 10, 12, 13, 15, 16, 19, 23, 25, 26, 27, 39, 42, 43, 44, 46, 68, 71, 72, 73, 75, 76, 81, 82b, 83, 85, 86, 97, 105, 108, 110, and 112 (Kabat numbering), heavy chain constant region positions 137, 196, 203, 214, 217, 233, 268, 274, 276, 297, 355, 392, 419, and 435 (EU numbering), and light chain variable region positions 1, 3, 7, 8, 9, 11, 12, 16, 17, 18, 20, 22, 38, 39, 41, 42, 43, 45, 46, 49, 57, 60, 63, 65, 66, 68, 69, 70, 74, 76, 77, 79, 80, 81, 85, 100, 103, 105, 106, 107, and 108 (Kabat numbering).

2. The method of claim 1, wherein the increased difference in isoelectric points resulting from the modification of step (b) is adequate to permit separation, in ion exchange chromatography, of a peak representing a homomultimer comprising two copies of the first polypeptide of the modified pair of polypeptides, a peak representing a homomultimer comprising two copies of the second polypeptide of the modified pair of polypeptides, and a peak representing a heteromultimer comprising the first and second polypeptides of the modified pair of polypeptides.

3. The method of claim 1, wherein the pair of polypeptides is a pair of human or humanized antibody heavy chains.

4. The method of claim 1, wherein each polypeptide of the modified pair of polypeptides comprises a heavy chain constant region, and the isoelectric point of the heavy chain constant region of the first polypeptide of the modified pair of polypeptides is different from the isoelectric point of the heavy chain constant region of the second polypeptide of the modified pair of polypeptides.

5. The method of claim 4, wherein one of the heavy chain constant regions of the modified pair of polypeptides is a human IgG1 heavy chain constant region and the other is a human IgG4 or human IgG2 heavy chain constant region.

6. The method of claim 1, wherein the modified multispecific antibody of step (e) is a bispecific antibody.

7. The method of claim 3, wherein the modified multispecific antibody comprises two copies of an antibody light chain, and wherein each polypeptide of the modified pair of polypeptides associates with one of the copies of the antibody light chain.

8. The method of claim 3, wherein the one or more surface amino acid residues that are altered comprise at least one amino acid residue located at a position or positions selected from heavy chain variable region positions 1, 3, 5, 8, 10, 12, 13, 15, 16, 19, 23, 25, 26, 27, 39, 42, 43, 44, 46, 68, 71, 72, 73, 75, 76, 81, 82b, 83, 85, 86, 97, 105, 108, 110, and 112 (Kabat numbering).

9. The method of claim 3, wherein the one or more surface amino acid residues that are altered comprise at least one amino acid residue located at a position or positions selected from heavy chain constant region positions 137, 196, 203, 214, 217, 233, 268, 274, 276, 297, 355, 392, 419, and 435 (EU numbering).

10. The method of claim 1, wherein the pair of polypeptides is a pair of human or humanized antibody light chains.

11. The method of claim 10, wherein the one or more surface amino acid residues that are altered comprise at least one amino acid residue located at a position or positions selected from light chain variable region positions 1, 3, 7, 8, 9, 11, 12, 16, 17, 18, 20, 22, 38, 39, 41, 42, 43, 45, 46, 49, 57, 60, 63, 65, 66, 68, 69, 70, 74, 76, 77, 79, 80, 81, 85, 100, 103, 105, 106, 107, and 108 (Kabat numbering).

12. The method of claim 1, wherein the difference between the respective isoelectric points of the pair of polypeptides post-modification is 0.5 or more.

13. The method of claim 1, wherein the difference between the respective isoelectric points of the pair of polypeptides post-modification is 0.7 or more.

14. The method of claim 1, wherein the difference between the respective isoelectric points of the pair of polypeptides post-modification is 0.9 or more.

15. The method of claim 3, wherein one or more of the surface amino acid residues that are altered in one or both polypeptides are located at a position or positions selected from heavy chain variable region positions 10, 12, 23, 39, 43, and 105 (Kabat numbering).

16. The method of claim 15, wherein one of the polypeptides of the modified pair of polypeptides has a positively charged amino acid residue at a position selected from heavy chain variable region positions 10, 12, 23, 39, 43, and 105 (Kabat numbering), and the other polypeptide of the modified pair of polypeptides has a negatively charged amino acid residue at the same position.

17. The method of claim 15, wherein one of the polypeptides of the modified pair of polypeptides has a charged amino acid residue at a position selected from heavy chain variable region positions 10, 12, 23, 39, 43, and 105 (Kabat numbering), and the other polypeptide of the modified pair of polypeptides has an uncharged amino acid residue at the same position.

18. The method of claim 16, wherein the positively charged amino acid residue is selected from the group consisting of lysine (K), arginine (R), and histidine (H), and the negatively charged amino acid residue is selected from the group consisting of glutamic acid (E) and aspartic acid (D).

19. The method of claim 17, wherein the charged amino acid residue is selected from the group consisting of lysine (K), arginine (R), histidine (H), glutamic acid (E), and aspartic acid (D).

20. The method of claim 1, wherein the modification results in one of the polypeptides of the modified pair of polypeptides being modified to have an isoelectric point higher than prior to the modification, and the other polypeptide of the modified pair of polypeptides being modified to have an isoelectric point lower than prior to the modification.

21. The method of claim 1, wherein, after the modification of (b), all of the altered surface amino acid residues of one of the polypeptides of the modified pair of polypeptides are positively charged amino acid residues, and all of the altered surface amino acid residues of the other polypeptide of the modified pair of polypeptides are negatively charged amino acid residues.

22. The method of claim 1, wherein, after the modification of (b), the altered surface amino acid residues of one of the polypeptides of the modified pair of polypeptides are either all positively charged amino acid residues or all negatively charged amino acid residues, and all of the altered surface amino acid residues of the other polypeptide of the modified pair of polypeptides are uncharged amino acid residues.

23. The method of claim 1, wherein the modified pair of polypeptides are antibody heavy chains, each comprising a constant region that is not a wild-type constant region.

24. The method of claim 4, wherein the heavy chain constant regions of the first and second polypeptides of the modified pair of polypeptides are of the same IgG class.

25. The method of claim 1, wherein the altered one or more surface amino acid residues of the modified pair of polypeptides are all variable domain residues.

* * * * *

SEQUENCE LISTING

```
<160> NUMBER OF SEQ ID NOS: 25

<210> SEQ ID NO 1
<211> LENGTH: 354
<212> TYPE: DNA
<213> ORGANISM: Artificial
<220> FEATURE:
<223> OTHER INFORMATION: An artificially synthesized sequence

<400> SEQUENCE: 1
caggtccagc ttgtgcagtc tggggctgag gtgaagaagc ctgggtcctc agtgaaggtt      60
tcctgcaagg cctctggagg caccttcagt gactactata tgcactgggt gcgccaggcc     120
cccggacaag ggcttgagtg gatgggatac attaatccta gcagtggtta tactaagtac     180
aatcggaagt tcagggacag agtcaccatt accgcggaca atccacgag cacagcctac      240 atggagctga gcagcctgag atctgaagac acggctgtgt attactgtgc gagaggggt      300 aacggttact accttgacta ctggggccag ggcaccacgg tcaccgtctc ctca           354

<210> SEQ ID NO 2
<211> LENGTH: 118
<212> TYPE: PRT
<213> ORGANISM: Artificial
<220> FEATURE:
<223> OTHER INFORMATION: An artificially synthesized sequence
```

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Gln Gly Thr
            100                 105                 110

Thr Val Thr Val Ser Ser
        115

<210> SEQ ID NO 3
<211> LENGTH: 357
<212> TYPE: DNA
<213> ORGANISM: Artificial
<220> FEATURE:
<223> OTHER INFORMATION: An artificially synthesized sequence

<400> SEQUENCE: 3
caggtgcagc tggtgcagtc tggacctgac gtgaagaagc cgggggcctc agtgaaggtc     60
tcctgcaagg cctctggcta catgttttcc gacaacaaca tggactgggc gcgacaggcc    120
cctggacaag ggcttgagtg gatgggagat attaatacta aaagtggtgg ttctatctac    180
aaccagaagt tcaagggcag agtcatcatg accatagaca atccacgggg cacagcctac    240
atggaattga ggagcctgag atcagacgac acggccatat attactgtgc gaggaggagg    300
agctacggct actactttga ctactggggc cagggaaccc tggtcaccgt ctcctca       357

<210> SEQ ID NO 4
<211> LENGTH: 119
<212> TYPE: PRT
<213> ORGANISM: Artificial
<220> FEATURE:
<223> OTHER INFORMATION: An artificially synthesized sequence

<400> SEQUENCE: 4

Gln Val Gln Leu Val Gln Ser Gly Pro Asp Val Lys Lys Pro Gly Ala
1               5                   10                  15

Ser Val Lys Val Ser Cys Lys Ala Ser Gly Tyr Met Phe Ser Asp Asn
            20                  25                  30

Asn Met Asp Trp Ala Arg Gln Ala Pro Gly Gln Gly Leu Glu Trp Met
        35                  40                  45

Gly Asp Ile Asn Thr Lys Ser Gly Gly Ser Ile Tyr Asn Gln Lys Phe
    50                  55                  60

Lys Gly Arg Val Ile Met Thr Ile Asp Lys Ser Thr Gly Thr Ala Tyr
65                  70                  75                  80

Met Glu Leu Arg Ser Leu Arg Ser Asp Asp Thr Ala Ile Tyr Tyr Cys
                85                  90                  95

Ala Arg Arg Arg Ser Tyr Gly Tyr Tyr Phe Asp Tyr Trp Gly Gln Gly
            100                 105                 110

Thr Leu Val Thr Val Ser Ser
        115

<210> SEQ ID NO 5
<211> LENGTH: 318
<212> TYPE: DNA
<213> ORGANISM: Artificial
<220> FEATURE:
<223> OTHER INFORMATION: An artificially synthesized sequence

<400> SEQUENCE: 5
gacatcgtga tgacccagtc tccatcctcc ctgtctgcat ctgtaggaga cagagtcacc    60
atcacttgca aggccagtca gaatgtgggg actgctgtag cctggtatca gcagaaacca   120
gggaaagccc ctaagctcct gatctattcg catcctacc ggtacagtgg ggtcccatca   180
aggttcagtg gcagtcgata tgggacagat ttcactctca ccatctcaag cttgcaacct   240
gaagatttag caacttacta ctgtcagcaa tatagcaact atatcacgtt cggcggaggg   300
accaaggtgg agatcaaa                                                  318

<210> SEQ ID NO 6
<211> LENGTH: 106
<212> TYPE: PRT
<213> ORGANISM: Artificial
<220> FEATURE:
<223> OTHER INFORMATION: An artificially synthesized sequence

<400> SEQUENCE: 6

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Ser Asn Tyr Ile Thr
                85                  90                  95

Phe Gly Gly Gly Thr Lys Val Glu Ile Lys
            100                 105

<210> SEQ ID NO 7
<211> LENGTH: 118
<212> TYPE: PRT
<213> ORGANISM: Artificial
<220> FEATURE:
<223> OTHER INFORMATION: An artificially synthesized sequence

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Glu Gly Thr
            100                 105                 110

Thr Val Thr Val Ser Ser
        115

<210> SEQ ID NO 8
<211> LENGTH: 118
<212> TYPE: PRT
<213> ORGANISM: Artificial
<220> FEATURE:
<223> OTHER INFORMATION: An artificially synthesized sequence

<400> SEQUENCE: 8

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Asp Tyr
                20                  25                  30

Tyr Met His Trp Val Arg Gln Ala Pro Gly Glu Gly Leu Glu Trp Met
            35                  40                  45

Gly Tyr Ile Asn Pro Ser Ser Gly Tyr Thr Lys Tyr Asn Arg Lys Phe
        50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Glu Gly Thr
            100                 105                 110

Thr Val Thr Val Ser Ser
        115

<210> SEQ ID NO 9
<211> LENGTH: 118
<212> TYPE: PRT
<213> ORGANISM: Artificial
<220> FEATURE:
<223> OTHER INFORMATION: An artificially synthesized sequence

<400> SEQUENCE: 9

Gln Val Gln Leu Val Gln Ser Gly Ala Glu Val Lys Lys Pro Gly Ser
1               5                   10                  15

Ser Val Lys Val Ser Cys Thr Ala Ser Gly Gly Thr Phe Ser Asp Tyr
                20                  25                  30

Tyr Met His Trp Val Arg Gln Ala Pro Gly Glu Gly Leu Glu Trp Met
            35                  40                  45

Gly Tyr Ile Asn Pro Ser Ser Gly Tyr Thr Lys Tyr Asn Arg Lys Phe
        50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Glu Gly Thr
            100                 105                 110

Thr Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: An artificially synthesized sequence

<400> SEQUENCE: 10

```
Gln Val Gln Leu Val Gln Ser Gly Ala Glu Val Val Lys Pro Gly Ser
1               5                   10                  15

Ser Val Lys Val Ser Cys Thr Ala Ser Gly Gly Thr Phe Ser Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Gly Tyr Tyr Leu Asp Tyr Trp Gly Glu Gly Thr
            100                 105                 110

Thr Val Thr Val Ser Ser
        115
```

<210> SEQ ID NO 11
<211> LENGTH: 118
<212> TYPE: PRT
<213> ORGANISM: Artificial
<220> FEATURE:
<223> OTHER INFORMATION: An artificially synthesized sequence

<400> SEQUENCE: 11

```
Glu Val Gln Leu Val Gln Ser Gly Ala Glu Val Val Lys Pro Gly Ser
1               5                   10                  15

Ser Val Lys Val Ser Cys Thr Ala Ser Gly Tyr Thr Phe Ser Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Gly Tyr Tyr Leu Asp Tyr Trp Gly Glu Gly Thr
            100                 105                 110

Thr Val Thr Val Ser Ser
        115
```

<210> SEQ ID NO 12
<211> LENGTH: 118
<212> TYPE: PRT
<213> ORGANISM: Artificial
<220> FEATURE:
<223> OTHER INFORMATION: An artificially synthesized sequence

<400> SEQUENCE: 12

```
Glu Val Gln Leu Val Gln Ser Gly Ala Glu Val Gln Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Glu Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gln Gly Tyr Tyr Leu Asp Tyr Trp Gly Glu Gly Thr
            100                 105                 110

Thr Val Thr Val Ser Ser
            115

<210> SEQ ID NO 13
<211> LENGTH: 118
<212> TYPE: PRT
<213> ORGANISM: Artificial
<220> FEATURE:
<223> OTHER INFORMATION: An artificially synthesized sequence

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Tyr Met His Trp Val Arg Gln Ala Pro Gly Gln Gly Leu Glu Trp Met
        35                  40                  45

Gly Tyr Ile Asn Pro Ser Ser Gly Tyr Thr Lys Tyr Asn Arg Lys Phe
    50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Gly Tyr Tyr Leu Asp Tyr Trp Gly Gln Gly Thr
            100                 105                 110

Thr Val Thr Val Ser Ser
            115

<210> SEQ ID NO 14
<211> LENGTH: 119
<212> TYPE: PRT
<213> ORGANISM: Artificial
<220> FEATURE:
<223> OTHER INFORMATION: An artificially synthesized sequence

<400> SEQUENCE: 14

Gln Val Gln Leu Val Gln Ser Gly Pro Asp Val Lys Lys Pro Gly Ala
1               5                   10                  15

Ser Val Lys Val Ser Cys Lys Ala Ser Gly Tyr Met Phe Ser Asp Asn
            20                  25                  30

Asn Met Asp Trp Ala Arg Gln Ala Pro Gly Lys Gly Leu Glu Trp Met
        35                  40                  45

Gly Asp Ile Asn Thr Lys Ser Gly Gly Ser Ile Tyr Asn Gln Lys Phe
    50                  55                  60
```

Lys Gly Arg Val Ile Met Thr Ile Asp Lys Ser Thr Gly Thr Ala Tyr
65                  70                  75                  80

Met Glu Leu Arg Ser Leu Arg Ser Asp Thr Ala Ile Tyr Tyr Cys
                85                  90                  95

Ala Arg Arg Arg Ser Tyr Gly Tyr Tyr Phe Asp Tyr Trp Gly Arg Gly
            100                 105                 110

Thr Leu Val Thr Val Ser Ser
        115

<210> SEQ ID NO 15
<211> LENGTH: 119
<212> TYPE: PRT
<213> ORGANISM: Artificial
<220> FEATURE:
<223> OTHER INFORMATION: An artificially synthesized sequence

<400> SEQUENCE: 15

Gln Val Gln Leu Val Gln Ser Gly Pro Asp Val Lys Lys Pro Gly Ala
1               5                   10                  15

Ser Val Lys Val Ser Cys Lys Ala Ser Gly Tyr Met Phe Ser Asp Asn
            20                  25                  30

Asn Met Asp Trp Ala Arg Lys Ala Pro Gly Lys Gly Leu Glu Trp Met
        35                  40                  45

Gly Asp Ile Asn Thr Lys Ser Gly Gly Ser Ile Tyr Asn Gln Lys Phe
    50                  55                  60

Lys Gly Arg Val Ile Met Thr Ile Asp Lys Ser Thr Gly Thr Ala Tyr
65                  70                  75                  80

Met Glu Leu Arg Ser Leu Arg Ser Asp Thr Ala Ile Tyr Tyr Cys
                85                  90                  95

Ala Arg Arg Arg Ser Tyr Gly Tyr Tyr Phe Asp Tyr Trp Gly Arg Gly
            100                 105                 110

Thr Leu Val Thr Val Ser Ser
        115

<210> SEQ ID NO 16
<211> LENGTH: 119
<212> TYPE: PRT
<213> ORGANISM: Artificial
<220> FEATURE:
<223> OTHER INFORMATION: An artificially synthesized sequence

<400> SEQUENCE: 16

Glu Val Gln Leu Val Gln Ser Gly Ala Gln Val Lys Lys Pro Gly Ala
1               5                   10                  15

Ser Val Lys Val Ser Cys Lys Ala Ser Gly Tyr Thr Phe Ser Asp Asn
            20                  25                  30

Asn Met Asp Trp Val Arg Gln Ala Pro Gly Lys Gly Leu Glu Trp Met
        35                  40                  45

Gly Asp Ile Asn Thr Lys Ser Gly Gly Ser Ile Tyr Asn Gln Lys Phe
    50                  55                  60

Lys Gly Arg Val Ile Met Thr Ile Asp Lys Ser Thr Gly Thr Ala Tyr
65                  70                  75                  80

Met Glu Leu Arg Ser Leu Arg Ser Asp Asp Thr Ala Ile Tyr Tyr Cys
                85                  90                  95

Ala Arg Arg Arg Ser Tyr Gly Tyr Tyr Phe Asp Tyr Trp Gly Arg Gly
            100                 105                 110

Thr Leu Val Thr Val Ser Ser

<210> SEQ ID NO 17
<211> LENGTH: 106
<212> TYPE: PRT
<213> ORGANISM: Artificial
<220> FEATURE:
<223> OTHER INFORMATION: An artificially synthesized sequence

<400> SEQUENCE: 17

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Ser Asn Tyr Ile Thr
                85                  90                  95

Phe Gly Gln Gly Thr Lys Val Glu Ile Lys
            100                 105
```

<210> SEQ ID NO 18
<211> LENGTH: 106
<212> TYPE: PRT
<213> ORGANISM: Artificial
<220> FEATURE:
<223> OTHER INFORMATION: An artificially synthesized sequence

<400> SEQUENCE: 18

```
Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ala Ser Gly Val Pro Ser Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Ser Asn Tyr Ile Thr
                85                  90                  95

Phe Gly Gln Gly Thr Lys Val Glu Ile Lys
            100                 105
```

<210> SEQ ID NO 19
<211> LENGTH: 119
<212> TYPE: PRT
<213> ORGANISM: Mus musculus

<400> SEQUENCE: 19

```
Met Glu Val Gln Leu Gln Ser Gly Ala Glu Leu Val Lys Pro Gly
1               5                   10                  15

Ala Ser Val Lys Leu Ser Cys Thr Ala Ser Gly Phe Asn Ile Lys Asp
            20                  25                  30

Tyr Tyr Met His Trp Ile Lys Gln Arg Pro Gly Gln Gly Leu Glu Trp
```

```
                35                  40                  45
Leu Gly Tyr Ile Asn Pro Ser Ser Gly Tyr Thr Lys Tyr Asn Arg Lys
        50                  55                  60
Phe Arg Asp Lys Ala Thr Leu Thr Ala Asp Lys Ser Ser Ser Thr Ala
65                  70                  75                  80
Tyr Met Gln Leu Thr Ser Leu Thr Tyr Glu Asp Ser Ala Val Tyr Tyr
                85                  90                  95
Cys Ala Arg Gly Gly Asn Gly Tyr Tyr Leu Asp Tyr Trp Gly Gln Gly
            100                 105                 110
Thr Thr Leu Thr Val Ser Ser
            115

<210> SEQ ID NO 20
<211> LENGTH: 120
<212> TYPE: PRT
<213> ORGANISM: Mus musculus

<400> SEQUENCE: 20

Met Gln Val Gln Leu Gln Gln Ser Gly Pro Glu Leu Val Lys Pro Gly
1               5                  10                  15
Ala Ser Val Lys Ile Ser Cys Lys Ala Ser Gly Tyr Thr Phe Thr Asp
                20                  25                  30
Asn Asn Met Asp Trp Val Lys Gln Ser His Gly Lys Gly Leu Glu Trp
            35                  40                  45
Ile Gly Asp Ile Asn Thr Lys Ser Gly Gly Ser Ile Tyr Asn Gln Lys
        50                  55                  60
Phe Lys Gly Lys Ala Thr Leu Thr Ile Asp Lys Ser Ser Ser Thr Ala
65                  70                  75                  80
Tyr Met Glu Leu Arg Ser Leu Thr Ser Glu Asp Thr Ala Val Tyr Tyr
                85                  90                  95
Cys Ala Arg Arg Arg Ser Tyr Gly Tyr Tyr Phe Asp Tyr Trp Gly Gln
            100                 105                 110
Gly Thr Thr Leu Thr Val Ser Ser
            115                 120

<210> SEQ ID NO 21
<211> LENGTH: 107
<212> TYPE: PRT
<213> ORGANISM: Homo sapiens

<400> SEQUENCE: 21

Asp Ile Val Met Thr Gln Ser His Lys Phe Met Ser Thr Ser Val Gly
1               5                  10                  15
Asp Arg Val Ser Ile Thr Cys Lys Ala Ser Gln Asn Val Gly Thr Ala
                20                  25                  30
Val Ala Trp Tyr Gln Gln Lys Pro Gly Gln Ser Pro Lys Leu Leu Ile
            35                  40                  45
Tyr Ser Ala Ser Tyr Arg Tyr Ser Gly Val Pro Asp Arg Phe Thr Gly
        50                  55                  60
Ser Arg Tyr Gly Thr Asp Phe Thr Leu Thr Ile Ser Asn Val Gln Ser
65                  70                  75                  80
Glu Asp Leu Ala Asp Tyr Leu Cys Gln Gln Tyr Ser Asn Tyr Ile Thr
                85                  90                  95
Phe Gly Gly Gly Thr Lys Leu Glu Leu Lys Arg
            100                 105
```

<210> SEQ ID NO 22
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 22
caccgtctcc tcagcctcca ccaa                                         24

<210> SEQ ID NO 23
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 23
gtggcactca tttacccgga gaca                                         24

<210> SEQ ID NO 24
<211> LENGTH: 981
<212> TYPE: DNA
<213> ORGANISM: Homo sapiens

<400> SEQUENCE: 24
gctagcacca agggcccatc ggtcttcccc ctggcgccct gctccaggag cacctccgag     60
agcacagcgg ccctgggctg cctggtcaag gactacttcc ccgaaccggt gacggtgtcg    120
tggaactcag gcgctctgac cagcggcgtg cacaccttcc cggctgtcct acagtcctca    180
ggactctact ccctcagcag cgtggtgacc gtgccctcca gcaacttcgg cacccagacc    240
tacacctgca acgtagatca caagcccagc aacaccaagg tggacaagac agttgagcgc    300
aaatgttgtg tcgagtgccc accgtgccca gcaccacctg tggcaggacc gtcagtcttc    360
ctcttccccc caaaacccaa ggacaccctc atgatctccc ggacccctga ggtcacgtgc    420
gtggtggtgg acgtgagcca cgaagacccc gaggtccagt tcaactggta cgtggacggc    480
gtggaggtgc ataatgccaa gacaaagcca cgggaggagc agttcaacag cacgttccgt    540
gtggtcagcg tcctcaccgt cgtgcaccag gactggctga acggcaagga gtacaagtgc    600
aaggtctcca acaaaggcct cccagccccc atcgagaaaa ccatctccaa aaccaaaggg    660
cagccccgag aaccacaggt gtacaccctg cccccatccc gggaggagat gaccaagaac    720
caggtcagcc tgacctgcct ggtcaaaggc ttctacccca gcgacatcgc cgtggagtgg    780
gagagcaatg ggcagccgga gaacaactac aagaccacac tcccatgct ggactccgac    840
ggctccttct tcctctacag caagctcacc gtggacaaga gcaggtggca gcagggaac    900
gtcttctcat gctccgtgat gcatgaggct ctgcacaacc actacacaca gaagagcctc    960
tccctgtctc cgggtaaatg a                                             981

<210> SEQ ID NO 25
<211> LENGTH: 326
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
                225                 230                 235             240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
            305                 310                 315             320

Ser Leu Ser Pro Gly Lys
            325
```